United States Patent
Azad et al.

(10) Patent No.: US 7,396,584 B2
(45) Date of Patent: Jul. 8, 2008

(54) CROSSLINKED POLYAMINE COATING ON SUPERABSORBENT HYDROGELS

(75) Inventors: Michael M. Azad, Charlotte, NC (US); Norbert Herfert, Charlotte, NC (US); Michael Mitchell, Waxhaw, NC (US); Jim Robinson, Chesapeake, VA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 96 days.

(21) Appl. No.: 10/495,149

(22) PCT Filed: Nov. 15, 2002

(86) PCT No.: PCT/EP02/12808

§ 371 (c)(1),
(2), (4) Date: May 10, 2004

(87) PCT Pub. No.: WO03/043670

PCT Pub. Date: May 30, 2003

(65) Prior Publication Data

US 2005/0013992 A1 Jan. 20, 2005

Related U.S. Application Data

(60) Provisional application No. 60/331,727, filed on Nov. 21, 2001.

(30) Foreign Application Priority Data

Jan. 25, 2002 (EP) .................................. 02001776

(51) Int. Cl.
*B32B 27/14* (2006.01)
*B32B 5/16* (2006.01)

(52) U.S. Cl. .................... 428/327; 428/297.4; 428/372; 428/407

(58) Field of Classification Search ................ 428/327, 428/297.4, 372, 407
See application file for complete search history.

(56) References Cited

U.S. PATENT DOCUMENTS

| | | | |
|---|---|---|---|
| 2,788,003 A | 4/1957 | Morin | |
| 3,612,055 A | 10/1971 | Mesek et al. | |
| 3,938,522 A | 2/1976 | Repke | |
| 4,541,871 A * | 9/1985 | Obayashi et al. ......... | 106/193.1 |
| 5,324,561 A | 6/1994 | Rezai et al. | |
| 5,382,610 A | 1/1995 | Harada et al. | |
| 5,607,550 A | 3/1997 | Akers | |
| 5,614,269 A | 3/1997 | Hoskins et al. | |
| 5,614,561 A | 3/1997 | Martin | |
| 5,756,159 A | 5/1998 | Hoskins et al. | |
| 5,843,575 A * | 12/1998 | Wang et al. .................. | 428/407 |
| 5,849,405 A | 12/1998 | Wang et al. | |
| 5,851,672 A | 12/1998 | Wang et al. | |
| 5,883,158 A | 3/1999 | Nambu et al. | |
| 5,985,432 A | 11/1999 | Wang et al. | |
| 5,997,690 A | 12/1999 | Woodrum | |
| 6,342,298 B1 * | 1/2002 | Evans et al. ................. | 428/373 |
| 6,342,652 B1 * | 1/2002 | Harada et al. ............... | 604/358 |
| 6,376,618 B1 * | 4/2002 | Mitchell et al. .......... | 525/329.9 |
| 6,392,116 B1 * | 5/2002 | Beihoffer et al. ............ | 604/372 |
| 6,555,502 B1 * | 4/2003 | Beihoffer et al. ............ | 604/368 |
| 6,849,665 B2 * | 2/2005 | Frenz et al. ................... | 521/64 |
| 2003/0069359 A1 | 4/2003 | Torii et al. | |

FOREIGN PATENT DOCUMENTS

| | | |
|---|---|---|
| EP | 0 493 011 | 7/1992 |
| EP | 0 509 708 | 10/1992 |
| WO | WO 95/22356 | 8/1995 |
| WO | WO 95/22358 | 8/1995 |
| WO | WO 97/12575 | 4/1997 |
| WO | WO 97/39780 | 10/1997 |
| WO | WO 99/25393 | 5/1999 |
| WO | WO 00/46260 | 8/2000 |
| WO | WO 01/56625 | 8/2001 |

* cited by examiner

*Primary Examiner*—H. T Le
(74) *Attorney, Agent, or Firm*—Marshall, Gerstein & Borun LLP

(57) ABSTRACT

The invention concerns superabsorbent particles with a shell, wherein said shell comprises a cationic polymer crosslinked by the addition of crosslinker and adhered to hydrogel-forming polymer obtainable by applying a coating solution, containing both a cationic polymer and crosslinker, to hydrogel-forming polymer having a residual water content of less than 10 w %, their production and use.

43 Claims, No Drawings

CROSSLINKED POLYAMINE COATING ON SUPERABSORBENT HYDROGELS

CROSS-REFERENCE TO RELATED APPLICATIONS

This is the U.S. national phase application of International Application No. PCT/EP02/12808, filed Nov. 15, 2002, which claims the benefit of U.S. provisional patent application Ser. No. 60/331,727, filed Nov. 21, 2001, and European patent application Serial No. 02001776.0, filed Jan. 25, 2002.

The present invention concerns (a) superabsorbent particles with a shell. Said superabsorbent particles comprise a hydrogel-forming polymer, and said shell comprises a cationic polymer crosslinked by the addition of crosslinker and adhered to said superabsorbent particles. The invention also relates to a method of making such a material.

The invention further relates (b) to composites and airlaids comprising such superabsorbent particles and the application of said composites and airlaids in hygienic products. Said hygienic products exhibit improved dry- and wet-integrity as well as improved permeability, acquisition behavior and rewet.

In one aspect of (a) the present invention concerns coated absorbent particles having improved absorbent property, i.e. having improved performance on CRC, PAI, PP, ratio AUL (0.01 psi) to AUL (0.90 psi), Gel bed permeability, and/or vortex time compared to superabsorbent particles without adhered cationic polymer shell or compared to state of the art superabsorbent particles.

In another aspect of (a) the present invention concerns coated absorbent particles having improved permeability. Said absorbent particles exhibit improved permeability without tendency to gel-blocking by unchanged high CRC.

In yet another aspect of (a) the present invention concerns coated absorbent fines. Said coated fines exhibit improved acquisition rates without tendency to gel-blocking. In detail, this aspect of the present invention concerns improved coated fines of particle sizes below 400 μm as well as their application for improved absorption of aqueous fluids, e.g. in hygienics, medical care, engineering and construction, in agriculture or as food packaging and storage and protective against fire.

In one aspect of (b) the present invention concerns composites comprising superabsorbent particles with a shell, preferably a crosslinked polyamine shell, exhibiting improved performance. In a particular aspect of (b) the present invention concerns airlaids comprising superabsorbent particles with crosslinked polyamine shell exhibiting improved performance. Composites or airlaids of this aspect of the present invention show an excellent acquisition behavior as well as high absorptive capacities and low rewets at the same time.

In another aspect of (b) the present invention concerns composites comprising superabsorbent particles with a shell, preferably a crosslinked polyamine shell, of high permeability by unchanged CRC. In a particular aspect of (b) the present invention concerns air-laids comprising superabsorbent particles with crosslinked polyamine shell of high permeability by unchanged CRC. Composites or air-laids of this aspect of the present invention show an improved permeability.

In yet another aspect of (b) the present invention concerns composites comprising hydrophilic absorbent fines with a shell, preferably a crosslinked polyamine shell. In a particular aspect of (b) the present invention concerns air-laids comprising hydrophilic absorbent fines with crosslinked polyamine shell. Composites or air-laids of this aspect of the present invention show an improved acquisition behavior and low rewets at the same time.

Said composites and said air-laids including more than 30% by weight, of said hydrophilic superabsorbent material. The combination of originally counter-current features as high CRC and excellent permeability by showing preferably no gel-blocking on the one hand, and short acquisition times and low rewets on the other hand allow the application of highest amounts of polyamine coated superabsorbent polymers in the new composites.

Composites or air-laids of the present invention have an excellent smooth feel in a relatively thin absorbent sheet material with unexpectedly high loading of superabsorbent polymers and can be manufactured without fiber or binder while providing excellent structural integrity with little to no shakeout or loss of superabsorbent particles from the sheet material.

Absorbent materials for use in personal care products for the absorption of body fluids are known in the art. Hydrogels (superabsorbent particles) are able to absorb large volumes of aqueous body fluids (at least about 15 g of 0.9%-NaCl-solution per 1 g hydrogel). Superabsorbent particles are polymers of unsaturated carboxylic acids or derivatives thereof. These polymers are rendered water-insoluble, but water-swellable by crosslinking them with conventional di- or polyfunctional monomer materials. These crosslinked polymers still comprise anionic charged carboxyl groups attached to the polymer backbone that enable the polymer to absorb aqueous body fluids.

Superabsorbent polymers are manufactured by known polymerization techniques, preferably by polymerization in aqueous solution by gel polymerization. The products of this process are aqueous polymer gels, which are reduced to small pieces by mechanical forces and dried afterwards using drying procedures and apparatus known in the art.

The drying process is followed by pulverization of the resulting polymer particles to the desired particle sizes. Inevitably the pulverization method leads also to particles having smaller sizes than desired (fines). Fines present in hydrogel-forming polymers reduce the absorptive capacity caused by the so-called gel-blocking.

Gel-blocking occurs when superabsorbent particles are wetted and the particles swell so as to inhibit fluid transmission to other superabsorbents or to other regions of the absorbent structure. Wetting of other regions takes place by a very slow diffusion process. As a consequence, acquisition of aqueous body fluids by the absorbent structure is much slower than the rate, at which the fluids are discharged, especially in gush situations. Leakage takes place, before the superabsorbent particles are fully saturated and the fluids reach the unwetted regions.

To improve the absorption profile, the superabsorbent particles need to be optimized in absorption capacity, absorption rate, acquisition time, gel strength, and/or permeability. This allows to reduce further amounts of cellulosic fiber.

It is known that superabsorbent particles with small particle sizes show fast acquisition times because of their higher surface area they are offering. Incorporation of fines into absorbent cores generally means very quick acquisition of aqueous fluids at the first application of aqueous solution and an excellent rewet after this first dosage, even by measuring the rewet value after 2 minutes and not—as it is usually done—after 10 minutes. The common problem of the use of fines is the second and the following applications of aqueous solution. Fines show for the second and the following applications higher acquisition times and also worse rewets.

One task of the present invention is to confirm the fines, which are just showing an excellent acquisition behavior because of their high surface area, into a product with an absorption profile, which doesn't allow characteristics as gelling or gel-blocking by wetting. It is desired, that the new product show high permeability and gel strength, as well as a high absorption capacity and low rewets at the same time.

Yet it is another task of the present invention to overcome the above problems concerning the absorption profile of superabsorbent particles in general over the whole particle size distribution, preferably from 150 µm up to 1000 µm. It is desired to offer hydrogel-forming polymers, which are not showing the disadvantages of the related art. The new products are desired to combine countercurrent features as high CRC and excellent permeability.

Yet it is a further task of the present invention to overcome the above problems concerning incorporating superabsorbent particles in highest amounts in personal care products. While the structures described in the literature have often proven beneficial, they have not completely solved the problems associated with the use of superabsorbent particles. Because of gel-blocking, the ratio of superabsorbent to fiber remains too low for the intended use of absorbing large quantities of body fluids. Furthermore, the problem of separation of the incorporated and not affixed particulates by wearing the personal care product remains. Up to now there is no proposed absorbent structure that overcome the problem of incorporation higher amounts of superabsorbent particles without changing the absorption profile.

In order to use higher quantities of superabsorbent particles within personal care products, the liquid permeability is an important factor which has to be considered. The permeability or flow conductivity of the hydrogel layer formed by swelling in the presence of body fluids is very important to overcome the problem of leakage. The lack of permeability directly impacts on the ability of resultant gel layers to acquire and distribute body fluids.

Water-absorbing resins, particularly superabsorbent polymers, have been in use in disposable, absorbent fibrous articles, such as diapers and bandages for many years. These superabsorbent polymers have been used together with a batt of absorbent fibers, such as cellulose fibers, used to absorb and hold the liquid within the product, and for faster liquid uptake during the slower absorption of the liquid by an adjacent superabsorbent polymer. The most common absorbent batt used in the diaper art is manufactured from fluffed wood pulp fibers, as disclosed in U.S. Pat. No. 2,788,003. A densified paper-like surface layer also has been used in conjunction with an absorbent batt to improve "wicking" of the liquid to the absorbent batt, as disclosed in U.S. Pat. Nos. 3,612,055 and 3,938,522.

Others have attempted to manufacture a continuous roll of woven or non-woven fibrous material that contains a high percentage, e.g., 50-80% by weight, of a particulate superabsorbent polymer, such as sodium polyacrylate. Examples of fibrous substrates impregnated with superabsorbent polymer are found in U.S. Pat. Nos. 5,614,269; 5,980,996; and 5,756,159 wherein a fibrous substrate is impregnated with the superabsorbent polymer by impregnation with the monomer and subsequent polymerization by contact with UV light for polymerization in situ while in contact with the fibrous substrate.

Other patents, including U.S. Pat. Nos. 5,607,550 and 5,997,690 teach the continuous manufacture of a fibrous substrate containing more than about 50% superabsorbent particles (50-60%) by the wet, papermaking process. The raw material, including fibers and superabsorbent particles, are mixed with high quantities of water, or other liquid medium capable of swelling the superabsorbent particles, and deposited onto a water-pervious support member, generally a Fourdinier wire, where much of the water is removed leaving a wet mass of fiber and superabsorbent polymer particles. The wet mat is transferred from the pervious support member and consolidated under heat and pressure to form the fibrous substrate having the superabsorbent particles distributed throughout. As disclosed in U.S. Pat. No. 5,997,690, sufficient absorbency performance requires at least about 50% by weight superabsorbent particles based on the total weight of the absorbent article. The most difficult problem encountered in attempting to continuously manufacture the sheet material containing a relatively high percentage of superabsorbent particles is in achieving structural integrity of the article both during and after manufacture without significant loss (shakeout) of superabsorbent particles.

Another principal process for continuously making a consolidated sheet of material is a "dry" process. In a dry process, filler material, such as cellulosic fibers, is coated with a resin binder in a gaseous stream, or by mechanical means. For example, the fibers supplied from a fiberizing apparatus (e.g., a pressurized refiner) may be coated with a thermosetting synthetic resin, such as a phenol-formaldehyde resin, in a blowline blending procedure, wherein the resin is blended with the fiber with the aid of air turbulence. Thereafter, the resin-coated fibers from the blowline are subjected to prepress drying, for example, in a tube-like dryer, and then are randomly formed into a mat by air conveying the fibers onto a support member (e.g., a forming wire). The formed mat, preferably having a moisture content of less than about 10 wt. %, is then pressed under heat and pressure in a press between a pair of heated platens to cure the thermosetting resin and to compress the mat into an integral consolidated structure. The consolidated structure may be embossed on an outer surface by texturing one of the press platens to achieve a desired embossed design in the outer surface of the product during consolidation.

Another process for continuously manufacturing a consolidated sheet of material is a wet-dry process, wherein resin-blended fiber from the blowline is mixed with water as the conveying medium and is formed into a mat as a wet slurry on a water-pervious support member where water is removed by mechanical means to a moisture content of about 60% or less. The formed mat then is mechanically conveyed through a multi-deck air dryer in which the moisture content is further reduced to about 10% or less. The mat is then pressed under heat and pressure similar to the above-described "dry" process.

Yet another important factor which has to be considered by incorporating superabsorbent particles in absorbent members besides the method of manufacturing is the wet integrity of the regions in the absorbent structure that contains the superabsorbent particles. Absorbent structures with good wet integrity showing sufficient integrity in a partially wet, and/or wetted state such that the physical continuity of the hydrogel formed after swelling is not substantially disrupted or altered under normal use conditions. During normal use, absorbent structures in absorbent articles are typically subjected to tensional and torsional forces like bouncing, stretching or twisting in the crotch area. If wet integrity is inadequate, these forces may cause a substantial alteration or disruption in the physical continuity of the hydrogel which leads to loss of permeability of the superabsorbent hydrogel zone, or the hydrogel particles will be shifted and drifted in such manner that leakage occurs.

A lot of work was done to immobilize superabsorbent particles in order to improve wet integrity. One possibility is the addition of large quantities of liquid polyhydroxy compounds that act as an adhesive to hold the particles together or attach the particles to a substrate; but during swelling, to some extent, the particles become detached from each other or from the substrate in the presence of excess liquid. Another way of immobilization describes the formation of an interparticle crosslinked aggregate, wherein the aggregate is joined to a carrier, which may be comprised of cellulosic fibers or which may be formed by a web. Unfortunately interparticle crosslinking will lead to loss of flexibility and therefore to unpleasant feeling by wearing the absorbent member. Further, interparticle crosslinked aggregates tend to lose water when stored for a larger period of time and thus the aggregates become stiff or brittle. Moreover, interparticle crosslinking is shifting the degree of crosslinking towards higher values, which leads to lower absorption capacities. More flexible absorbent structures are gained by adhesive attachment of superabsorbent particles to fibers. Unfortunately the adhesive attachment negatively influences the absorption profile of the particles and leads to nonuniform swelling.

In WO01/56625 an absorbent structure is proposed which contains an absorbent layer having a relatively high concentration of high-absorbency material but which absorbent structure is stable and affixed to a matrix and cannot be detached by mechanical forces. The new absorbent structure has a specific absorption capacity especially in regions, were in gush situations highest amounts of body fluids are applied.

Generally said web is loaded with superabsorbent material up to 60 or 70 w % compared to conventional personal care products. Said web offers high absorption capacities, but the permeability should be better for wetting the entire amount of superabsorbent material.

It is a further task of the present invention to provide a matrix wherein superabsorbent polymer is incorporated in amounts convenient to have an optimum in permeability and absorbency and which exhibits wet strength integrity. The absorbent structure has to be of high flexibility and thinness, which is therefore very comfortable in use, even in wearing the personal care products over a longtime period.

It is desired to have high absorption capacity superabsorbents in a diaper, wherein the absorbent core is preferably continuously manufactured for reasons mentioned above, but high capacity superabsorbents limits the permeability within the diaper. Consequently, the superabsorbent particles are higher crosslinked to improve permeability of the superabsorbent, which results in lower capacity superabsorbents. Superabsorbent material of extremely high crosslinking is proposed in WO 00/46260. Said material shows a Pressure Absorbency Index of less than 100 and a Vertical Absorption of not less than 12 g/g under a pressure of 1922.8 Pa. Particularly preferred are superabsorbents which additionally possess a Performance under Pressure of less than 23 g/g (0.7 psi) and/or an Absorbency Under Load of less than 27 g/g (2100 Pa). Superabsorbent particles of said invention exhibit excellent liquid acquisition, transportation and distribution properties but are strong limited in absorption capacity and rewet.

Polyamines are known to have improved adhesion to cellulose product (fluff), while polyamine coated superabsorbents have some improved permeability as measured in the bulk for lower capacity superabsorbent. Coating with uncrosslinked polyamines shows improved adhesion to fibers because of the high flexibility of polyamine molecules. But as being uncrosslinked, the polyamines are easily to extract by wetting with aqueous body fluids. Thus, the viscosity of the fluid to absorb will rise and the acquisition rate of the superabsorbent material slows down. On the other hand, if the polyamine is covalently bond to the superabsorbent, the degree of crosslinking of the superabsorbent particle will be higher and the absorptive capacity goes down. Moreover, covalent bonding occurs preferably at temperatures of higher than 150° C.; and at that temperatures obviously there are problems with yellowness of the product.

In literature there are a lot of patents concerning the addition of cationic compounds to improve permeability of superabsorbent particles and their immobilization after incorporation in personal care products. Most of the items found in literature are dealing with base polymer or commercial polymer, which is crosslinked and surface crosslinked to a content desirable for the incorporation in known composites or personal care products. Most of the patents leave the superabsorbent particles unchanged and coming up with procedures for applying cationic polymers or mixtures thereof with solvents onto substrate or said superabsorbents to form covalent bondings.

U.S. Pat. No. 5,883,158 (Kao Corp.) is dealing with a process with a plurality of steps within the process. At first, superabsorbent particles (base polymer or commercial polymer) have to be treated with water (water-retained SAP retaining 10 to 100 parts by weight of water per 100 parts by weight of SAP), followed by dispersing them in a solvent and addition of the polyfunctional compound having two or more reactive groups and selected from a hydrophilic polymer or a metallic compound in an amount of 0.005 to 5 parts by weight per 100 parts by weight of SAP. In a further step a crosslinker having two or more functional groups capable of reacting with the polyfunctional compound is added at a weight ratio of the polyfunctional compound to the crosslinker of 0.1 to 30. If the SAP retains less than 10 w % water the resulting products are not suitable as water absorbing polymers in hygienic applications and show a poor stability.

WO 95/22356 and U.S. Pat. No. 5,849,405 (Procter & Gamble) are claiming a method for obtaining absorbent material with at least one improved absorbent property (GBD<0.95, SFC at least $20 \times 10^{-7}$ $cm^3$sec/g, BBS at least 30 gf, CR at least 15%), comprising a mixture of SAP (base polymer and also commercial SAP) and an absorbent property modification polymer (e.g. cationic polymer), that is reactive with at least one component included in a urine (phosphate ion, sulfate ion, carbonate ion), wherein said mixture is made by applying a solution containing an organic solvent, water and said absorbent property modification polymer onto SAP. The weight ratio of organic solvent to water is at least 50:50.

WO 97/12575 (Procter & Gamble) also reports the addition of polycationic compound without further crosslinker.

WO 99/25393 describe multicomponent superabsorbent gel particles wherein the hydrogel forming component is neutralized between 0 and 25 mole-%.

U.S. Pat. No. 5,851,672 and U.S. Pat. No. 5,985,432 (Procter & Gamble) proposing the addition of a reactive hydrophilic compound having a function for modifying surface characteristics of superabsorbent particles. The reactive hydrophilic compound is chemically bonded to the superabsorbent particle. The proposed method is very expensive: (a) applying a first surface modification compound onto the surface of the SAP (b) swelling the absorbent polymer by absorbing water (c) removing a portion of the water while maintaining the swollen state, thereby forming a porous structure.

Other patents dealing with benefits from incorporation of polyamine coated superabsorbents (which are not crosslinked) in fibrous matrices, e.g. U.S. Pat. No. 5,641,561 (Weyerhaeuser), U.S. Pat. No. 5,382,610 and EP 0 493 011 (Nippon Shokubai), WO 97/39780 (Procter & Gamble) are claiming an absorbent material having improved structural stability in the dry and wet states, comprising water-insoluble absorbent hydrogel-forming polymer, a polycationic polymer bonded to the absorbent gelling particles at the surface thereof and glue microfibers that act as an adhesive between SAP and carrier layer. Said carrier layer is selected from woven or non-woven material, polycationic polymer selected from the group consisting of polyamines, polyimines and mixtures thereof (Claim 9).

Above patents describe however very special efforts for immobilization of polyamine coated SAP, which results in expensive procedures.

WO 95/22358 (Procter & Gamble) is dealing with an absorbent member containing absorbent material as described in WO 95/22356. U.S. Pat. No. 5,324,561 (Procter & Gamble) reports about SAP which is directly crosslinked amino-epichlorohydrin adducts (Kymene®).

Most of the above mentioned patents are dealing with the benefits in permeability from surface coating with polyamine compounds. But most of them are working without further crosslinking agent at higher temperatures, which results in interparticle bondings and/or covalent bondings of the cationic compound at the surface of the superabsorbent polymer particles. It is known to the inventors from a lot of experimental work, that each change in the degree of crosslinking at the surface or within the superabsorbent particles changes the absorption profile of the resulting polymer. Therefore, if commercial products are used, as done and claimed in above patents, a change of the absorptive capacity towards lower values by increasing the degree of crosslinking is found. Despite there is a increase of permeability and a lowering of gel-blocking in the resulting products, the change for the worse concerning the absorption capacity and the high efforts in process (a lot of different steps, additional compounds like plasticizer) negate the former benefits. Further interparticle crosslinking will lead to loss of flexibility and therefore to unpleasant feeling by wearing the absorbent member. Further, interparticle crosslinked aggregates tend to lose water when stored for a larger period of time and thus the aggregates become stiff or brittle. More flexible absorbent structures are gained by adhesive attachment of superabsorbent particles to fibers.

It is desired to create an absorbent structure having a relatively high concentration of superabsorbent material showing the benefits from surface coating with polyamine products in increase of permeability, but without changing the absorption profile of the former superabsorbent particles by additional crosslinkings. It is desired to provide an absorbent structure wherein superabsorbent polymer is incorporated in amounts convenient to have an optimum in permeability and absorbency and which exhibits wet strength integrity. The absorbent structure has to be of high flexibility and thinness, which is therefore very comfortable in use, even in wearing the personal care products over a longtime period.

Polycationic compounds are advantageously used because they form a strong ionic bond with an anionic absorbent polymer and retains strong adhesive forces after absorbing water and swelling with water. Said adhesive forces cause that the crosslinked cationic polymer is adhered to the superabsorbent polymer. It is desired to have preferably no covalent bonds between the cationic polymer and the superabsorbent polymer. Preferably there are only associations via intermolecular interactions such as electrostatic interaction, hydrogen bonding interaction and van der Waals interactions. Therefore, the presence of cationic polymer on the superabsorbent particles preferably will not influence the absorption profile of the superabsorbent polymer. In addition, polyamines are known to attach adhesively to fibrous substrate and cannot be extracted.

The desired absorbent structure has to be able of quickly absorbing body fluids applied thereto. It is further desired to provide an absorbent material which is incorporated in personal care products in highest amounts while maintaining the required absorptive capacity without showing gel blocking phenomena and therefore preventing leakage. It is further desired to make absorbent structures with immobilized superabsorbent material without further addition of compounds as glue fibers. The new superabsorbent material has to show high CRC and a permeability like highly crosslinked polymers, but has to have on the other hand high absorption capacities and excellent rewet values.

It is further desired to provide an absorbent structure which is easy to produce and therefore inexpensive in manufacturing.

Surprisingly it is found, that such a desired absorbent structure with combined features of high CRC and permeability on the one hand and high absorption capacities and excellent rewet on the other hand can be obtained by producing superabsorbent particles with a shell and applying said absorbent material to fibrous web. Said superabsorbent particles comprise of hydrogel-forming polymer, and said shell comprises a cationic polymer crosslinked by the addition of crosslinker and adhered to said superabsorbent particles. Other components may be included in the superabsorbent particles with a shell. The core thereof preferably consists of a hydrogel forming polymer. Preferably the shell consists essentially of a cationic polymer crosslinked by the addition of crosslinker, more preferably the shell consists only of a cationic polymer crosslinked by the addition of crosslinker. Cationic polymers are preferably polyamine or polyimine material, preferably polyamine. Cationic polymer are preferrably (a) polymers having primary amine groups; (b) polymers having secondary amine groups; (c) polymers having tertiary amine groups; and (d) mixtures thereof. The cationic polymer may also include quaternary amines as long as there are some crosslinkable groups (i.e. some primary, secondary and/or tertiary units). Examples are polyvinylamine, polyvinylimine, polyvinylguanidine or mixtures thereof. Preferred are polyvinylamine and polyvinylimine. Most preferred is polyvinylamine. According to the invention, both cationic polymer and crosslinker are added at the same time within one step or separately in two steps to said hydrogel-forming polymer. The resulting solution is called coating solution. It is important that the curing takes place after the addition of cationic polymer and crosslinker to prevent covalent bondings or gelling of the coating solution. Said cationic polymers are reacting preferred with said crosslinkers than reacting with free polymer endings of the superabsorbent polymer to form covalent bondings. Therefore it is possible to prepare crosslinked cationic polymers within one reaction step covering entirely the surface of the superabsorbent polymer only by adhesional forces. Examples for crosslinking agents reacting with cationic polymers are multifunctional acrylates, multifunctional esters, halohydrins, multifunctional halides, multifunctional isocyanates, transition metals like zinc. Preferred crosslinkers are selected from the group of sodium formate, poly (ethylene glycol) diglycidyl ethers. The optimal concentration of the crosslinking agent has to be adjusted depending on the activity for the agent and polycation. For polyamine and diepoxides the ranges is 0.25-4 mole percent, for sodium formate the range is between 50 and 150 mole percent. The crosslinked cationic polymer covering the surface of the superabsorbent polymer is called the shell. The shell covers most (more than 50%, preferred more than 80%, more preferred more than 90%, especially more than 95%, 96%, 97%, 98%, or 99%) of the surface, most preferred the entire surface. According to the invention, the number of covalent bondings between cationic polymers and superabsorbent particle are extremely low and in a especially preferred manner they are completely excluded. Superabsorbent particles with a shell concerns in this invention preferably particles of one core of hydrogen forming polymer within the shell, but by using fines of hydrogen forming polymer one or more fines may be included a shell. The core of the hydrogen forming polymer is not restricted with regard to shape, but concerns preferably particle sizes below 1000 μm in diameter. The hydrogel-forming polymer has a residual water content of less than 10 weight-% (w %), i.e. 9, 8, 7, 6, 5, 4, 3, 2, 1, or less w % water, preferred is a water content of less than 7 w %, more preferred less than 5 w %. The lower limit for the water content is preferred 1 w %, more preferred 2 w %.

In a preferred embodiment the base polymer is optimized by using specific crosslinkers as aluminates, silic acid alkali salt, silica and/or alumosilicates. Base polymer as used in this invention refers to hydrogel forming polymer which shows preferably no surface crosslinking and only some internal crosslinking. Base polymer shows preferably high CRC values of more than 15 g/g. The use of aluminate compounds of the formula $M_n[H_{2n+2}Al_nO_{3n+1}]$, in which M is potassium or sodium and n is a whole number between 1 and 10, for preparing mechanically stable ionically crosslinked hydrogels is described in WO99/55767. WO 00/31157 teaches the addition of a silicic acid alkali salt of the formula $M_2O \times n\ SiO_2$ to the polymerization reaction mixture. In said formula is M an alkali metal and n is a number between 0.5 and 4. WO01/68156 is reporting from the addition of alumosilicates to the polymerization reaction mixture.

In a further preferred embodiment the base polymer used in present invention shows no additional surface crosslinking. After the coating with polyamines, said base polymer shows the properties as a high crosslinked superabsorbent polymer, despite being low crosslinked. This enables the resulting product to absorb high amounts of body fluids and having low rewet at the same time. The absorption capacities of the new absorbent material are very high, and the acquisition behavior is excellent.

Thus, the present invention concerns (a) absorbent material consisting of superabsorbent particles with a shell, and (b) to composites comprising such an absorption material.

In one aspect of (a), the present invention concerns absorbent material comprising of absorbent particles with a shell exhibiting improved performance. The new superabsorbent particles show a CRC of at least 24 g/g and a Pressure Absorbency Index of less than 120. Furthermore the superabsorbent material according to the invention shows a ratio of AUL (0.01 psi) to AUL (0.90 psi) of more than 2.0, preferred of more than 2.5, especially preferred of more than 3.0 and most preferred of more than 3.5.

In another aspect of (a), the present invention concerns absorbent structures having improved permeability. Said structures of extremely high permeability can be obtained by polymers, which fulfil special criterias in CRC and Gel Bed Permeability. Thus, superabsorbent particles of extremely high permeability show a CRC of at least 18 g/g and a Gel Bed Permeability of more than 800.

In yet another aspect of (a), the present invention concerns superabsorbent fines with a crosslinked shell of cationic polymer, which do not have the disadvantages mentioned above. Said coated fines exhibit the same performance as superabsorbent material with normal particle size distribution even after repeated dosages and show additional the benefits in acquisition behavior and rewet at the first application of aqueous solution. Products with such an absorption profile are very interesting even for the incontinence problem, where in between a short time highest amounts of body fluids are applied.

Coated fines show high acquisition rates and excellent rewets, caused by the high surface area they are offering and their higher number of smaller particles, compared to conventional superabsorbents. The fluid transmission or permeability is improved. Using superabsorbent fines as base polymer, the new coated superabsorbent fines show no gel-blocking. Further the new products have the ability for trickling and are therefore very comfortable in handling. Therefore they are preferably used for applications in absorption of aqueous solutions e.g. in medical care, engineering and construction, in agriculture or as food packaging and storage and protective against fire.

Generally and independent of particle size, it is possible, to prepare superabsorbents which show improved performance by adhesively coating the superabsorbent polymer particle with a crosslinked surface of polyamine, and behave therefore as high crosslinked superabsorbents within the absorbent core, that is, the absorbent core shows excellent permeability and therefore excellent acquisition times, and at the same time the new superabsorbent particles exhibit high absorption capacities and improved rewet.

Further it has been surprisingly found, that manufacturing composites comprising superabsorbent particles with crosslinked polyamine-coated shell leads to absorbent structures of high permeability and absorption capacities as well as of improved acquisition behavior. Composites of the state of the art comprising on the one hand low crosslinked superabsorbent particles, which show excellent rewet, but exhibit—especially using higher concentrations of superabsorbents—high acquisition times, or on the other hand high crosslinked superabsorbent particles, which show good acquisition behavior, but high rewets, caused by their low absorption capacities.

Therefore, in one aspect of (b), the present invention concerns composites comprising superabsorbent particles with a shell. Said composites are able to combine features such as fast acquisition and excellent rewet. Therefore it is possible, to incorporate higher amounts of the new coated superabsorbent within the composite, without disadvantages in performance of the absorbent core. Thus according to the present invention, the composites containing more than 30% by weight, preferably more than 40% by weight, especially preferred more than 50% by weight and most preferred more than 60% by weight superabsorbent particles with crosslinked polyamine shell. Composites made thereof exhibit an excellent dry- and wet-integrity.

Said absorbent composite comprises a relatively high concentration of high-absorbency material uniformly distributed to hold the whole amounts of discharged body fluids but which absorbent structure is stable and affixed to a matrix and cannot be detached by mechanical forces.

Surprisingly it has been further found, that manufacturing air-laids as a continuous sheet on a conventional papermaking apparatus, it is possible to incorporate more than 30% by weight, preferably more than 40% by weight, more preferred more than 50%, especially preferred more than 60%, higher preferred more than 70% and most preferred more than 80% by weight superabsorbent particles, and less than 70% by weight, preferably less than 60% by weight, more preferred less than 50% by weight, especially preferred less than 40%, higher preferred less than 30% by weight and most preferred less than 20% by weight of other fibers, adhesives, or fillers, such as cellulosic or wood fluff fibers, thermoplastic fibers, adhesives, fillers, and other additives. The new sheet materials can be manufactured having new and unexpected structural integrity with little or no shakeout or loss of superabsorbent particles during or after manufacture.

Therefore, in another aspect of (b), the present invention concerns air-laids containing the above polyamine coated superabsorbent material exhibiting exceptional water absorption and retention properties. In addition, the sheet materials have an ability to absorb liquids quickly, demonstrate good fluid permeability and conductivity into and through the superabsorbent particles, and have a high gel strength such that the hydrogel formed from the superabsorbent particles, upon hydration, resists deformation under an applied stress or pressure, when used alone or in a mixture with other water-absorbing resins. Air-laids made thereof exhibit an excellent dry- and wet-integrity.

It is possible to produce air-laids comprising highest amounts of superabsorbent particles with crosslinked polyamine-coated shell.

In a preferred embodiment of the present invention, it has been found that heating a resin for a sufficient time at a sufficient temperature above the Tg (glass transition temperature) of the resin improves the absorption properties of the resin.

In accordance with one important embodiment of the present invention, it has been found that when a layer of the polyamine coated superabsorbent particles is heated to at least about 50° C. during sheet material manufacture (e.g., by a heated pressure roll or oven), not only are the absorption properties improved, but the particles are strongly adhered to any fiber or filler contained in the sheet material so that there is little to no loss of superabsorbent particles during manufacture and handling. Thus, a sheet material having less than 40% by weight non-SAP fiber, and without added adhesive, has new and unexpected structural integrity, for the above-described uses, particularly diaper cores.

The formation of absorbent members from said absorbent composites enables a production of improved skin feel personal care products.

The improved products show good absorbency, good strength and high flexibility and thinness. The improved products exhibit excellent permeability by unchanged absorption profile. Absorbent members containing the inventive composites exhibit highest absorption rate and absorption capacity without tendency to gelblocking.

A. The invention is directed to superabsorbent particles with a shell. Said superabsorbent particles comprise of hydrogel-forming polymer, and said shell comprises of a cationic polymer crosslinked by the addition of crosslinker and adhered to said superabsorbent particles. The hydrogel-forming polymer particles are coated preferably with about 0.01% to about 5% by weight of the cationic polymer, preferably with about 0.2% to about 4% by weight of the cationic polymer, most preferred 0.75 to 1.25 w %, i.e. 0.8, 0.85, 0.9, 0.95, 1.0, 1.05, 1.1, 1.15, 1.2 w %. The hydrogel-forming polymer has a residual water content of less than 10 w % at the time of the application of the shell.

In a preferred embodiment of the present invention the base polymers are crosslinked with aluminate, silicic acid alkali salt or alumosilicate compounds.

The invention also is directed to a method of making superabsorbent particles with a shell, characterized in that it comprises:
(a) preparing a solution containing water, optionally a wetting agent, a cationic polymer and a crosslinker (b) applying an amount of said solution onto a plurality of absorbent hydrogel-forming polymer particles with a residual water content of less than 10 w %
(c) drying said coated polymer particles at temperatures of no more than 150° C.

Preferably to a method for making superabsorbent particles with a shell wherein the wetting agent is a hydrophilic organic solvent, wherein the ratio of organic solvent to water in the reaction mixture is less than 50:50, more preferably to a method for making superabsorbent particles with a shell wherein the wetting agent is an alcohol, as e.g. propylene glycol and to superabsorber particles with a shell prepared by said methods.

The invention also is directed to a method of making an absorbent core of an absorption material comprising such superabsorbent particles. Said hygienic products exhibit improved acquisition rates.

A.1. In the first aspect of (A) the present invention is directed to above mentioned superabsorbent particles showing a CRC of at least 24 g/g, i.e. at least 24.5, 25 or 25.5 g/g, preferred of at least 26 g/g, i.e. at least 26.5, 27 or 27.5 g/g, especially preferred of at least 28 g/g, i.e. at least 28.5, 29 or 29.5 g/g, and most preferred of at least 30 g/g, i.e. at least 30.5, 31, 32, 33, 34, 35, 36, 37, 38, 39, 40 g/g or more. The superabsorbent particles show preferably a Pressure Absorbency Index PAI of less than 120 or less than 115, 110, or 105, preferred of less than 100, or less than 95, 90, 85, or 80 or even less. In a preferred embodiment the superabsorbent particles show a combination of the preferred CRC and PAI values. The superabsorbent particles show preferred a ratio of AUL (0.01 psi) to AUL (0.90 psi) of more than 2.0, i.e. 2.1, 2.2, 2.3, 2.4, preferred of more than 2.5, i.e. 2.6, 2.7, 2.8, 2.9, especially preferred of more than 3.0, i.e. 3.1, 3.2, 3.3, 3.4, and most preferred of more than 3.5, i.e. 3.6, 3.7, 3.8, 3.9, 4.0 and even more. More preferred is a combination of the AUL ratio with the above given values of CRC and/or PAI.

A.2. In the second aspect of (A) the present invention is directed to above mentioned superabsorbent particles show extremely high permeability. Said superabsorbent particles of high permeability are obtained using polymers with CRC of at least 18 g/g, preferably of at least 20 g/g, especially preferred of at least 22 g/g or the above mentioned CRC values and a Gel Bed Permeability of more than 800, i.e 810, 820, 830, 840, 850, 860, 870, 880, 890, 900, 910, 920, 930, 940, 950, 960, 970, 980, 990, preferably of more than 1000, i.e. 1010, 1020, 1030, 1040, 1050, 1060, 1070, 1080, 1090, 1100, 1110, 1120, 1130, 1140, 1150, 1160, 1170, 1180, 1190, more preferred of more than 1200, i.e. 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, especially preferred of more than 1500 i.e. 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990 and most preferred of more than 2000. More preferred is a combination of the permeability with the above given values of AUL and/or PAI.

A.3. The third aspect of (A) of the present invention is directed to superabsorbent particles with a shell made from hydrogel-forming polymer fines, called within the invention sometimes just superabsorbent fines. This new superabsorbent fines show a Vortex Time of less than 30 s. 80% of said superabsorbent fines have particle sizes of smaller than 400 μm. The invention further provides the application of such new superabsorbent fines e.g. in medical care, engineering and construction, in agriculture or as food packaging, storage and protective against fire. Said coated fines exhibit improved acquisition rates.

In a preferred embodiment of the third aspect of (A), the new superabsorbent fines show a
Vortex Time of less than 25 s,
preferred of less than 20 s,
especially preferred of less than 15 s,
and most preferred of less than 10 s,
and/or a particle size distribution, wherein
80% are smaller than 400 μm, 90% are smaller than 400 μm, 95% are smaller than 400 μm,
preferred 80% are smaller than 300 μm, 90% are smaller than 300 μm, 95% are smaller than 300 μm,
especially preferred 80% are smaller than 250 μm, 90% are smaller than 250 μm, 95% are smaller than 250 μm
and most preferred 80% are smaller than 200 μm, 90% are smaller than 200 μm, 95% are smaller than 200 μm.

B. The new above mentioned superabsorbent particles of independent particle sizes are preferably used in an absorbent core. The invention is therefore also directed to an absorbent core comprising such an absorption material. The following aspects of the invention are given to elucidate the invention, but should not be used to limit the scope of the invention.

B.1. In the first aspect of (B), the invention is directed to composites from superabsorbent particles with a shell, preferably a crosslinked polyamine shell, exhibiting improved performance. Said composites including more than 30% by weight, of superabsorbent particles with crosslinked polyamine shell. Said superabsorbent particles showing a CRC of at least 24 g/g, preferred of at least 26 g/g, especially preferred of at least 28 g/g and most preferred of at least 30 g/g and additional a Pressure Absorbency Index PAI of less than 120, preferred of less than 100.

In a preferred embodiment the superabsorbent particles for the intended use in a composite show a CRC of at least 24 g/g, preferably of at least 26 g/g, especially preferred of at least 28 g/g and most preferred of at least 30 g/g and additional a Pressure Absorbency Index of less than 120, preferred of less than 100 and at the same time a ratio of AUL (0.01 psi) to AUL (0.90 psi) of more than 2.0, preferred of more than 2.5, especially preferred of more than 3.0 and most preferred of more than 3.5.

The composites containing more than 30% by weight, preferably more than 40% by weight, especially preferred more than 50% by weight and most preferred more than 60% by weight of superabsorbent particles with a shell, preferably a crosslinked polyamine shell, exhibiting a high CRC.

In a preferred embodiment of the first aspect of (B) the invention is directed to air-laids from said superabsorbent particles with a shell, preferably a crosslinked polyamine shell, exhibiting improved performance. Said air-laids are sheet materials including more than 30% by weight of superabsorbent particles with crosslinked polyamine shell exhibiting a high CRC.

According to the present invention, the air-laids containing more than 30% by weight, preferably more than 40% by weight, more preferred more than 50% especially preferred more than 60%, higher preferred more than 70% and most preferred more than 80% by weight of superabsorbent particles with a shell, preferably a crosslinked polyamine shell, exhibiting a high CRC.

B.2. In the second aspect of (B), the invention is directed to composites from above mentioned superabsorbent particles with a shell, preferably a crosslinked polyamine shell, exhibiting high permeability. Said composites including more than 30% by weight, of superabsorbent particles with a shell. Said superabsorbent particles of high permeability are selected from coated superabsorbents with CRC of at least 18 g/g, preferably of at least 20 g/g, especially preferred of at least 22 g/g and a Gel Bed Permeability of more than 800, preferably of more than 1000, more preferred of more than 1200, especially preferred of more than 1500 and most preferred of more than 2000. The composites are used for example as absorbent core in personal care products.

The composites containing more than 30% by weight, preferably more than 40% by weight, especially preferred more than 50% by weight and most preferred more than 60% by weight of superabsorbent particles with a shell, preferably a crosslinked polyamine shell, exhibiting high permeability.

In a preferred embodiment of the second aspect of (B) the invention is directed to air-laids from superabsorbent particles with a shell, preferably a crosslinked polyamine shell, exhibiting high permeability. Said air-laids are sheet materials including more than 30% by weight of superabsorbent particles with a shell exhibiting high permeability.

According to the present invention, the air-laids containing more than 30% by weight, preferably more than 40% by weight, more preferred more than 50% by weight, especially preferred more than 60% by weight, higher preferred more than 70% by weight and most preferred more than 80% by weight of superabsorbent particles with a shell exhibiting high permeability.

B.3. In the third aspect of (B), the invention is directed to composites from above mentioned hydrophilic superabsorbent fines with a shell, preferably a crosslinked polyamine shell, with improved acquisition rates. Said composites including more than 30% by weight, of hydrophilic superabsorbent fines with a shell. Said superabsorbent fines show a Vortex Time of less than 30 s. 80% of said superabsorbent fines have particle sizes of smaller than 400 μm.

In a preferred embodiment said superabsorbent fines for the intended use in a composite show a
Vortex Time of less than 25 s,
preferred of less than 20 s,
especially preferred of less than 15 s,
and most preferred of less than 10 s,
and a particle size distribution, wherein
80% are smaller than 400 μm, 90% are smaller than 400 μm, 95% are smaller than 400 μm,
preferred 80% are smaller than 300 μm, 90% are smaller than 300 μm, 95% are smaller than 300 μm,
especially preferred 80% are smaller than 250 μm, 90% are smaller than 250 μm 95% are smaller than 250 μm
and most preferred 80% are smaller than 200 μm, 90% are smaller than 200 μm, 95% are smaller than 200 μm.

The composites containing more than 30% by weight, preferably more than 40% by weight, especially preferred more than 50% by weight and most preferred more than 60% by weight of hydrophilic superabsorbent fines with a shell.

In a preferred embodiment of the third aspect of (B) the invention is directed to air-laids from hydrophilic superabsorbent fines with a shell, preferably with a crosslinked polyamine shell. Said air-laids are sheet materials including more than 30% by weight of hydrophilic superabsorbent fines with a shell.

According to the present invention, the air-laids containing more than 30% by weight, preferably more than 40% by weight, more preferred more than 50% especially preferred more than 60%, higher preferred more than 70% and most preferred more than 80% by weight of hydrophilic superabsorbent fines with a shell.

In a preferred embodiment of the present invention composites or air-laids containing superabsorbent particles with a shell, preferably with a crosslinked polyamine shell, that show a Performance Parameter PP (=Rewet-Number×Acquisition Time) of less than 1500, or less than 1450, 1400, 1350, 1300, 1250, 1200, 1150, 1100, 1150, preferred of less than 1000, or less than 950, 900, 850, 800, 750, 700, 650, 600, 550, and especially preferred of less than 500.

The invention also relates to the application of said composites or air-laids as absorbent cores on the hygienic sector. Said hygienic products exhibit improved dry- and wet-integrity as well as improved permeability, acquisition behavior and rewet. The composites of the present invention have an excellent smooth feel in a relatively thin absorbent structure with unexpectedly high loadings of superabsorbent polymers and can be manufactured without glue fiber or binder while providing excellent structural integrity with little to no shake-out or loss of superabsorbent particles from the composite.

The present invention further provides the application of said coated hydrogel-forming particles as absorption core in personal care products. Said hygienic products exhibit improved acquisition rates. The inventive superabsorbent particles with a shell show compared to particles without a shell an improvement of acquisition rate on the secondary, tertiary and quaternary insult of more than 10%, preferred more than 50%, more preferred more than 100% and more, if compared with such state of the art particles with similar CRC and or SFC.

Superabsorbent Particles

Superabsorbent polymer particles are lightly crosslinked polymers capable of absorbing several times their own weight in water and/or saline. Superabsorbent polymer particles can be made by any conventional process for preparing superabsorbent polymers and are well known to those skilled in the art. Suitable process for preparing superabsorbent polymer particles include the processes described in U.S. Pat. Nos. 4,076,663; 4,286,082; 4,654,039 and 5,145,906 which describe the solution polymerization method and U.S. Pat. Nos. 4,340,706; 4,497,930; 4,666,975; 4,507,438 and 4,683,274 which describe the inverse suspension polymerization method, the disclosures of which are hereby incorporated by reference.

Superabsorbent polymer particles useful in the present invention are prepared form one or more monoethylenically, unsaturated, water soluble carboxyl or carboxylic acid anhydride containing monomers and the alkali metal and ammonium salts thereof wherein said monomers comprise 50 to 99.9 mole percent of said polymer. Exemplary monomers include acrylic acid, methacrylic acid, maleic acid, fumaric acid, maleic anhydride and the sodium, potassium and ammonium salts thereof. The preferred monomer is acrylic acid.

a) Superabsorbent Forming Monomer

Superabsorbent forming monomer, as used herein, referred to polymerizable compounds which contribute to the absorbency of the polymers formed therefrom. Suitable superabsorbent forming monomers useful in the present invention include monoethylenically unsaturated compounds (or compounds having a polymerizable double bond), having at least one hydrophilic radical, such as carboxyl, carboxylic acid anhydride, carboxylic acid salt, sulfonic acid, sulfonic acid salt, hydroxyl, ether, amide, amino or quaternary ammonium salt groups. Examples of suitable superabsorbent forming monomers are as follows:

1. Carboxyl group-containing monomers: monoethylenically unsaturated mono- or polycarboxylic acids, such as (meth)acrylic acid (meaning acrylic acid or methacrylic acid. Similar notations are used hereinafter), maleic acid, fumaric acid; crotonic acid, sorbic acid, itaconic acid, and cinnamic acid.
2. Carboxylic acid anhydride group-containing monomers: monoethylenically unsaturated polycarboxylic acid anhydrides (such as maleic anhydride);
3. Carboxylic acid salt-containing monomers: water-soluble salts (alkali metal salts, ammonium salts, amine salts, etc.) of monoethylenically unsaturated mono- or polycarboxylic acids [such as sodium (meth)acrylate, trimethylamine (meth)acrylate, triethanolamine(meth)acrylate, sodium maleate, methylamine maleate];
4. Sulfonic acid group-containing monomers: aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl (meth) acrylate, 2-hydroxy-3-(meth)acryloxy propyl sulfonic acid];
5. Sulfonic acid salt group-containing monomers: alkali metal salts, ammonium salts, amine salts of sulfonic acid group-containing monomers as mentioned above.
6. Hydroxyl group-containing monomers: monoethylenically unsaturated alcohols [such as (meth)allyl alcohol], monoethylenically unsaturated ethers or esters of polyols (alkylene glycols, glycerol, polyoxyalkylene polyols), such as hydroxyethyl (meth)acrylate, hydroxypropyl (meth)acrylate, triethylene glycol (meth)acrylate, poly (oxyethylene oxypropylene) glycol mono (meth)allyl ether (in which hydroxyl groups may be etherified or esterified).
7. Amide group-containing monomers: vinylformamide, (meth)acrylamide, N-alkyl (meth)acrylamides (such as N-methylacrylamide, N-hexylacrylamide), N,N-dialkyl (meth)acrylamides (such as N,N-dimethylacrylamide, N,N-di-n-propylacrylamide), N-hydroxyalkyl (meth)acrylamides [such as N-methylol(meth)acrylamide, N-hydroxyethyl(meth)acrylamide], N,N-dihydroxyalkyl (meth)acrylamides [such as N,N-dihydroxyethyl(meth) acrylamide], vinyl lactams (such as N-vinylpyrrolidone);
8. Amino group-containing monomers: amino group-containing esters (e.g. dialkylaminoalkyl esters, dihydroxyalkylaminoalkyl esters, morpholinoalkyl esters, etc.) of monoethylenically unsaturated mono- or dicarboxylic acid [such as dimethylaminoethyl (meth)acrylate, diethylaminoethyl (meth)acrylate, morpholinoethyl (meth)acrylate, dimethylaminoethyl fumarate], heterocyclic vinyl compounds [such as vinyl pyridines (e.g. 2-vinyl pyridine, 4-vinyl pyridine, N-vinyl pyridine), N-vinyl imidazol]; and
9. Quaternary ammonium salt group-containing monomers: N,N,N-trialkyl-N-(meth)acryloyloxyalkylammonium salts [such as N,N,N-trimethyl-N-(meth)acryloyloxyethylammonium chloride, N,N,N-triethyl-N-(meth)acryloyloxyethylammonium chloride, 2-hydroxy-3-(meth)acryloyloxypropyl trimethyl ammonium chloride], and monomers as mentioned in British patent specification No. 1,034,296.

Suitable monomers which become water-soluble by hydrolysis, for use in this invention instead of or in conjunction with the water-soluble monomers, include monoethylenically unsaturated compounds having at least one hydrolyzable group, such as esters, amide and nitrile groups. Such monomers having an ester group include for example, lower alkyl ($C_1$-$C_4$) esters of monoethylenically unsaturated carboxylic acids, such as methyl (meth)acrylate, ethyl (meth)acrylate and 2-ethylhexyl (meth)acrylate; and esters of monoethylenically unsaturated alcohols [vinyl esters, (meth)-allyl ester, etc.], such as vinyl acetate and (meth)allyl acetate. Suitable nitrile group-containing monomers include (meth)acrylonitrile.

Among these monomers having a polymerizable double bond which are water-soluble or become water-soluble by hydrolysis, water-soluble monomers which do not need hydrolysis after polymerization are preferred from the viewpoint of providing an easy process for producing water-absorbing resins. Further, from the viewpoint of providing water-absorbing resins having higher water-absorbance, the preferred water-soluble monomers are carboxyl group-containing monomers such as (meth)-acrylic acid and maleic acid anhydride; carboxyl acid salt group-containing monomers such as sodium (meth)acrylate, trimethylamine (meth)acrylate and triethanolamine (meth)acrylate, and quaternary ammonium salt group-containing monomers such as N,N,N-trimethyl-N-(meth)acryloyloxyethylammonium chloride. Most preferred superabsorbent forming monomers in the present invention include, for example, acrylic acid, methacrylic acid, maleic acid, fumaric acid, crotonic acid, sorbic acid, itaconic acid, cinnamic acid, vinyl sulfonic acid, allyl sulfonic acid, vinyl toluene sulfonic acid, styrene sulfonic acid, sulfo(meth)acrylate, sulfopropyl(meth)acrylate, 2-acrylamid-2-methylpropane sulfonic acid, 2-hydroxyethyl (meth)acryloylphosphate, phenyl-2-acryloyloxyethylphosphate, the sodium, potassium and ammonium salts thereof, maleic anhydride and combinations thereof. It is also preferred that the superabsorbent forming monomer in the sprayable blend is at least partially neutralized, preferably neutralized to a level of from 1 to 100 mole percent, more preferably from 10 to 80 mole percent, and most preferably from 15 to 75 mole percent. Most preferably, the superabsorbent forming monomer is neutralized acrylic acid.

Hydrogel-forming polymers are preferably polymers from (co)polymerized hydrophilic monomers, grafted (co)polymers of one or more hydrophilic monomers onto suitable basic compounds, crosslinked cellulosic- or starch-ethers, crosslinked carboxymethylcellulose, partial crosslinked polyalkyleneoxide or water absorbing natural compound as for example guar derivatives, carrageenan and alginates.

Basic compounds for grafting can be of synthetic or natural origin. Examples are starch, cellulose and derivatives thereof, polysaccharides and oligosaccharides, polyvinylalcohol, polyalkylene oxides (preferred polyethylene oxide, polypropylene oxide), polyamines, polyamides, hydrophilic polyesters, galactomannans, guar derivatives and alginates.

Preferred copolymer materials for use as superabsorbent hydrogel-forming material possess acidic functional groups (e.g. carboxylic groups). Most of them are present in form of their salts (e.g. alkali- or ammonium salts), because of their excellent swelling behavior in presence of water.

Suitable monomers and (co)monomers are those listed above. Preferred are polymerizable, unsaturated, acid-containing monomers. Such monomers include the olefinically unsaturated acids and anhydrides that contain at least one carbon to carbon olefinic double bond. Preferably these monomers can be selected from olefinically unsaturated carboxylic acids and acid anhydrides, olefinically unsaturated sulfonic and phosphonic acids, and mixtures thereof.

Examples for olefinically unsaturated carboxylic acid and carboxylic acid anhydride monomers are monoethylenically unsaturated $C_3$- to $C_{25}$-carboxylic acids or anhydrides as acrylic acid, methacrylic acid, ethacrylic acid, α-chloroacrylic acid, α-cyanoacrylic acid, β-methacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, maleic acid, maleic acid anhydride, itaconic acid, citraconic acid, mesaconic acid, glutaconic acid, aconitic acid, fumaric acid, tricarboxyethylene and maleic acid anhydride.

Examples for olefinically unsaturated sulfonic acid and phosphonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, styrene sulfonic acid, 2-hydroxy-3-acryloxypropyl sulfonic acid, 2-hydroxy-3-methacryloxypropyl sulfonic acid, 2-acrylamide-2-methylpropane sulfonic acid; vinylphosphonic acid, allylphosphonic acid and mixtures thereof.

Preferred monomers are acrylic acid, methacrylic acid, vinylsulfonic acid, 2-acrylamide-2-methylpropane sulfonic acid and mixtures thereof, such as mixtures of acrylic acid and methacrylic acid, mixtures of acrylic acid and 2-acrylamide-2-methylpropane sulfonic acid or mixtures of acrylic acid and vinylsulfonic acid.

For improvement of the absorption profile it may be better to add monoethylenically unsaturated non-acid monomers which are able to form copolymers from mixtures with the foregoing mentioned acidic monomers. Those are for example amides or nitriles of monoethylenically unsaturated carboxylic acids such as acrylamide, methacrylamide, N-vinylformamide, N-vinylacetamide, N-methyl-vinylacetamide, acrylonitrile, methacrylonitrile. Further vinylester of saturated $C_1$- to $C_4$-carboxylic acids such as vinylformiate, vinylacetate, vinylpropionate; alkyl vinylether compounds with at least 2 C-atoms within the alkyl-group such as ethyl vinylether, butyl vinylether; esters of monoethylenically unsaturated $C_3$- to $C_6$-carboxylic acids such as esters from primary $C_1$- to $C_{18}$-alcohols and acrylic acid, methacrylic acid or maleic acid, half esters of maleic acid such as maleic acid monomethyl ester, N-vinyllactams such as N-vinylpyrrolidone or N-vinylcaprolactam, acrylic acid- or methacrylic acid esters of alkoxylated primary saturated alcohol such as alcohol with 10 to 25 C-atoms which are reacted with 2 to 200 mol ethylene oxide and/or propylene oxide per mole alcohol, monoacrylic acid esters and monomethacrylic acid esters of polyethylene glycol or polypropylene glycol up to molecular weights of 2000. Further monomers are styrene and alkylsubstituted styrene compounds such as ethylstyrene or tert.-butylstyrene.

The non-acid monomers are present in said mixtures in contents from 0 to 50 w %, preferably lower than 20 w %.

In an especially preferred embodiment (co)polymers and/or graft (co)polymers from acrylic acid and maleic anhydride are used. Preferred are non-crosslinked water soluble or water dispersible polymers with molecular weights from 1 200 up to 250 000 g/mole. Possible comonomers are all monomers which can polymerise with acrylic acid and/or maleic acid.

Grafted copolymers include hydrolized starch-acrylonitrile graft copolymers, partially neutralized hydrolized starch-acrylonitrile graft copolymers, starch-acrylic acid graft copolymers, partially neutralized starch-acrylic acid graft copolymers, saponified vinyl acetate-acrylic ester copolymers, hydrolized acrylonitrile or acrylamide copolymers. These polymers may be used either independently or in the form of a mixture of two or more monomers, compounds or the like.

b) Crosslinking Compounds

Monoethylenically, unsaturated monomers are polymerized in the presence of an internal crosslinking compound to provide a lightly crosslinked base polymer wherein the crosslinking is substantially uniform throughout the polymer particles. These internal crosslinkers are well known in the art. Suitable crosslinkers are those compounds having two or more groups capable of reacting with the monoethylenically unsaturated monomers and which are at least partially water soluble or water dispersible, or at least partially soluble or dispersible in an aqueous monomer mixture. The internal crosslinking compound may be selected form a polyunsaturated monomer such as divinylbenzene, a compound having at least two functional groups which are reactive with the monoethylenically unsaturated monomer such as ethylendiamine, a compound having at least one unsaturated bond and at least one reactive functional group such as glycidyl acrylate.

Preferred crosslinkers are described in WO01/68156 which is incorporated by reference. Especially preferred are: tetraallyloxyethane, N,N'-methylene bisacrylamide, N,N'-methylene bismethacrylamide, triallylamine, trimethylol propane triacrylate, glycerol propoxy triacrylate, divinylbenzene, N-methylol acrylamide, N-methylol methacrylamide, glycidyl methacrylate, polyethylene polyamines, ethyl diamine, ethyl glycol, glycerin and the like. Preferred internal crosslinking monomers are those containing at least two allyl groups, most preferably three or four allyl groups. Preferred internal crosslinkers are tetraallyloxyethane and triallyl ether of pentaerythritol. The amount of internal crosslinker employed in the invention will depend on the internal crosslinker and the polymerization method. Generally the amount of internal crosslinker will vary from about 0.005 to about 1.0 mole percent based on moles of ethylenically unsaturated monomer.

Optional components used in the preparation of the superabsorbent polymer particles are water soluble hydroxy group containing polymers, such as polysaccharides and vinyl or acrylic polymers. Examples of water soluble polysaccharides are starches, water soluble celluloses and polygalactomannans. Suitable starches include the natural starches, such as sweet potato starch, potato starch, wheat starch, corn starch, rice starch, tapioca starch and the like. Processed or modified starches, such as dialdehyde starch, alkyl-etherified starch, allyl-etherified starch, oxyalkylated starch, aminoethyl-etherified starch, and cyanomethyl-etherified starch are also suitable. Polyvinyl alcohol and polyvinyl alcohol copolymers are also suitable.

The water-soluble celluloses useful in this invention are those obtained from such sources as wood, stems, bast, seed fluffs and the like which are then derivatiated to form hydroxyalkyl cellulose, carboxymethyl cellulose, methyl cellulose and the like.

Suitable polygalactomannans are guar gum and locust bean gums as well as their hydroxyalkyl, carboxyalkyl, and aminoalkyl derivatives. Water soluble vinyl and acrylic polymers include polyvinyl alcohol and poly(hydroxyethyl acrylate). The preferred polysaccharide for use in this invention is natural starch, such as wheat starch, corn starch and alpha starches. These optional preformed hydroxy containing polymers may be used in an amount from about 1 to 15 percent, preferably about 1 to 10 percent, most preferably about 1 to 5 percent.

In a preferred embodiment the base polymer is optimized by using aluminates, silica and/or alumosilicates as crosslinkers. Mechanically stable ionic crosslinked hydrogels are prepared using aluminate crosslinkers of the formula $M_n[H_{2n+2}Al_nO_{3n+1}]$, in which M is potassium or sodium and n is a whole number between 1 and 10. Further the addition of a silicic acid alkali salt of the formula $M_2O \times n\ SiO_2$ to the polymerization reaction mixture leads to preferred base polymers. In said formula M is an alkali metal and n is a number between 0.5 and 4. Also known is the addition of alumosilicates to the polymerization reaction mixture. Said crosslinkers are described in WO 00/31157, WO 99/55767 and WO01/68156. Said patents are incorporated herein by reference.

c) Polymerization

The superabsorbent polymer particles useful in the present invention may be prepared by well known polymerization methods. The polymerization reaction is conducted by subjecting the aqueous reaction mixture to any conventional form of polymerization activation irradiation. Radioactive, electronic, ultraviolet or electromagnetic radiation are alternative conventional polymerization techniques. Further the polymerization reaction is conducted in the presence of free radical initiator, redox initiators and thermal initiators. The redox initiators are combining oxidizing compounds with reducing agents. Redox initiators can be used as the primary initiator with the thermal polymerization initiators being used if desired to reduce the free monomer content of the final polymerization product below 0.1 percent by weight. Optionally, thermal initiators or redox initiators may be used as the sole initiator system. Examples of different initiator systems are found in U.S. Pat. No. 4,497,930 which discloses a two component initiator system comprising a persulfate and a hydroperoxide and U.S. Pat. No. 5,145,906 which discloses a three component initiator system; i.e. redox system plus thermal initiator. Preferred initiators are written in WO01/68156 which is incorporated by reference. Especially preferred is the polymerization reaction conducted by photoinitiation.

Any of the well known water soluble reducing agents and oxidizing agent can be used in this invention as the redox initiator. Examples of reducing agents include such compounds as ascorbic acid, alkali metal sulfites, alkali metal bisulfites, ammonium sulfite, ammonium bisulfite, alkali metal hydrogen sulfite, ammonium hydrogen sulfite, ferrous metal salts, e.g. ferrous sulfates, sugars, aldehydes, primary and secondary alcohols, and the like.

Oxidizing agents include such compounds as hydrogen peroxide, caprylyl peroxide, benzoyl peroxide, cumene peroxide, tertiary butyl diperphthalate, tertiary butyl perbenzoate, sodium percarbonate, sodium peracetate, alkali metal persulfates, ammonium persulfates, alkylhydroperoxides, peresters, diacryl peroxides, silver salts, and the like. A particularly preferred redox initiator pair is ascorbic acid and hydrogen peroxide. The reducing agent is used in an amount of about $2 \times 10^{-5}$ to about $2 \times 10^{-2}$ mole percent based on moles of acrylic acid.

In order to ensure complete polymerization of the unsaturated monomer and the crosslinking monomer, a thermal initiator can be included in the polymerization process. Useful thermal initiators are the "azo" initiators, i.e. compounds which contain the —N=N— structure. Any of the azo compounds which have solubility in water or in a monomer-water mixture and which have an 10 hour half life at 30° C. or above can be used. Examples of useful azo initiators are 2,2'-azobis (amidino) propane dihydrochloride, 4,4'-azobis(cyanovaleric acid), 4,4'-butylazo-cyanovaleric acid, 2,2'-azobis(isobutyronitrile), 2,2'-azobis(2-(2-imidazole-2-yl))propane dihydrochloride, and the like. Other thermal initiators include the persulfates and hydroperoxides when used in the absence of a reducing agent, e.g. sodium, potassium and ammonium persulfates, t-butylhydroperoxide and the like. A preferred azo initiator for use in this invention is 2,2'-azobis(amidino) propane dihydrochloride. The thermal initiators are used in the amount of 0 to about 1 mole percent based on the weight of unsaturated monomer.

In the case of photoinitiated polymerization, the polymerization is started with photoinitiators. Non-limiting examples for photoinitiators are α-decomposing compounds, H-abstracting systems as well as azides. Non-limiting examples for said systems are benzophenone-derivatives as Michler/s ketone, phenanthrene-derivatives, flourene-derivatives, anthrachinone-derivatives, thioxantone-derivatives, cumarin-derivatives, benzoin ethers and derivatives thereof, azo compounds as systems which are building radicals mentioned above, substituted hexaaryl-bisimidazoles or acylphosphinoxides. Non-limiting examples for azids are 2-(N,N-dimethylamino)-ethyl-4-azidocinnamate, 2-(N,N-dimethylamino)-ethyl-4-azidonaphthylketone, 2-(N,N-dimethylamino)-ethyl-4-azidobenzoate, 5-azido-1-naphthyl-2'-(N,N-dimethylamino)-ethylsulfone, N-(4-sulfonylazidophenyl)-maleinimide, N-acetyl-4-sulfonylazidoaniline, 4-sulfonylazidoaniline, 4-azidoaniline, 4-azidophenacylbromide, p-azidobenzoeic acid, 2,6-bis(p-azidobenzylidene)-cyclohexanone and 2,6-bis(p-azidobenzylidene)-4-methyl cyclohexanone. Photoiniators are used in amounts of 0.01 to 5% by weight based on the monomer content.

The superabsorbent polymer may be prepared by the solution or the inverse suspension polymerization method or any suitable bulk polymerization method. The solution polymerization and inverse polymerization methods are well known in the art; see for example U.S. Pat. Nos. 4,076,663; 4,286,082; 4,654,039 and 5,145,906 which describe the solution polymerization method and U.S. Pat. Nos. 4,340,706; 4,497,930; 4,666,975; 4,507,438 and 4,683,274 which describe the inverse suspension polymerization method. The teachings of these patents are hereby incorporated by reference.

In the solution polymerization method, the water soluble monomer is polymerized at a monomer concentration from about 5 to about 70 percent in aqueous solution at a temperature from about 5° C. to about 150° C. depending upon the polymerization initiator system. A detailed description of the solution polymerization method is given in U.S. Pat. No. 5,145,906; the teachings of which are hereby incorporated by reference.

In the inverse suspension polymerization process, the unsaturated monomer in an aqueous solution (about 35 to 60 percent monomer to 65 to 40 percent water) is dispersed in an alicyclic or aliphatic hydrocarbon suspension medium in the presence of a dispersing agent, such as a surfactant or protective colloid such as polyvinyl alcohol. A surfactant having a HLB value of 8 to 12 such as a sorbitan fatty acid ester may be employed as the dispersing agent. The inverse suspension polymerization method is described in detail in U.S. Pat. No. 4,340,706; the teachings of which are hereby incorporated by reference.

Preferred is the polymerization in aqueous solution, the so-called "gelpolymerisation". In this process, 10 to 70 w % monomers in water are polymerised. The technical process is written in Chapter 3 in "Modern Superabsorbent Polymer Technology", F. L. Buchholz and A. T. Graham, Wiley-VCH, 1998. The polymerization is conducted between 0° C. and 150° C., preferred between 10° C. and 100° C. under normal or reduced or highered pressure. It is also possible, to polymerize under nitrogen.

The carboxylic acid groups or the unsaturated monomer used in the polymerization may be neutralized prior to or subsequent to the polymerization. Suitable neutralizing agents include an alkali such as sodium hydroxide, ammonium hydroxide, potassium hydroxide or the like, and the appropriate degree of neutralization is 50-98 mole percent; preferably 60-75 mole percent. The degree of neutralization is preferably at least 50 mole percent.

Cationic Polymers

Suitable cationic material are polymers with amine- and/or imine-groups, which are rendered insoluble by crosslinking. Preferred are polymers, copolymers and grafted (co)polymers of vinylamine of ethylene imine, which can be used in a modified manner by polymer analogue reactions.

Polyvinylamines are obtained by polymer analogue reactions, e.g. hydrolizing poly-N-vinylamides (as for example poly-N-vinylformamides, poly-N-vinylacetamides), hydrolizing poly-N-vinylimides (as for example poly-N-vinylsuccinimides, poly-N-vinylphthalimides), degradation of polyacrylamide under reaction with basic hypochlorite. Polyvinylamines are preferably prepared by polymerization of N-vinylformamide and subsequent polymer analogue reaction as described in DE-A-3 128 478. The N-vinylformamide-groups of the polymers can be hydrolized to vinylamine-groups. For example, polyvinylamine can be obtained by completely hydrolizing the homopolymers of N-vinylformamide. Most preferred is hydrolysis by basic compounds. With this method, it is possible to reach a degree of hydrolysis in the range of 5 to 95%. Especially preferred are products showing degrees of hydrolysis between 70 and 100%; most preferred are completely hydrolized products. The degree of hydrolysis can be determined by enzymatical determination of formate or by polyelectrolyte-titration of amines with potassium poly-vinylsulfate-solution.

Further copolymers of vinylamines can be used, as for example copolymers of vinylformamide and comonomers, which can be changed to copolymers of vinylamines by polymer analogue reactions as described above. Comonomers are all monomers which are able to copolymerize with vinylformamide. Nonlimiting examples are: acryl amide, methacryl amide, methacrylonitrile, vinylacetate, vinylpropionate, styrene, ethylene, propylene, N-vinylpyrrolidone, N-vinylcaprolactam, N-vinylimidazole, monomers containing sulfon- or phosphonate-groups, vinylglycol, acrylamido(methacrylamido)alkylene-trialkylammoniumsalt, diallyle-dialkylammoniumsalt, ($C_1$-$C_4$)-alkylvinylethers as methylvinylether, ethylvinylether, isopropylvinylether, n-propylvinylether, t-butylvinylether, n-substituted alkyl(meth)acrylamides substituted by a ($C_1$-$C_4$)-alkylgroup as for example N-methylacryl amide, N-isopropyl acrylamide, and N,N-dimethyl acrylamide, further ($C_1$-$C_{20}$)-alkylmethacrylic acid esters as methacrylate, ethylmethacrylate, propyl acrylate, butyl acrylate, hydroxyethyl acrylate, hydroxyethyl methacrylate, hydroxypropyl acrylate, hydroxypropyl methacrylate, hydroxybutyl acrylate, hydroxybutyl methacrylate, 2-methylbutyl acrylate, 3-methylbutyl acrylate, 3-pentyl acrylate, neopentyl acrylate, 2-methylpentyl acrylate, hexyl acrylate, cyclohexyl acrylate, 2-ethylhexyl acrylate, phenyl acrylate, heptyl acrylate, benzylacrylate, toluene acrylate, octyl acrylate, 2-octyl acrylate, nonyl acrylate and octyl methacrylate.

Some specific copolymers are written for example in DE-A-3 534 273: copolymers of N-vinylformamide and vinylacetate, vinylpropionate, ($C_1$-$C_4$)-alkylvinylethers, methacrylic acid- and acrylic acidester, acrylonitrile and acrylamide and homologues thereof and vinylpyrrolidone.

Nonlimiting examples of grafted polymers are polymers from alkyleneoxide-groups and N-vinylformamide as written in DE-A-1 951 5943, which were crosslinked after hydrolysation. Further examples for polymers useful for grafting are polyvinylacetate and/or polyvinylalcohol. As written in DE-A-19 526 626 grafting with N-vinylformamide onto said polymers by free radical polymerization is possible and the resultant polymer can be hydrolised, rendered to un-neutralized form and crosslinked afterwards.

Other suitable polymers for grafting with N-vinylformamide are vinylacetate, acrylic acid, methacrylic acid, acrylamide and acrylonitrile.

Other suitable polymers for grafting with N-vinylformamide are mono-, oligo- or polysaccharide-based polymers, which contain N-vinylformamide in contents from 20 to 95% by weight, related to the entire amount monomer+polymer. Said grafted polymers are rendered afterwards in free amines by hydrolyzation, rendered in case to un-neutralized form followed by crosslinking.

Grafted polymers are preferably prepared from N-vinylformamide as the only monomer. However, it is possible to replace N-vinylformamide partially by comonomers mentioned above.

Further it is possible, to modify polyvinylamine, copolymers and grafted (co)polymers thereof by polymer analogue reactions. Said reactions are manifold and described for example in "Advanced Organic Chemistry" from Jerry March, $3^{rd}$ reprint, John Wiley and sons 1985.

Beside these intramolecular, polymer analogue reactions of polyvinylamines a lot of other reactions are possible. Nonlimiting examples of said reactions are amidizing, alkylizing, preparation of sulfonamides, urea, thiourea, carbamate, acylizing reactions with acids, lactones, acid anhydrides and acid chlorides. Polymers obtained by said reactions are also suitable for the preparation of crosslinked cationic polymers. Preferably said polymer analogue reactions are carried out before crosslinking the polyvinylamines and copolymers and grafted (co)polymers thereof.

Other suitable polymers are polyethylene-imines, polyamidoamines grafted with ethylene-imine or polyamines grafted with ethylene-imine.

WO-A-94/12560 teaches a further class of aminogroups-, preferably ethylene-imine-groups-containing polymers. Said polymers are water-soluble, crosslinked, partially amidified polyethylene-imines, which are available by reaction of polyethylene-imines with one-basic carboxylic groups or esters, anhydrides, acid chlorides or acid amides thereof to an amide, and reaction of amidified polyethylene-imines with crosslinkers containing at least to functional groups.

The values of the molecular mass can reach up to 5 million. Preferably the molecular mass is in between 1000 to 1 million. The polyethylene-imines will be partially amidified with one-basic carboxylic acids in that way that, as non-limiting example, 0.1 to 90, preferably 1 to 50% of the amidifiable nitrogen-atoms of the polyethylene-imines are present as amide-group. Suitable crosslinkers are mentioned above. Preferably crosslinkers free of halogen are chosen.

The reaction between compounds containing aminogroups and crosslinkers are carried out using 0.1 to 50, preferably 1 to 5 parts by weight of crosslinker per 1 part by weight of the aminogroup containing compound.

Other addition products containing aminogroups are polyethylene-imines as well as quaternary polyethylene-imines.

The polyethylene-imines and quaternary polyethylene-imines can be brought into reaction with crosslinkers containing at least to functional groups. Quaternisation of polyethylene-imines can be carried out for example with alkyl halogens as methylchloride, ethylchloride, hexylchloride, benzylchloride or laurylchloride as well as with dimethylsulfate.

Further suitable polymers are alkoxylated polyethylene-imines, obtained as non-limiting example by reaction of polyethylene-imine with ethylene oxide and/or propylene oxide. The alkoxylated polyethylene-imines can be brought into reaction with crosslinkers containing at least to functional groups and thus rendered water-insoluble. The alkoxylated polyethylene-imines containing per each NH-group 0.1 to 100, preferably 1 to 3 alkylene oxide units. The values of the molecular mass of said polyethylene imines can reach up to 2 million. Preferably chosen molecular masses of polyethylene imines for alkoxylation are in between 1000 to 50000. Further suitable polymers containing water-soluble aminogroups are reaction products of polyethylene-imines with diketenes, as for example polyethylene-imines with molecular masses from 1000 to 50 000 with distearyl-diketene, which are crosslinked afterwards.

Crosslinked polyethylene-imines are for example described in EP 0 895 521.

Polyethylene-imine is obtained in conventional manner by cationic polymerization of ethylenimine in the presence of polymerization catalysts, as for example acids, Lewis-acids, acid salts of metals. Preferably used polyethylene-imines show molecular weights from 1000 to 5 million.

Especially preferred cationic polymers are polyvinylamine, polyethyleneimine, polyalkylamine, polyvinylguanidine and in case modified polyvinylamines and modified polyethyleneimines.

Most preferred cationic polymers are polyvinylamine and polyethyleneimine.

Crosslinkers for Crosslinking the Cationic Polymers

Suitable crosslinkers for crosslinking said cationic polymers are bi- or polyfunctional, that is, they are possessing two ore more active groups which are able to react with the amino- or imino-groups of the polymers. Besides compounds of low molecular weight it is possible to carry out the crosslinking reaction with polymers and/or copolymers.

Suitable Bi- or Polyfunctional Crosslinkers are as Nonlimiting Examples (a) Di- or polyglycidylcompounds
(b) Di- or polyhalogen compounds
(c) Compounds with two or more isocyanate-groups, which can be blocked
(d) Polyaziridine compounds
(e) Derivatives of dihydroxyketone
(f) Compounds with two or more activated double bonds, which can carry out Michael-additions
(g) Sodium formate
(h) Di- and polyaldehydes and Di- and polyketones.

Preferred crosslinkers (a) are as nonlimiting examples bis-chlorohydrinethers of polyalkylene-glycols, as written in U.S. Pat. No. 4,144,123. Further preferred are phosphonic acid diglycidyl ether and ethyleneglycol diglycidyl ether.

Further crosslinkers are reaction products of at least trihydric alcohols with epichlorhydrin to form products containing at least two chlorohydrin-units. That is, generally used as polyhydric alcohols are for example glycerin, ethoxylated glycerin or propoxylated glycerin, polyglycerin with 2 to 15 glycerin-units per molecule, as well as ethoxylated or propoxylated polyglycerin. Said crosslinkers are proposed in DE-A-2 916 356.

Suitable crosslinkers (b) are α, w- or vicinal dichloroalkanes, as for example 1,2-dichloroethane, 1,2-dichloropropane, 1,2-dichlorobutane and 1,6-dichlorohexane.

Further α, w-dichloropolyalkyleneglycols are known as crosslinkers from EP-A.0 025 515 with preferably 1 to 100 ethylenoxide-units.

Further crosslinkers (c) containing blocked isocyanategroups, as for example trimethylhexamethylene-diisocyanate blocked with 2,2,6,6,-tetramethylpiperidine-4-on. Such crosslinkers are known as for example from DE-A-4 028 285.

Further preferred are crosslinkers containing aziridinegroups (d) based on polyethers or substituted hydrocarbons, as for example 1,6-bis-N-aziridinomethane. Parts of this category of crosslinkers are further at least reaction products of dicarboxylic acid esters with ethylene imine containing two aziridino-groups as well as mixtures of said crosslinkers.

Crosslinkers free of halogen (d) are products of the reaction of dicarboxylic acid esters (completely esterified with one functional alcohol with 1 to 5 carbon atoms) with ethylene imine. Suitable dicarboxylic acid esters are for example oxalic acid dimethylester, oxalic acid diethylester, succinic acid dimethylester, succinic acid diethylester, adipic acid dimethyl ester, adipic acid diethyl ester and glutaric acid dimethyl ester. Thus it is possible to get bis-[β-(1-aziridino) ethyl]oxalic acid amide from the reaction of diethyloxylate with ethylene imine. The dicarboxylic acid esters are reacting with ethylene imines in a molar ratio of 1 to at least 4. The reactive groups of this crosslinkers are the aziridino-groups at the end of the molecules. Those crosslinkers are characterized as nonlimiting example by the following formula:

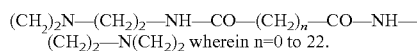

(CH$_2$)$_2$N—(CH$_2$)$_2$—NH—CO—(CH$_2$)$_n$—CO—NH—(CH$_2$)$_2$—N(CH$_2$)$_2$ wherein n=0 to 22.

Crosslinkers of (e) are as nonlimiting examples ethylene carbonate, propylene carbonate, urea, thiourea, guanidine, dicyanamide or 2-oxazolidinone and derivatives thereof. Preferred are propylene carbonate, urea and guanidine.

Crosslinkers of (f) are products of the reaction of polyether diamines, alkylene diamines, polyalkylene polyamines, alkylene glycols, polyalkylene glycols or mixtures thereof with monoethylenically unsaturated carboxylic acids, esters, amides or anhydrides of monoethylenically unsaturated carboxylic acids, where said reaction products containing at least two ethylenically unsaturated double bondings, carboxylic acid amide-, carboxylic- or estergroups, as well as methylenebis-acrylamide and divinylsulfone.

Crosslinkers of (f) are as nonlimiting examples products of the reaction of polyetherdiamines with preferably 2 to 50 alkyleneoxide units, alkylenediamines as for example ethylenediamine, propylenediamine, 1,4-diaminobutane and 1,6-diaminohexane, polyalkylenepolyamines with molecular weights of less than 5000, as for example diethylenetriamine, triethylenetetramine, dipropylenetriamine, tripropylenetetramine, dihexamethylenetriamine and aminopropylethylenediamine, alkyleneglycols, polyalkyleneglycols or mixtures thereof with monoethylenically unsaturated carboxylic acids
esters of monoethylenically unsaturated carboxylic acids
amides of monoethylenically unsaturated carboxylic acids and
anhydrides of monoethylenically unsaturated carboxylic acids.

Said reaction products and their manufacturing are described in EP-A-873 371 and are expressionally mentioned hereby.

Especially preferred crosslinkers are products of the reaction of maleic acid anhydride with α, w-polyetherdiamines of a molecular mass from 400 to 5000, the reaction products of polyethyleneimines of a molecular mass from 129 to 50 000 with maleic acid anhydride, as well as the reaction products of ethylenediamine or triethylenetetramine with maleic acid anhydride in a molecular ratio of 1 to at least 2.

Crosslinkers of (f) are preferably compounds of the following formula:

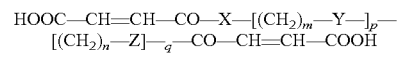

HOOC—CH═CH—CO—X—[(CH$_2$)$_m$—Y—]$_p$—[(CH$_2$)$_n$—Z]—$_q$—CO—CH═CH—COOH wherein X, Y, Z=O, NH and Y additionally expresses CH$_2$ m, n=0-4 p, q=0-45 000 which can be obtained as reaction products of polyetherdiamines ethylenediamine or polyalkylenepolyamines with maleic acid anhydride.

Suitable crosslinkers free of halogen of (h) are as nonlimitating examples dialdehydes or their half- or acetal-compounds as precursor. Examples are: glyoxal, methylglyoxal, malonic dialdehyde, succinic dialdehyde, malenic- and fumaric acid dialdehyde, tartaric acid dialdehyde, adipic acid dialdehyde, 2-oxo-adipic acid dialdehyde, furane-2,5-dipropionaldehyde, 2-formyl-2,3-dihydropyrane, glutardialdehyde, pimeline acid aldehyde, as well as aromatic dialdehydes as for example terephthalic acid dialdehyde, o-phthalic acid dialdehyde, pyridine-2,6-dialdehyde or phenylglyoxal. Suitable compounds are also homo- or copolymers of acrolein or methacrolein with molecular mass of 114 to about 10 000. Suitable comonomers are water-soluble monomers as for example acrylamide, vinylacetate and acrylic acid. Further crosslinkers are aldehyde-starches.

Suitable crosslinkers free of halogen of (h) are as nonlimitating examples diketones or their half- or ketal-compounds as precursor.

Examples are: β-diketone as acetylacetone or cycloalkane-1,n-dione as cyclopentane-1,3-dione and cyclohexane-1,4-dione. Suitable compounds are also homo- or copolymers of methylvinylketone with molecular mass of 140 to about 15000. Suitable comonomers are water-soluble monomers as for example acrylamide and vinylacetate.

Of course, it is possible to use mixtures of two or more crosslinkers.

Especially preferred are crosslinkers without any halogen. The most preferred crosslinkers are sodium formate or ethylenglycoldiglycidylether.

The crosslinkers mentioned above are used alone or as mixture with water-soluble, amino-group-containing polymers or polyalkylenpolyamines.

Most preferred are crosslinkers react completely or preferred with aminogroups of the cationic material in that way, that no covalent bondings of the crosslinked polyamine layer to superabsorbent material occurs.

Method of coating a hydrogel-forming polymer with a coating solution that contains both an amine and crosslinker.

Conventional non-surface treated hydrogel-forming polymer particles used as base polymer according to the present invention are typically substantially dry. The term "substantially dry" means that the particles have a liquid content, typically water or other solution content, of less than about 10%, preferably less than about 8%, and most preferred less than about 6%. In general, the liquid content of the coated superabsorbent particles is in the range of from about 0.01% to about 5% by weight of the particles. Water contents of more than 10% are undesired, because the penetration of the coating solution in the case of base polymers with water contents of more than 10% will be too strong, and crosslinking of the polyamine compounds only at the surface of the superabsorbent particles cannot be guaranteed.

Said base polymer is contacted while mixing with a coating solution containing a polyamine (polyvinylamine, polyallylamine, or polyethyleneimine) and a crosslinking agent (sodium formate, polyepoxies, diesters, etc.) in water and (optionally) a wetting agent that is a hydrophilic organic solvent, preferably an alcohol such as propylene glycol. The weight ratio of organic solvent to water is preferably lower than 50:50. The application of the coating solution onto the surface of the base polymer can be achieved by addition of both the polyamine solution and crosslinking agent as one solution, or by addition of polyamine and crosslinker separately, but at the same time or alternatively sequentially.

The coating solution is applied to the base polymer particles in a manner such that the solution is uniformly distributed on the surface of the base polymer particle. Any of the known methods for dispersing a liquid can be used; preferably by dispersing the coating solution into fine droplets; e.g. by use of a pressurized nozzle or a rotating disc. Uniform coating of the base polymer can be achieved in a high intensity mechanical mixer or a fluidized mixture which suspends the base polymer in a turbulent gas stream. Methods for the dispersion of a liquid onto the superabsorbent base polymer's surface are known in the art; see for example U.S. Pat. No. 4,734,478; the teachings of which are hereby incorporated by reference; in particular column 6, line 45 to column 7, line 35.

The resulting particles are then dried and cured at about 100 _C for sufficient time to cure the coating. The resulting product is the broken up if agglomeration has taken place and resized.

There are several methods to perform polyamine-coating.

Polyamine and crosslinker are added simultaneously. Both components are mixed in a short time before application. Said mixture is applied via one nozzle.

Polyamine and crosslinker are added simultaneously. Both components are preferably applied via two separate nozzles to avoid crosslinking before application to the surface of superabsorbent material because of the high reactivity of the crosslinker.

Step-by-step addition of the components: at first the addition of crosslinker, followed by the addition of cationic polymer (preferably the polyamine). This method requires experimental conditions (e.g. very low reaction temperatures) to avoid covalent bondings of the crosslinker to the superabsorbent surface, if crosslinkers of high reactivity are chosen.

Step-by-step addition of the components: at first the addition of cationic polymer (preferably the polyamine), followed by the addition of crosslinker.

It is important, to perform the reaction temperatures after the application of both components (crosslinker and cationic polymer). The temperature has to be less than 150° C. to avoid yellowness of the product and covalent bondings between carboxylic groups of superabsorbent material and the amino-groups of the cationic polymer.

Additional Modifications

Further it is possible, to modify the cationic polymer by the addition of polyvalent ionic compounds.

Suitable ionic compounds are solutions of salts containing two- or more valencies. Non-limiting examples for said metal ions are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$, and $Au^{+/3+}$. Preferred are $Mg^{2+}$, $Ca^{2+}$, $Al^{3+}$, $Ti^{4+}$, $Zr^{4+}$ and $La^{3+}$, and especially preferred are $Al^{3+}$, $Ti^{4+}$ and $Zr^{4+}$ or mixtures thereof. Suitable metal ions are soluble to a convenient content in the applied solvent.

Most preferred are salts of metals with anionic groups tending to form weak complexes as for example chloride, nitrate and sulfate. Suitable solvents are water, alcohols, DMF, DMSO as well as mixtures thereof. Especially preferred solvents are water and mixtures of water/alcohol as for example water/methanol or water/1,2-propandiol. Said metal salts are applied using the convenient solution or dispersion of metal salt and solvent. This is done by any of various techniques and apparatus used for applying solutions to materials including coating, dumping, pouring, spraying, or immersing. Preferably it is done by spraying the solution or dispersion onto dry coated superabsorbent. Drying afterwards takes place using temperatures of no more than 100° C. for reasons explained later.

Furtheron, anionic compounds can be added. Nonlimiting examples are sulfate-, carbonate- or phosphate-ions.

Ionic compounds can be added at the same time or afterwards the polyamine coating. Even cationic polymer and/or anionic compound and/or polyamine and/or crosslinking system can be added simultaneously. The only restriction is that the crosslinking of the polyamine has to be guaranteed and e.g. no complexing reaction by added ionic compounds takes place before crosslinking is finished.

Another possibility of modification is the addition of acids. Nonlimiting examples of acids which can be added are HCl, $H_2SO_4$, $H_3PO_4$, $CH_3COOH$ etc. Using this method it is possible to adjust the degree of neutralisation of the cationic polymer and to lower the pH of the polymer to the desired pH-value.

It is possible to change the charge density of the polyamines. For example, polyvinylamine shows in completely protonated configuration a charge of 23 meq.

A further possibility of modification is the addition of adhesives, such as water-soluble or water-sensitive adhesives, latex adhesives, microfiber glues, hot melt adhesives (e.g. elastic hot melt adhesives) or solvent-based adhesives or the like. The addition of adhesives may support the adhesion of superabsorbent particles onto fibrous materials.

Yet another possible modification is treating the coated superabsorbent particles with plasticizer to render structures or composites made thereof more flexible. Suitable plasticizers include water, alone or in combination with humectants/coplasticizers as for example glycerol. In the case of water alone, the absorbent structure can be placed e.g. in a high humidity environment.

A further possibility of modification is the addition of surfactants. It is possible, to use all nonionic, anionic, cationic and amphoteric surfactants, preference being given to those, which are soluble or at least dispersible in water.

Examples of suitable nonionic surfactants are the adducts of ethylene oxide, propylene oxide or ethylene oxide/propylene oxide mixtures with alkylphenols, aliphatic alcohols, carboxylic acids or amines. Suitable examples are ($C_8$-$C_{24}$)-alkylphenols alkoxylated with ethylene oxide and/or propylene oxide. Other examples of suitable nonionic surfactants are ethoxylated ($C_{10}$-$C_{24}$)-fatty alcohols, ethoxylated ($C_{10}$-$C_{24}$)-fatty amines and ethoxylated ($C_{10}$-$C_{24}$)-fatty acids as well as ethoxylated ($C_{10}$-$C_{24}$)-fatty acid amides. Also suitable are polyhydric ($C_3$-$C_6$)-alcohols esterified partially with ($C_{10}$-$C_{24}$)-fatty acids. These esters can additionally be reacted with from 2 to 20 mol of ethylene oxide. Examples of suitable fatty alcohols which are alkoxylated to prepare the surfactants are palmityl alcohol, stearyl alcohol, myristyl alcohol, lauryl alcohol, oxo alcohols, and also unsaturated alcohols such as oleyl alcohol. Examples of ($C_3$-$C_6$)-alcohols, which are partially esterified and, if desired, ethoxylated, are glycerol, sorbitol, mannitol and pentaerythritol.

These polyhydric alcohols are partially esterified with ($C_{10}$-$C_{24}$)-fatty acids, e.g. oleic acid, stearic acid or palmitic acid. Esterification with the fatty acids goes only so far as to leave at least one OH group of the polyhydric alcohol unesterified. Examples of suitable esterification products are sorbitan monooleate, sorbitan tristearate, mannitol monooleate, glycerol monooleate and glycerol dioleate. The abovementioned fatty acid esters of polyhydric alcohols which still contain at least one free OH group can be reacted for further modification with ethylene oxide, propylene oxide or mixtures of ethylene oxide and propylene oxide.

Another group of suitable surfactants comprises homopolymers of ethylene oxide, block copolymers of ethylene oxide and alkylene oxides, and also polyfunctional block copolymers which are formed, for example by sequential addition of propylene oxide and ethylene oxide onto diamines.

The nonionic surfactants can be used alone or in a mixture with one another.

Suitable anionic surfactants are ($C_8$-$C_{24}$)-alkylsulfonates, which are preferably used in form of their alkali metal salts, ($C_8$-$C_{24}$)-alkyl sulfates, which are preferably used in form of their alkali metal or trialkanolammonium salts (e.g. trialkanolammonium lauryl sulfate, sulfosuccinic di- or monoesters), ($C_8$-$C_{24}$)-alkyl aryl sulfonic acids, and the sulfuric acid half-esters of adducts of ethylene oxide with alkylphenols or fatty alcohols.

Suitable cationic surfactants are e.g. the salts of fatty amines, quaternary fatty acid amino esters, quaternary fatty acid aminoamides, adducts of alkylene oxides with fatty amines or salts of fatty amines, and also long chain alkylbenzyldimethylammonium compounds.

Suitable amphoteric surfactants are e.g. dimethylcarboxymethyl-fatty acid alkylamidoammonium betaines, or 3-(3-fatty acid amido propyl) dimethylammonium 2-hydroxypropanesulfonate.

The ionic surfactants can be used alone or in a mixture with one another.

The abovementioned compounds are applied as powder, or an aqueous solution, or in a form dissolved or dispersed in a mixture solvent of water with a hydrophilic solvent such as ethanol or in a form allowed to react or to be adhered to the polyamine coated superabsorbent particles. Thus, there is no preferred method of application. The abovementioned compounds may be added in form of a powder, or may be sprayed in a liquid form which is made by dissolving or dispersing it in a suitable solvent. Said solvent will be removed later on e.g. by drying. A preferable method is such as mixing the water absorbent particles with said modification compound, e.g. by using a device such as a high speed agitating mixer, an air mixer, a tumbling mixer, and bundary mixer. Otherwise, the superabsorbent particles are also immersed in a solution or dispersion of the modification agent, or either be mixed with liquid drops, or mixed in a mist type formed by spraying the solution.

The mentioned surfactants can also be applied during the step of surface crosslinking. In this case, the coating solution will be applied in a performed distribution, and the coating will be completely covering the surface of the polymer particles.

Absorption Profile of Polyamine Coated Hydrogel-Forming Polymer

A. Polyamine coated superabsorbent polymer particles show improved performance.

Generally superabsorbent hydrogel-forming polymer particles with Pressure Absorbency Index PAI of less than 120, preferably of less than 110, more preferably of less than 100 show some advantages compared to superabsorbent polymer material with PAI of more than 120.

Absorbent cores built from superabsorbent material with Pressure Absorbency Index PAI of less than 120 show a much better permeability than the convential ones. Another advantage is the performance of polymer particles with PAI<120 in personal care products. Said particles show improved acquisition times and lower rewets. Furthermore they show excellent absorption capacities.

After coating with polyamines, the hydrogel-forming polymer particles absorb body fluids with highest acquisition rates and having low rewet at the same time. No gel-blocking is observed.

Generally, by adhesively coating the superabsorbent particles with a crosslinked surface of polyamine, it is possible, to prepare superabsorbents with improved performance, which behave as high crosslinked superabsorbents within the absorbent core, that is, the absorbent core shows excellent permeability and therefore excellent aquisition times, and at the same time the new superabsorbent particles exhibit improved rewet.

In a preferred embodiment, said absorption profile will further be improved by use of base polymers crosslinked with aluminate, silicic acid alkali salt or alumosilicate compounds. Said crosslinkers leads to optimized base polymers.

Moreover, polyamine coated hydrogel-forming polymer particles are characterized by a ratio of AUL (0.01 psi) to AUL (0.90 psi) of more than 2.0, preferred of more than 2.5, especially preferred of more than 3.0 and most preferred of more than 3.5.

B. Superabsorbent particles of extremely high permeability are obtained of superabsorbents having a CRC of at least 18 g/g, preferably of at least 20 g/g, especially preferred of at least 22 g/g and a Gel Bed Permeability of more than 800, preferably of more than 1000, more preferred of more than 1200, especially preferred of more than 1500 and most preferred of more than 2000.

The new absorbent material show an improved excellent permeability combined with good absorption capacities and excellent rewet behavior.

Absorbent cores comprising highly permeable superabsorbent hydrogel-forming polymer with a shell exhibit excellent permeability. Compared to conventional superabsorbent polymers without polyamine coating, the highly permeable polymers according to the invention exhibit high absorption capacities and show for a given CRC improved performance. The permeability is improved compared to conventional uncoated superabsorbent material of the state of the art. The absorption capacities of the new absorbent material are very high, and their acquisition behavior is excellent.

The formation of absorbent members from said absorbent structures enables a production of improved personal care products. The improved products show excellent permeability and good absorbency. The application of the superabsorbent particles with improved permeability according to the invention enables the production of extremely thin and flexible personal care products comprising superabsorbent material in highest amounts which are therefore very comfortable in use. The improved products exhibit excellent permeability by unchanged absorption profile.

C. Improved acquisition behavior is obtained by polyamine coating of superabsorbent fines. Coated superabsorbent fines according to the invention exhibit the same performance as superabsorbent material with normal particle size distribution even after repeated dosages and show additional the benefits in acquisition behavior and rewet after the first application of aqueous solution.

Further coated fines show high acquisition rates and excellent rewets, caused by the high surface area they are offering and their higher number of smaller particles, compared to conventional superabsorbents. The fluid transmission or permeability is improved.

The new coated superabsorbent fines show no or gelblocking. Further the new products have the ability for trickling and are therefore very comfortable in handling. Therefore they are preferably used for applications in absorption of aqueous solutions e.g. in medical care, engineering and construction, in agriculture or as food packaging and storage and protective against fire.

Application of Polyamine Coated Hydrogel-Forming Polymer as Absorbent Core

The coated hydrogel-forming polymer particles are incorporated in fibrous substrate for application in personal care products. Methods of incorporation are those skilled in the art and may be suited for use in the present invention.

Suitable fibrous webs for the present invention include those made using synthetic polymeric fibers. The synthetic polymeric fibers may be formed from any polymeric material capable of forming fibers which fibers can be formed into a fibrous web. Suitable polymeric material from which the synthetic polymeric fibers may be formed include polyolefins, such as polyethylene, polypropylene, and the like; polyesters such as polyethylene terephthalate and the like; polyamides such as nylon 6, nylon 6,6, poly(iminocarboxylpentamethylene) and the like; acrylics, and modified cellulosic material, such as cellulose acetate and rayon; as well as mixtures and copolymers thereof.

The synthetic polymeric fibers may be formed by meltblowing, through a spunbond process, by extrusion and drawing, or other wet, dry and melt spinning methods known to those skilled in the art. The synthetic polymeric fibers from which the web is formed may have a discrete length or may be substantially continuous. For example, if the synthetic polymeric fibers are formed by meltblowing, the fibers may be substantially continuous (few visible ends). If the fibers are formed by extrusion and drawing to produce a tow, the tow may be used as produced or cut into staple fibers having a length, for example of from about 25 millimeters to about 75 millimeters or short cut into length of from about 1 millimeter to about 25 millimeters. The synthetic polymeric fibers may suitably have a maximum cross-sectional dimension of from about 0.5 micrometer to about 50 micrometers as determined by microscopic measurement using an optical microscope and a calibrated stage micrometer or by measurement from Scanning Electron photomicrographs.

The fibrous web may be formed directly through a spunbond or meltblown process, or by carding or air-laying staple or short cut fibers. Other methods of forming fibrous webs known to those skilled in the art may be suited for use in the present invention. The web may subsequently be bonded to enhance structural integrity. Methods of bonding fibrous webs are known to those skilled in the art and include thermal bonding, point bonding, powder bonding, ultrasonic bonding, chemical bonding, mechanical entanglement, and the like. The fibers may be homogenous fibers or may be a core/sheath or side-by-side fibers known in the art as bicomponent fibers.

The fibrous web may be formed from a single type of synthetic polymeric fiber or may contain synthetic polymeric fibers formed from different polymeric materials, having different fiber lengths or maximum cross-sectional dimensions. For example, the web may comprise a mixture of (1) bicomponent fibers having a polyethylene sheath and a polypropylene core which bicomponent fibers have a maximum cross-sectional dimension of about 20 micrometers and a length of about 38 millimeters and (2) polyester fibers (polyethylene terephthalate) having a maximum cross-sectional dimension of about 25 micrometers and a length of about 38 millimeters. Fibers 1 and 2 may be combined in a weight ratio of from 1:99 to 99:1. The fibers may be uniformly mixed or may be concentrated at opposite planar surfaces of the fibrous web.

The web suitably comprises from about 10 to 100 weight percent, beneficially of from about 20 to 100 weight percent, preferably of from about 25 to 100 weight percent, and most preferably of from about 50 to 100 weight percent synthetic polymeric fibers. In addition to the synthetic polymeric fibers, the web may contain from about 90 to 0 weight percent of a nonsynthetic polymeric fiber such as wood pulp fluff cotton liners, cotton, and the like.

In one preferred embodiment, the web contains synthetic polymeric fibers which are formed from a polymeric having a high wet modulus. The importance of the modulus of a material is discussed in the book "Absorbency" edited by P. K. Chatterjee (Elsevier, N.Y., 1985). A polymeric material will be considered to have a high wet modulus when it has a wet modulus greater than about 80 percent of its dry modulus as determined by ASTM (American Society for Testing and Materials) test method D 2101-91 using modified gauge lengths. It is often desired to form the synthetic polymeric fibers of the web from a polymeric material having a high wet modulus because such material generally form fibrous webs which possess a relatively high degree of wet resiliency. The wet resilience of a fibrous web is related to the pore structure (while under load) of the fibrous web. As will be discussed in greater detail below, it is often desired that the web have a relatively high degree of wet resilience.

The pore structure (while under load) of a fibrous structure formed from fibers of a polymeric material will, as discussed above, relate to the wet and/or dry modulus of the constituent fibers. Wet modulus of the consitutent fibers should be considered for fibers that may likely be wetted during use. For the purposes of estimating the effect of load on the pore structure of a fibrous structure formed from fibers of a polymeric material the tensile modulus of the fiber which can be related to the flexural rigidity of the fiber as shown in the book "Physical Properties of Textile Fibers" by W. E. Morton and J. W. S. Hearl (The Textile Institute, London, 1975) can be used.

As a general rule, the polymeric materials from which the synthetic polymeric fibers of the web are formed will be inherently hydrophobic. As used herein, the term "hydrophobic" describes a material which has a contact angle of water-in-air of greater then 90 degrees. The term "hydrophilic" refers to a material which has a water-in-air contact angle of less than 90 degrees. The water-in-air contact angle is suitably determined as set forth in the book "Absorbency" edited by P. K-Chatterjee (Elsevier, N.Y., 1985). As used herein, a polymeric material will be considered as "inherently" hydrophobic or hydrophilic when the polymeric material, free from any surface modifications or treatments, e.g., surface active agent, spin fishes, blooming agents, etc., is hydrophobic or hydrophilic, respectively.

When the synthetic polymer fibers of the web are formed from a polymeric material which is inherently hydrophobic, it is often desirable to treat the fibers with a surface modifying material to render the surface of the fiber hydrophilic. For example, a surfactant may be applied to the fibers.

The fibrous web may also comprise hydrophilic fibers. The hydrophilic materials may be inherently hydrophilic such as cellulosic fibers such as wood pulp fluff, cotton linters, and the like; regenerated cellulose fibers such as rayon; or certain nylon copolymers such as poly(pentamethylenecarbonamide)(nylon-6)/polyethylene oxide. Alternatively, the hydrophilic fibers may be hydrophobic fibers which have been treated to possess a hydrophilic surface. For example, the fibers may be formed from a polyolefin material which is subsequently coated with a surface active agent such that the fiber itself is hydrophilic as described herein. Other methods of hydrophilizing fibers formed from hydrophobic materials are known and suited for use in the present invention.

Methods of providing inherently hydrophilic fibers such as wood pulp fluff are known. So to are methods of providing regenerated cellulosic fibers such as rayon. Hydrophobic fibers which can be treated to possess a hydrophilic surface are suitably formed by processes known to those skilled in the art. If the hydrophilic fibers are hydrophobic fibers which have been treated to possess a hydrophilic surface, the fibers will suitably have a fiber length and a maximum cross-sectional dimension as set forth above. If the hydrophilic fibers are inherently hydrophilic such as wood pulp fluff, rayon, cotton, cotton linters and the like, the fibers will generally have a length of from about 1.0 millimeters to about 50 millimeters and a maximum cross-sectional dimension of from about 0.5 micrometers to about 100 micrometers.

The fibrous web suitably comprises from about 10 to 100 weight percent, beneficially from about 30 to 100 weight percent, and preferably from about 55 to 100 weight percent of hydrophilic fibers, preferably inherently hydrophilic fibers. In addition to the hydrophilic fibers, the web may contain form about 90 to 0 weight percent of high wet modulus, preferably inherently hydrophobic fibers. The web may be formed form a single type of hydrophilic fiber or may contain hydrophilic fibers having different compositions, lengths and maximum cross-sectional dimensions.

In one preferred embodiment, the web is formed from air laid cellulosic fibers such as wood pulp fluff. Wood pulp fluff fibers are preferred for use due to their ready availability and due to the fact that the fibers are relatively inexpensive compared to synthetic fibers.

In one especially preferred embodiment, the web is compressed under reduced pressure.

In another preferred embodiment, the coated hydrogel-forming polymer particles are incorporated together with superabsorbent polymer fibres into fibrous substrate.

Superabsorbent polymer fibres are preferred for several reasons. At first, they can be easily incorporated into the structure of a nonwoven material. Polymer fibres remain in place better than superabsorbent polymer particles in the case when compressive forces and other forces act on the absorbent article. Further, superabsorbent polymer fibres are generally softer and more flexible than particulate superabsorbents. Superabsorbent polymer fibres may also have less tendency to cause holes in the backsheet when they are in their dry state than some particulate superabsorbent polymers. Superabsorbent polymer fibres can be distributed within a layer of material so that the fibers are generally spaced away from adjacent fibres at sufficient distance. Therefore, superabsorbent polymer fibres will have a reduced tendency to come in contact with each other and cause gel-blocking during absorption.

Procedure of Forming Composites Containing Polyamine Coated Hydrogel-Forming Polymer Water-absorbent composites can be manufactured from superabsorbent particles with a shell. Preferred are polyamine coated superabsorbent polymers which are brought together with structure forming compounds such as for example fibrous matrices (built from cellulosic fiber, synthetic fibers or mixtures thereof as air-laid or/an wet-laid web), open- or closed celled foams, or others. The following is explained with polyamine coated superabsorbent polymers, but can also be adjusted to other superabsorbent particles with a shell.

Alternatively, a composite can be formed from two layers, which are combined in a way that a plurality of chambers are formed in which the polyamine coated superabsorbent polymer particles are incorporated. In this case, at least one of said layers has to be water-pervious. Suitable layers are tissues or other webs, open- or closed celled foams, perforated films, elastomers or fibrous matrices. Included are also laminates of at least two layers, comprising said superabsorbent particles.

Further a composite can be formed from a carrier layer (e.g. a polymer film), onto which the superabsorbent polymer particles are affixed. The fixation can be carried out at one side or at both sides. The carrier layer can be water-pervious or water-impervious.

According to the present invention, the composites containing more than 30% by weight, preferred more than 40% by weight, especially preferred more than 50% by weight and most preferred more than 60% by weight superabsorbent particles with crosslinked polyamine shell. Preferred are composites from superabsorbent particles and fibrous matrices.

Suitable fibers for forming fibrous matrices are mentioned above.

In a preferred embodiment of the present invention, the polyamine coated superabsorbent particles are incorporated in a hydrophilic fibre matrix to form the composite. This can be done by different procedures mentioned below.

The fibrous matrix can be formed from a mixture of synthetic fibers and cellulosic fibers in a mixing ratio from (100 to 0) synthetic fibers to (0 to 100) cellulosic fibers. The cellulosic fibers are optionally chemically stiffened for improvement of the structural integrity Chemical stiffening is made as nonlimiting examples by coating the fibers with polyamide-epichlorohydrine (KymeneO) or by a chemical reaction by addition of crosslinkers (e.g. $C_2$-$C_8$ dialdehyde, $C_2$-$C_8$ monoaldehyde, $C_2$-$C_9$ polycarboxylic acids), which performing intra-molecular crosslinks within the cellulosic fiber.

Non-limiting examples for preparation of composites comprising synthetical fibers (a), cellulosic fibers (b) and polyamine coated superabsorbent particles (c) wherein the mixing ratio of synthetic fibers and cellulosic fibers can be varied from (100 to 0) synthetic fibers to (0 to 100) cellulosic fibers including (1) procedures wherein (a), (b) and (c) are mixed at the same time, (2) procedures wherein a mixture of (a) and (b) is mixed with (c), (3) procedures wherein a mixture of (b) and (c) is mixed with (a), (4) procedures wherein a mixture of (a) and (c) is mixed with (b), (5) procedures wherein (b) and (c) is mixed and (a) is continuously added, (6) procedures wherein (a) and (c) is mixed and (b) is continuously added, (7) procedures wherein (b) and (c) are separately mixed with (a).

Preferred are procedures (1) and (5). The apparatus is not limited and every apparatus for mixing known in the art can be used.

The resulting nonwoven fabrics are highly flexible, with a minimum of coarseness, have sufficient strength to handle through the process, and displayed very little SAP shakeout.

In a further preferred embodiment of the present invention, it has been found that heating a resin for a sufficient time at a sufficient temperature above the Tg (glass transition temperature) of the resin improves the absorption properties of the resin. In accordance with one important embodiment of the present invention, it has been found that when a layer of the polyamine coated superabsorbent particles is heated to at least about 50° C. during or after manufacture of the composite, not only are the absorption properties improved, but the particles are strongly adhered to themselves and to any fiber contained in the composite so that there is little to no loss of superabsorbent particles during manufacture and handling. Thus, the composite without added adhesive, has new and unexpected structural integrity, for the above-described uses, particularly diaper cores.

Procedure of Forming Air-Laids Containing Polyamine Coated Hydrogel-Forming Polymer Present day diapers generally consist of a topsheet made from a nonwoven material that is in contact with the skin of the wearer, an acquisition layer below (i.e., opposite the skin of wearer) the topsheet, a core that is below the acquisition layer, and a backsheet below the core. This construction is well known in the industry. In a preferred embodiment, the present diaper consists essentially of a topsheet, a core, and a backsheet, i.e., an acquisition layer is not present. The improvements provided by present polyamine coated superabsorbent particles permit an acquisition layer to be omitted from a disposable diaper. Such a result is both new and unexpected in the art in that an expensive acquisition layer can be omitted, the diaper is lighter and thinner, and absorptive properties are not adversely affected.

Suitable fibers for forming fibrous matrices are mentioned above.

Typically, an air-laying process involves mixing the components in air and condensing and rearranging the mixture on a forming screen. Any suitable conventional air-laying process may be used. Generally, in an air-layed process bundles of small fibres having typical lengths ranging from about 3 mm to about 19 mm are separated and entrained in an air supply and then deposited onto a forming screen, usually with the aid of a vacuum supply. The randomly deposited fibres then are bonded to one another using, for example, hot air or spray adhesive.

In detail, the fibrous web is formed directly by air-laying staple or short cut fibers. Prior art apparatus for the production of a fibrous web comprise several fiber distributors and corresponding suction boxes mounted at intervals along forming wire. When using such an apparatus, the thickness of the fibrous web formed is increased stepwise. However, fibrous products which are made stepwise tend to delaminate because of an insufficient integration between adjacent fiber layers. Consequently, a relatively large amount of binder is required to obtain a desired strength of the final fibrous product. Furthermore, this method of manufacturing fibrous products presents serious problems when light weight products are desired as in the present case of ultrathin personal care products. On the other hand, if the fibrous layer initially deposited on the forming wire is very thin, it will be consequently easily damaged in the following zone of production. Furthermore, in case of very thin products, in which the fibers are not entangled in one another, the fibers tend to form groups of fibers during the passage between two fiber distributors and, therefore, non-uniform products are obtained. This problem becomes much stronger, when the speed of the forming wire is increased to increase the production rate.

In order to prevent a non-uniform distribution of fibers in the fiber layers formed, driven rollers contacting the fiber layer deposited thereon have been mounted at each fiber distributor. However, the fibers tend to accumulate at the surfaces of the rollers and form layers thereon, unless their moisture content is maintained within narrow limits. Furthermore, such rollers tend to increase the tendency of delamination of the fibrous product formed because they smooth out the surface of the fiber layer formed and consequently prevent fiber ends extending from the layer from being entangled with fibers of a fiber layer subsequently applied.

To enhance structural integrity the web may subsequently be bonded. Methods of bonding fibrous webs are known to those skilled in the art and include thermal bonding, point bonding, powder bonding, ultrasonic bonding, chemical bonding, mechanical entanglement, and the like. The fibers may be homogenous fibers or may be a core/sheath or side-by-side fibers known in the art as bicomponent fibers.

In accordance with the present invention, a sheet of material as air-laid is continuously manufactured containing polyamine coated hydrogel-forming polymer particles which may be incorporated into the sheet material. In accordance with the principles of the present invention, it has been found, unexpectedly, that a continuous sheet can be continuously manufactured on conventional papermaking apparatus, using any of the wet, dry, or wet-dry processes to manufacture a water-absorbent sheet-like substrate containing 30%-100% by weight of the polyamine coated hydrogel-forming polymer particles, added to form the sheet material articles of the present invention. Especially preferred it the air-laid process. The sheet materials can be manufactured having new and unexpected structural integrity with little or no shakeout or loss of superabsorbent particles during or after manufacture.

The sheet material of the present invention is stable against delamination. However, to further increase the integrity of the fibrous product, it is possible to add sufficient binder only to maintain the integrated fibers in place. Furthermore, different types of binders may be introduced in the sheet-like material. For example, binders which are incompatible and which are activated in different ways may be used. Examples of such binders are thermo-curing acrylic binders and binders prepared from starches.

Utilizing polyamine coated superabsorbent material, it could be shown that a higher concentration of SAP particles can be incorporated in a lower portion of cellulosic fluff pulp fibers, that is from 30% to 100%, and in an especially preferred manner it was done without an increase in bicomponent (thermal-bondable) fibers, and in the most preferred case absorbent air-laid fabrics were manufactured without the use of any bicomponent fiber at all.

It is assumed that a major reason for obtaining a strongly coherent fibrous product by using the papermaking apparatus is that the fibrous product during its formation is constantly under the influence of the suction. There is no need to roll the fiber layer before further fibers are applied thereon.

The resulting nonwoven fabrics were highly flexible, with a minimum of coarseness, had sufficient strength to handle through the process, and displayed very little SAP shakeout.

In a further preferred embodiment of the present invention, it has been found that heating a resin for a sufficient time at a sufficient temperature above the Tg (glass transition temperature) of the resin improves the absorption properties of the resin. In accordance with one important embodiment of the present invention, it has been found that when a layer of the polyamine coated superabsorbent particles is heated to at least about 50° C. during sheet material manufacture (e.g., by a heated pressure roll or oven), not only are the absorption properties improved, but the particles are strongly adhered to themselves and to any fiber or filler (e.g., clay) contained in the sheet material so that there is little to no loss of superabsorbent particles during manufacture and handling. Thus, a sheet material having 0%-70% by weight non-SAP fiber, and without added adhesive, has new and unexpected structural integrity, for the above-described uses, particularly diaper cores.

The sheet materials of the present invention exhibit exceptional water absorption and retention properties. In addition, the sheet materials have an ability to absorb liquids quickly, demonstrate good fluid permeability and conductivity into and through the superabsorbent particles, and have a high gel strength such that the hydrogel formed from the superabsorbent particles, upon hydration, resists deformation under an applied stress or pressure, when used alone or in a mixture with other water-absorbing resins.

The superabsorbent polymer containing air-laids are useful as diaper cores and in other catamenial or hygienic devices, absorptive pads, and wipes.

Application of the New Composites or Air-Laids in Personal Care Products

As used herein, the term "personal care products" refers to articles that absorb and contain body fluids, and more specifically refers to articles that are placed against the body of the wearer to absorb and contain the various fluids discharged from the body. These absorbent articles typically comprise a fluid impervious backsheet, a fluid pervious topsheet and an absorbent core positioned between the backsheet and the topsheet.

The topsheet is compliant, soft feeling and non-irritating to the wearer's skin. Further the topsheet is liquid pervious permitting body fluids to readily penetrate through its thickness. A suitable topsheet is manufactured from a wide range of materials such as woven and nonwoven materials; polymeric materials such as apertured formed thermoplastic film, apertured plastic films and hydroformed thermoplastic films, porous foams; reticulated thermoplastic films and thermoplastic scrims. Suitable woven and nonwoven materials can be comprised of natural fibers (wood, cotton fibers and the like), synthetic fibers (polymeric fibers such as polyester, polypropylene, or polyethylene fibers) or from a combination of natural and synthetic fibers. Preferred topsheets are selected from high loft nonwoven topsheets and aperture formed film topsheets, that have a reduced tendency to allow fluids to pass back through and rewet the wearer's skin. The body surface of the topsheet can be hydrophilic so as to make the transfer of body fluids through the topsheet faster. Preferably, surfactant is incorporated into the topsheet, or the body surface of the topsheet is made hydrophilic by treating it with a surfactant.

The topsheet is positioned adjacent the body surface of the absorbent core. According to the invention, the absorbent core comprises both substrate, preferably from woven or nonwoven, and a plurality of polyamine coated superabsorbent particles incorporated in said substrate and thus applied as composite.

Especially preferred is the only use of the composite or air-laid as absorbent core. The topsheet is preferably joined to the absorbent core and to the backsheet by attachment means known in the art.

The backsheet is typically impervious to aqueous body fluids and is preferably made from a thin plastic film, although other flexible fluid impervious materials may also be used. The term "flexible" means the use of material, that are compliant and will readily conform to the general shape and contours of the human body. The backsheet prevents body fluids absorbed and contained in the absorbent core from wetting articles that contact such as undergarments, pants and the like. The backsheet can comprise a woven or nonwoven material, polymeric films such as thermoplastic film of polyethylene or polypropylene, or composite materials, such as film-coated nonwoven material. Preferably, the backsheet is a polyethylene film having a thickness of from about 0.012 mm to about 0.05 mm. Preferably the backsheet can permit vapours to escape from the absorbent core while still preventing body fluids from passing through the backsheet. That is the backsheet is preferably breathable.

According to the invention, the composite or air-laid as absorbent core is positioned between the backsheet and the topsheet optionally by attachment means.

The inventive profile of the absorbent article enables the manufacture of extremely thin personal care products that are very comfortable in use.

Further Use of the Superabsorbent Particles with a Shell

Superabsorbent particles with a shell of the invention are very useful as absorbents for water and aqueous fluids, can be used with advantage as an absorbent component in hygiene articles such as diapers, tampons or sanitary napkins and also as water retainers in agricultural market gardening, as filtration aids.

The present invention further provides for the use of the above mentioned superabsorbent particles with a shell for absorbing aqueous fluids such as for example hygiene articles, storage, packaging, transportation (packaging material for water-sensitive articles, for example flower transportation, shock protection)

food sector (transportation of fish, fresh meat; absorption of water, blood in fresh fish/meat packs)

water treatment, waste treatment, water removal cleaning agricultural industry (irrigation, retention of meltwater and dew precipitates, composting additive)

The superabsorbent particles with a shell according to the invention are suitable for the above applications; they may be used in combination with other superabsorbers, and the advantages of the inventive hydrogels can be combined with those of the conventional hydrogels through an appropriate spatial configuration for example.

Particularly preferred applications for superabsorbent particles with a shell, especially for those based on fines or on mixtures with fines, are:

medicine (wound plaster, water-absorbent material for burn dressings or for other weeping wounds, rapid dressings for injuries; rapid uptake of body fluid exudates for later analytical and diagnostic purposes), cosmetics, carrier material for pharmaceuticals and medicaments, rheumatic plaster, ultrasound gel, cooling gel, cosmetic thickener, sunscreen, thickeners for oil/water or water/oil emulsions;

textile (gloves, sportswear, moisture regulation in textiles, shoe inserts, synthetic fabrics), hydrophilicization of hydrophobic surfaces; pore-forming chemical process industry applications (catalyst for organic reactions, immobilization of large functional molecules (enzymes), heat storage media, filtration aids, hydrophilic component in polymer laminates, dispersants, liquefiers)

building construction (sealing materials; systems or films that will self-seal in the presence of moisture; fine-pore formers in sintered building materials or ceramics; self-sealing insulation for water pipes or for underground pipes and tubes; sealing of building materials in the soil as a result of the SAP swelling in the moist soil with time delay and thus effecting a closure or seal; finishing of carpets and carpet floorings), installation, vibration-inhibiting medium, assistants in relation to tunneling in water-rich ground, assistants in relation to digging and boring in water-rich ground, cable sheathing fire protection (spraying of SAP gel in the case of fires such as for example forest fires), coextrusion agent in thermoplastic polymers; production of films and thermoplastic moldings capable of absorbing water (for example agricultural films capable of storing rain and dew water; SAP-containing films for keeping fresh fruit and vegetables which can packed in moist films to avoid fouling and wilting); SAP coextrudates, for example with polystyrene carrier substance in active-ingredient formulations (drugs, crop protection)

agricultural industry: protection of forests against fungal and insect infestation, delayed release of active ingredients to plants.

4. Test Procedures 4.1 Rewet and Acquisition Time/Laboratory Core Forming Procedure Laboratory cores referred to herein, were prepared using a conventional laboratory procedure as follows:

A laboratory core-forming unit is used comprising a two-chamber vacuum system forming an airlaid fluff pulp-absorbent composite matrix to produce a 12 cm×21 cm diaper core. The core-forming unit comprises a roller brush on a variable-speed laboratory motor, a fiber distribution screen in close proximity to the brush, a forming screen on an adjustable damper, and a vacuum system capable of supplying a consistent and continuous negative pressure between 8 and 15 inches of water.

The core-forming unit is contained such that the vacuum pulls the fibers and granular material from an adjustable introduction slide, through the rotating brush and distribution screen, directly onto the forming screen. The vacuum exhaust is recirculated through the inlet of the formation slide, thereby controlling the temperature and humidity of the operation.

When forming a core, the desired amount of defiberized fluff pulp is evenly disbursed in small pieces onto the brush roller in the upper chamber. In the lower chamber, a rectangular tissue, or topsheet (21 cm×12 cm), is placed onto the forming screen. For most cores, the sliding upper chamber lid is partially closed to leave about a one-half inch gap. In the case of a homogeneous pulp/SAP core, the SAP is sprinkled through the gap into the upper chamber immediately after the brush begins rotating. In order to achieve a homogeneous distribution, a small amount of SAP is added to the fluff prior to beginning the motor. The amount of time used to introduce the remainder of the SAP varies with the amount of fluff pulp utilized. After the fiber and absorbent polymer material are deposited, the motor is turned off, and the damper unit containing the laboratory core is removed from the lower chamber. The uncompressed core then is placed on a backsheet made from a polymeric film, and put into a compression unit. At this time, another rectangular tissue and a nonwoven coverstock is placed on top of the core. Absorbent cores are compressed for a given amount of time, typically 5 minutes, with a hydraulic press at pressures of between about 5,000 psi and about 10,000 psi, and typically about 7,000 psi, to achieve the desired density. After the 5 minutes, the laboratory-prepared absorbent cores are removed from the press, weighed, and measured for thickness.

Laboratory cores and commercial diapers, were tested for rewet under a 0.7 psi load, liquid acquisition time, and liquid acquisition rate. The following describes the procedure to determine the acquisition and rewet under load of a hygienic article, like a diaper. These tests exhibit the rate of absorption and fluid retention of a 0.9%, by weight, saline solution, by a hygienic article over 3 to 5 separate fluid insults while under a load of 0.7 psi.

Apparatus:

100 ml separatory funnel, configured to deliver a flow rate of 7 ml/sec., or equivalent;

3.642 kg circular weight (0.7 psi) 10 cm diameter, with 2.38 cm ID perspex dose tube through the center of weight; VWR Scientific, 9 cm filter paper or equivalent; 2.5 kg circular weight (0.7 psi)—8 cm diameter; Digital timer; Electronic balance (accuracy of a 0.01 gram); Stopwatch.

Procedure:

1. Preparation
   (a) Record the weight (g) of the hygienic article, e.g., diaper, to be tested;
   (b) Place hygienic article flat on the bench top, for example, by removing any elastics and/or taping the ends of the article to the bench top;
   (c) Place the 3.64 kg circular weight onto the hygienic article with the opening of the perspex dose tube positioned at the insult point (i.e., 5 cm toward the front from the center).

2. Primary Insult and Rewet Test
   (a) Measure 40 ml of 0.9% NaCl solution (i.e., 0.9% by weight sodium chloride in deionized or distilled water) into separatory funnel. Dispense the NaCl solution into the perspex tube of the weight at a flow rate of 7 ml/sec and start the timer immediately. Stop the timer when all of the NaCl solution has completely disappeared from the surface of the hygienic article at the base of the perspex tube. Record this time as the primary acquisition time (sec).
   (b) After 10 minutes have elapsed, remove the weight and conduct the rewet test procedure:
      (i) Weigh a stack of 10 filter papers, record this value (dry weight).
      (ii) Place the filter papers over the insult point on the hygienic article. Set the timer for 2 minutes. Place the 2.5 kg weight onto the filter papers and start timer immediately.
      (iii) After 2 minutes have elapsed, remove the weight and reweigh the filter papers (wet weight). Subtract the dry weight of the filter papers from the wet weight, this is the rewet value. Record this value as the primary rewet value (g).

3. Secondary Insult and Rewet Test
   (a) Place the 3.64 kg weight back onto the hygienic article in the same position as before. Repeat step 2a using 40 ml NaCl solution (recoding the absorption time as the secondary acquisition time) and steps 2b (i)-(iii) using 20 filter paper (recording the rewet values as the secondary rewet).

4. Tertiary, and additional, Insult and Rewet Tests
   (a) Place the load back onto the diaper in the same position as before. Repeat step 2a using 40 ml of NaCl solution (recording the absorption time as the tertiary acquisition time) and steps 2b (i)-(iii) using 30 filter paper (recording the rewet value as the tertiary or subsequent rewet).

4.2 Centrifuge Retention Capacity CRC

This method determines the free swelling capacity of the hydrogel-forming polymer. Using this method, 0.2000±0.0050 g of dry hydrogel-forming polymer of size fraction 106-850 μm are inserted in a teabag. The teabag is placed in saline solution (0.9 w % sodium chloride) for 30 minutes (at least 0.83 l saline solution/1 g polymer). Afterwards the teabag is centrifuged for 3 minutes at 250 G. The absorbed quantity of saline solution is determined by measuring the weight of the teabag.

4.3 Absorbency Under Load AUL

The measurement of AUL is carried out in a cylindrical cell from lucite (Plexiglas) with an inner diameter of 60 mm and a height of 50 mm. At the bottom of the cell a sieve of stainless steel with meshes of 36 μm is fixed. The measuring cell consists further of a plate of lucite with a diameter 59 mm and a weight, which can be placed into the cell together with the plate. The weight of plate and weight together is 1345 g for AUL 0.7 psi.

For determination of e.g. AUL 0.7 psi the weight of the empty cell and the plate is noted as value $W_0$. After this, 0.900±0.005 g hydrogel-forming polymer (sieve fraction 150-800 μm) is placed in the cylindrical cell and homogenuously distributed onto the sieve of the cell. Then the plate is placed in the cell above the polymer particles and the weight of the whole measuring unit is determined as $W_a$. Now the desired weight is placed onto the plate within the measuring system. A filter of ceramic with diameter 120 mm and a porosity of 0 is placed in the middle of a Petri-dish of diameter 200 mm and a height of 30 mm. Now an aqueous solution of 0.9 w % sodium chloride is poured into the Petri-disc in that way, that the surface of the solution is rised towards the surface of the filter plate, but without wetting it. Afterwards a filter paper of diameter 90 mm and pores <20 μm (trade name S&S 589 Schwarzband of Schleicher & Schüll) is placed onto the ceramic plate. The hydrogel-forming polymer containing cylinder is placed together with lucite-plate and weight onto the filter paper and left there for 60 minutes. After this time the complete measuring unit is removed from the Petri-dish and afterwards the weight is removed. The weight of the cylindrical cell with the swollen hydrogel particles and the lucite plate is measured and the weight noted as $W_b$.

The AUL is calculated as follows:

$$\text{AUL } 0.7 \text{ psi}[g/g]=[W_b-W_a]/[W_a-W_0]$$

4.4 Pressure Absorbency Index PAI

The method for the determination of the PAI (Pressure Absorbency Index) is exactly written in U.S. Pat. No. 5,601,542

4.5 Saline Flow Conductivity SFC

The method for the determination of the SFC is exactly written in U.S. Pat. No. 5,599,335.

4.6 Gel Bulk Density

The method for the determination of the GBD is exactly written in U.S. Pat. No. 5,834,575

4.7 Gel Bed Permeability

The method for the determination of the GBP is exactly written in WO 00/62825.

4.8 Dry/Wet-Integrity

This test procedure outlines an approved method to quantitatively determine the absorbent core integrity of hygienic products.

Apparatus

Texture Analyser TA-XT2 (purchased from Texture Technologies Corp.); 5 centimeter disk attachment for texture analyser; Tortilla testing apparatus; Electronic balance, accuracy of 0.01 gram Materials 0.9% NaCl Solution, with Dye (1 g Dye Per 1 Liter of Solution) Procedure 1.0 Setting Up and Running the Texture Analyzer Program:
   a) Double-click the Texture Expert Exceed program icon.
   b) In User Selection window, select OK.
   c) Project Wizard will appear on screen. Select QUIT PROJECT WIZARD.
   d) Go to T.A. at the top of screen and select T.A. SETTINGS.
   e) Test Mode and Option:
      Measure Force in Compression
      Return to Start
   f) Parameters:
      Pretest Speed: 10 mm/s
      Test Speed: 0.2 mm/s
      Post Test Speed: 10.0 mm/s
      Distance: 35 mm
      Load Cell: 5-0.1
   g) Trigger:
      Type: Auto
      Force: 5 grams
      Stop Plot at: Trigger Return
   h) Units:
      Force: Grams
      Distance: mm
   i) Break:
      Detect: Off
   j) The test settings are now set and you are ready to run a test
   k) Select UPDATE 2.0 Sample Preparation:
   a) Weigh hygienic article and tape flat onto lab bench (poly side down).
   b) Measure and determine the center of the product (x-direction) and draw a line across the product (y-direction).
   c) Draw another line 10 cm toward the front of product.
   d) If running a wet strength test, insult product with 50 ml of 0.9% NaCl solution at the insult zone (5 cm from the product center line toward the front of the product). If running a dry strength test, skip this step.
   e) Cut out a 10 cm×10 cm section of the absorbent core bordered by the 2 lines drawn.
   f) Carefully remove the coversheet, tissue layers, and poly film backsheet (use a metal spatula if necessary). Try not to disturb the absorbent core.
   g) Weigh and record the weight of the 10×10 section (fluff and SAP only).
   h) Carefully transfer the core section into the "tortilla tester" in a star-like fashion (see diagram 1 on page 5).
   i) Clamp the core sample in between the 2 metal plates of the "tortilla tester" by tightening the four brass nuts. For a wet strength test, tighten nuts evenly until the core sample begins to menisce in a convex manner. Tightening any further will break the core apart. For a dry strength test, tighten the nuts evenly until no further tightening is possible without extreme effort.

3.0 Running a Test:
  a) Insert disk into drive labelled "Texture Analysis: Settings, Macros"
  b) Select FILE, select NEW, and select GRAPH WINDOW.
  c) Select T.A. and CALIBRATE FORCE using 2 kg weight.
  d) Select T.A. and RUN A TEST.
    Archive as: put an "x" in the AUTO SAVE box (save as whatever you like)
    Post-test: put an "x" in the MACRO box to run macros automatically
  e) In the RUN A TEST window, make sure that the PPS (points per second) is at 100.00.
  f) Place the test unit onto the testing platform within the rectangular area outlined in black marker.
  g) Select RUN.

4.0 Running the Next Test:
  a) Remove tested sample, clean test probe, and place next sample into testing unit ("tortilla tester").
  b) Select a NEW FILE and Select GRAPH WINDOW.
  c) Check T.A. Settings and Calibrate Force after every 5 tests.

5.0 Notes:
  a) 2 types of tests can be run in this procedure: wet strength and dry strength of absorbent cores. The only difference in procedure is that the wet strength test requires 50 ml of 0.9% NaCl solution and a more cautious method of clamping the 10×10 cm core section within the "tortilla tester".
  b) Be very careful when removing the coversheet, tissue layers, and poly film backsheet. Try to leave as much of the absorbent core intact as possible. Do not be concerned with core material that is held back by adhesive.
  c) Immediately after separating the 10×10 cm absorbent core section from the diaper and weighing it, test the section.
  d) Texture Expert Exceed is a complicated program and requires some time and patience.

4.9 Performance Parameter PP

The Performance Parameter PP is defined as Rewet-Number×Acquisition Time; the Rewet-Number is defined according to the 4$^{th}$ Rewet-value as follows:

| | |
|---|---|
| Rewet 0.00-0.99 g | Rewet-Number = 1 |
| Rewet 1.00-1.99 g | Rewet-Number = 2 |
| Rewet 2.00-2.99 g | Rewet-Number = 3 |
| Rewet 3.00-3.99 g | Rewet-Number = 4 |
| Rewet 4.00-4.99 g | Rewet-Number = 5 |
| Rewet 5.00-5.99 g | Rewet-Number = 6 |
| Rewet 6.00-7.99 g | Rewet-Number = 7 |
| Rewet 8.00-9.99 g | Rewet-Number = 8 |
| Rewet >9.99 g | Rewet-Number = 9; |

The Acquisition time is the corresponding value to the 4$^{th}$ Acquisition time.

4.9 Vortex Time 50 ml of 0.9 wt.-% saline solution is placed into a 100 ml beaker. The saline solution is stirred at 600 rpm using a magnetic stirrer (magnetic stirring bar 30 mm×8 mm). The bottom of the vortex should be near the top of the stir bar. Then 2±0.001 g of SAP is quickly added into the solution but not into the center of the vortex to avoid lumping, and the stop watch is started. When the surface of the solution becomes flat, the time is stopped and recorded. Total time in seconds required for the vortex to close is the vortex time. Each SAP sample has to be run in triplicate, the average of the values is reported as vortex time.

5. Moisture Content—Weight Loss Upon Heating
  Procedure
    Place a dish and cover into the oven for 3 h at (105±2)° C. During this period, the cover shall be removed from the dish. At the end, the cover shall be replaced on the dish and the covered dish transferred to the dessicator to let cool for 30 min to room temperature.
    Weigh the dish with cover to the nearest 0.001 g and record the exact weight as $m_1$ g.
    Remove the cover and, with the help of a "V"-shaped spatula, add approximately 4.0 g of a well-mixed representative test portion that shall be free from lumps.
    Replace the cover and weigh immediately to the nearest 0.001 g. Record the exact weight as $m_2$ g.
    Distribute the test portion in a uniform particulate layer over the bottom of the dish, e.g. with the help of a spatula and gentle tapping.
    Place the open dish, and its corresponding cover, together in the oven at (105±2)° C. for 3 h.
    After this period, immediately cover the dish, place it in the desiccator and allow to cool for 30 min.
    When the dish has cooled to room temperature, remove it from the desiccator and weigh immediately to the nearest 0.001 g. Record the exact weight as $m_3$ g.
    Carry out at least two (2) determinations on the same well-mixed laboratory sample, simultaneously or successively, by the same analyst.
  Calculation and Results
  Calculate the moisture content MC by:

$$MC = 100 \times \frac{m_2 - m_3}{m_2 - m_1} \%$$

Where:
MC=moisture content, in % of the starting weight
$m_1$=mass in g, of the dried empty dish and lid
$m_2$=mass, in g, of the dish with test portion and lid, before drying;
$m_3$=mass, in g, of the dish with test portion and lid, after drying.

EXAMPLES

Preparation of Base Polymer, Comparative Samples and Coating Procedures

Example 1

To 90 grams of acrylic acid (from BASF Corp.) add 221 grams of deionized water and 0.077 grams of methylenebisacrylamide (from Aldrich) and stir. Add 74.94 grams of 50% NaOH slowly to the solution while keeping the temperature under 20° C. After addition of NaOH cool the solution to about 10° C. and add 0.0561 grams of 2-hydroxy-2-methyl-1-phenyl-propane (Darocur 1173 from Ciba) and 1.823 grams of sodium persulfate (from Aldrich) with stirring. Pour the solution into a 4"×8" glass dishand polymerize for 12.5 minutes under UV light (UV intensity=20 mW/cm$^2$). Extrude the gel through a Kitchen Aid meat grinder and dry it at 145° C. for one hour and then mill and size it to 180-710 µm Comparative Example 1

Took the polymer, which was prepared on example 1 and surface coated with a mixture, which contains 0.1500 grams denacol, 3.6950 grams of PG and 6.1250 grams of water. Weigh out 10 grams of base polymer and put it in a disposable beaker and add 0.4 of solution (dropwise) into the SAP while stirring it. Make sure the coating is uniformed. Transfer the coated SAP into a 50 ml beaker and pack it lightly. Cure the sample at 150° C. for one hour and then size it to 180-710 µm.

Example 2

To 292 grams of acrylic acid (from BASF Corp.) add 783 grams of deionized water and 0.500 grams of methylenebisacrylamide (from Aldrich) and stir. Cool the solution to about 10° C. and add 0.200 grams of 2-hydroxy-2-methyl-1-phenyl-propane (Darocur 1173 from Ciba) and 2.5 grams of sodium persulfate (from Aldrich) and 2.8 grams of sodium metabisulfite and stir. Pure the solution into a 4"×8" glass dish and polymerize for 12.5 minutes under UV light (UV intensity=20 mW/cm$^2$). Extrude the gel through a Kitchen Aid meat grinder and then add 159.15 grams of Na$_2$CO$_3$ to the gel and extrude it again. Dry the gel at 150° C. for one hour and mill and size it to 180-710 µm.

Comparative Example 2

Took the polymer, which was prepared on example 2 and surface coated with a mixture, which contains 0.1500 grams denacol, 3.6950 grams of PG and 6.1250 grams of water. Weigh out 10 grams of base polymer and put it in a disposable beaker and add 0.4 of solution (dropwise) into the SAP while stirring it. Make sure the coating is uniformed. Transfer the coated SAP into a 50 ml beaker and pack it lightly. Cure the sample at 150° C. for one hour and then size it to 180-710 µm.

Example 3

To 297 grams of acrylic acid (from BASF Corp.) add 783 grams of deionized water and 0.528 grams of methylenebisacrylamide (from Aldrich) with stirring. Cool the solution to about 10° C. and add 0.200 grams of 2-hydroxy-2-methyl-1-phenyl-propane (Darocur1173 from Ciba) and 5.99 grams of sodium persulfate (from Aldrich) with stirring. Pure the solution into a 4"×8" glass dishand polymerize for 12.5 minutes under UV light (UV intensity=20 mW/cm$^2$). Extrude the gel and weigh out 363.65 grams of gel and then add 55.16 grams of Na$_2$CO$_3$ to the gel and then extrude again. To this, add 2.5 grams of ethylene glycol diglycidyl ether (denacol EX-810) and then extrude again. Dry the gel at 150° C. for one hour and mill and size it to 180-710 µm.

Comparative Example 3

Took the polymer, which was prepared on example 3 and surface coated with a mixture, which contains 0.1500 grams denacol, 3.6950 grams of PG and 6.1250 grams of deionized water. Weigh out 10 grams of base polymer and put it in a disposable beaker and add 0.4 of solution (dropwise) into the SAP while stirring it. Make sure the coating is uniformed. Transfer the coated SAP into a 50 ml beaker and pack it lightly. Cure the sample at 150° C. for one hour and then size it to 180-710 µm.

Example 4

To 700 grams of acrylic acid (from BASF Corp.) add 0.200 grams of Trimethylolpropanetriacrylate (TMPTA) and 660.38 grams of deionized water while stirring. Add 305.977 grams of Na$_2$CO$_3$ to the solution while keeping the mixture temperature around 50° C. Heat the mixture if necessary. Raise the temperature to 57° C. Take 220 grams of this mixture and place it in a 400-ml beaker. Add 1.45 grams of 15% aqueous 2,2 Azobis (2-methylpropanamide) dihydrochloride (V-50 from Wako Chemical), 1.45 grams of 10% aqueous sodium persulfate and 12.0 grams of fines (SAP product with particle size <106 µm. Pour the mixture into a belt tray and add two drops of 33% aqueous sodium persulfate and couple drops of 33% aqueous sodium metabisulfite. Dry the slab over-night at 60 C and mill and size to 180-710 µm.

Comparative Example 4

Took the polymer, which was prepared on example 4 and surface coated with a mixture, which contains 0.1500 grams denacol, 3.6950 grams of PG and 6.1250 grams of water. Weigh out 10 grams of base polymer and put it in a disposable beaker and add 0.4 of solution (dropwise) into the SAP while stirring it. Make sure the coating is uniformed. Transfer the coated SAP into a 50 ml beaker and pack it lightly. Cure the sample at 150° C. for one hour and then size it to 180-710 µm.

Example 5

Use a 4 liter glass reactor flask. Cool the acrylic acid 926% solid) and P-30 (0.5-0.8% boaa) to 10° C. and add to the reaction flask. Cool the deionized water to 10° C. and add to the reaction flask. Purge this mixture with nitrogen to displace the oxygen to a level of 1 ppm or less. This usually requires a flow of 10 scfm of nitrogen for 20 mins. Continue bubbling nitrogen and add the iron (0.2 ppm boaa) and wait 2 minutes. Then add the ascorbic acid (0.011% boaa) and wait for 2 minutes while still bubbling the nitrogen into the reaction flask. Then add the hydrogen peroxide (0.011% boaa) while still bubbling the nitrogen into the reaction flask. After several minutes the reaction will initiate and polymer will begin to form. At this point discontinue bubbling nitrogen into the flask. After 12 hours the reaction is completed and the polymer can be removed from the reaction flask. Take the reacted gel and pass it through a laboratory meat grinder with an extruder plate to break the stiff gel down into smaller particles for further treatment. Then add the sodium silicate and pass thru the meat grinder 2 more times. Then add the sodium hydroxide and pass it through the meat grinder 2 more times. Finally, add the sodium bisulfite to the gel and pass it through the meat grinder 2 more times. The gel is now ready for drying on a steam heated drum dryer. After drying, mill the dried polymer to reduce the particle size to 850 microns/106 microns.

Calculations for the Various Components in the Coating Solution (1) Polyamine:
   Amount of polyamine added is a percentage based on dry weight of superabsorbent polymer.

Example: 1 wt % polyamine for 50 grams of superabsorbent polymer: 0.5 grams dry weight polyamine in aqueous solution (percent solids of polyamine range from 8-33%)

(2) Crosslinking Agent (c.a.):

Grams of crosslinker=((g polyamine)(% solids)(mole % of c.a.)(224))/43

(3) Wetting Agent (w.a.):
If total amount of c.a. and w.a. is 2% (based on dry SAP) then the amount of w.a. will be:

Grams wetting agent=(Total c.a. and w.a.)−(c.a.)

Coating of the Superabsorbent Base Polymer

Weigh superabsorbent base polymer and place it into mini food processor (Cuisinart mini prep model #: DLC-1TX). Add required amount of propylene glycol to denacol and stir it (500 rpm) for one minute (Add denacol to the solution right before coating). Add the coating solution (dropwise) into the SAP while stirring it in a slow speed for 4-5 minutes. Coat the particle uniformly. One needs to work fast because polyamine will gel in the presence of x-linker. To avoid gelling, one could spray denacol and propylene glycol simultaneously into the SAP particles. Spread the coated polymer on a cookie sheet. Do not over load. Cure it at 120° C. for one hour. Mill and size it (180-710 μm)

Composites from Polyamine Coated Superabsorbent Polymer Particles

The procedures of forming composites are exactly written below in "Procedure of forming composites containing polyamine coated hydrogel-forming polymer"

Air-Laids from Polyamine Coated Superabsorbent Polymer Particles

The procedures of forming air-laids are exactly written below in "Procedure of forming air-laids containing polyamine coated hydrogel-forming polymer Production of Sheet Material for Air-Laid Testing Airlaid sheet materials were made on a commercial pilot line. General considerations on making airlaid product in this line with SAP is that it is difficult to make the product (especially at low basis weight, e.g., 200 gsm (grams per m$^2$) which contain in excess of 50% SAP, unless there is an increase in bicomponent fiber (from 5% to 10% by weight or more, based on the dry weight of the sheet material). Even with increasing bicomponent fiber, the upper limit is about 60% SAP as the mat does not have enough integrity to be handled and processed. Even in these cases, the tendency of the granular SAP to be lost from the web is substantial.

A product was made from 20% to 80% SAP content, with 5% bicomponent fiber, and also at 50% and 80% with no bicomponent fiber. It is not feasible to make such a structure with no bicomponent fiber, utilizing conventional SAP and no other adhesive or bonding additive.

Specifics of articles made and the basic steps that were followed are outlined as follows:

Airlaid Production at Pilot Line

Polyamine coated superabsorbent particles were used to make thin, highly densified airlaid nonwoven fabrics in roll form. Controls of conventional polyacrylate salt (sodium polyacrylate) SAP fabrics were also made when possible.

The process of forming these airlaid products involved the following steps:

A standard tissue sheet, of approximately 18-g/m$^2$ basis weight (BW) and appropriate porosity, was utilized as a carrier sheet for the subsequent mat to be supported on the forming wires. This carrier sheet was conveyed by the forming screen under several forming heads to which fluff pulp fibers, optionally bicomponent fibers, and the absorbent water-absorbent resin particles were conveyed by air, mechanically and pneumatically dispersed, and deposited upon the moving carrier sheet by a vacuum pulled from below the forming screen. The cellulosic fluff pulp fibers were generated from a fluff pulp roll that was metered to a hammermill that broke the pulp down into the component fibers and dispersed them into the conveying air. The bicomponent fibers, when used, were separated from bales, and metered into the conveying air by appropriate equipment. The granular polyamine coated superabsorbent particles were metered into the conveying air by a loss in eight feeder.

The mats were compacted by nip rollers utilizing high pressure, e.g., 5,000-10,000 psi, and at slightly elevated temperature, approximately 40-60° C., then conveyed through a thru-air oven, operating at about 135° C. The heated web was then conveyed through a calender roll, also under high pressure and slightly elevated temperature. The mat was then optionally wound or slit to obtain an absorbent fabric of desired length and width.

During the process of making the airlaid absorbent fabrics, it was demonstrated that utilizing this type absorbent material allowed a higher concentration of SAP particles to be incorporated in a lower portion of cellulosic fluff pulp fibers, from 60% to 100%, and it was also possible to do this without an increase in bicomponent (thermal-bondable) fibers, and in fact was possible without the use of any bicomponent fiber at all.

The resulting nonwoven fabrics were highly flexible, with a minimum of coarseness, had sufficient strength to handle through the process, and displayed very little SAP shakeout.

It has been found that heating a resin for a sufficient time at a sufficient temperature above the Tg (glass transition temperature) of the resin improves the absorption properties of the resin. In accordance with one important embodiment of the present invention, it has been found that when a layer of the polyamine coated superabsorbent particles is heated to at least about 50° C. during sheet material manufacture (e.g., by a heated pressure roll or oven), not only are the absorption properties improved, but the particles are strongly adhered to themselves and to any fiber or filler (e.g., clay) contained in the sheet material so that there is little to no loss of superabsorbent particles during manufacture and handling. Thus, a sheet material having 0%-40% by weight non-SAP fiber, and without added adhesive, has new and unexpected structural integrity, for the above-described uses, particularly diaper cores.

Results

Polyamine-Coated Absorbent Material Having High Values of CRC and Composites/Air Laids Made Thereof By gel coating base polymers with polyvinylamine or polyethyleneimine it is possible to control the properties of the SAP. The acquisition time and rewet values could be adjusted by percentage of amine and coating solution. The following examples based on Base Polymer (Example 1), which has been coated with different amounts of polyvinylamine PVAm. The PVAm solution which was used has larger amount of sodium formate. The existing sodium formate in the polyvinylamine-solution has been used as crosslinker. The curing temperature was 125° C. To get a manageable rewet value, the percentage of PVAm should not exceed 2%. The hydrogel-forming polymer particles are coated with about 0.1% to about 4% by weight, of the polyamine. Preferred ranges are 0.25% to 2%.

Sample 1

PVAm Solution with Equi-Molar Amount of Formate and Active Amine:

Coating of the Superabsorbent Base Polymer with PVAm:

Weigh 50 grams of superabsorbent base polymer (from example 5) and place it into mini food processor (Cuisinart mini prep model #: DLC-1TX). Add required amount of 40K polyvinylamine (PVAm), which has 8.1% solid (from BASF), to your propylene glycol (PG) and stir it (500 rpm) for couple minutes (see Table 1). Add the coating solution (dropwise) into the SAP while stirring it in a slow speed for 4-5 minutes. Coat the particle uniformly. Spread the coated polymer on a cookie sheet. Do not over load. Cure it at 120° C. for one hour. Mill and size it (180-710 μm).

TABLE 1

|  | PVAm Solution (gr.) | PG (gr.) |
|---|---|---|
| Sample 1A | 1.54 | 1.00 |
| Sample 1B | 3.09 | 1.00 |
| Sample 1C | 12.35 | 1.00 |
| Sample 1D | 18.52 | 1.00 |

| | Prod. Wt. | Rewet Under No Load (g) | | | | Acquisition Time Under Load (s) | | | |
|---|---|---|---|---|---|---|---|---|---|
| ID | | 1 | 2 | 3 | 4 | 1 | 2 | 3 | 4 |
| Sample 1A | 15.79 | 0.11 | 0.13 | 0.17 | 1.74 | 112.5 | 214.3 | 290.9 | 353.9 |
| Sample 1B | 15.9 | 0.12 | 0.06 | 0.33 | 2.82 | 95.5 | 146.5 | 212.2 | 275.2 |
| Sample 1C | 15.92 | 0.15 | 0.11 | 0.33 | 3.04 | 106.6 | 143.8 | 162.3 | 198.7 |
| Sample 1D | 15.82 | 0.1 | 0.6 | 3.4 | 9.27 | 107.0 | 85.7 | 99.0 | 110.6 |
| Comparative Example 1 | 15.96 | 0.15 | 0.09 | 0.21 | 2.28 | 113.1 | 267.5 | 368.4 | 478.7 |

| ID | AUL (0.3 psi) | CRC |
|---|---|---|
| Sample 1A | 24.6 | 26.94 |
| Sample 1B | 23.5 | 26.03 |
| Sample 1C | 16.46 | 25.13 |
| Sample 1D | 16.03 | 23.84 |

Determination of rewet and acquisition time confirm the best performance found above. If the amount of polyvinylamine is too low, only small changes in acquisition time are found compared to uncoated samples. If the amount of polyvinylamine is too high, the rewet turns to worse and the values for rewet will rise.

Further tests show, that the polyamine-coating performs the best with base polymer having a residual water content of less than 10 w %. Further comparative examples are coated base polymers, which coating has not been crosslinked, that is, the polyamine is added without crosslinker, and, coated base polymers, which show covalent bondings between core and shell because of crosslinking at temperatures of more than 150° C. (See Samples 3 and 4).

Sample 2

PVAm Solution with Reduced Sodium Formate:

Weigh 50 grams of superabsorbent base polymer (from Example 2) and place it into mini food processor (Cuisinart mini prep model #: DLC-1TX). Add required amount of PG to the required amount of 40K polyvinylamine (PVAm), which has 8.3% solid content (from BASF) and stir it (see Table 2). Add the exact amount of denacol to the above solution right before coating. Add the coating solution (dropwise) into the SAP while stirring it in a slow speed for 4-5 minutes. Coat the particle uniformly. Spread the coated polymer on a cookie sheet. Do not over load. Cure it at 120° C. for one hour. Mill and size it (180-710 μm).

TABLE 2

|  | PVAm Solution (gr.) | PG (gr.) | Denacol (gr.) |
|---|---|---|---|
| Sample 2A | 1.36 | 0.980 | 0.020 |
| Sample 2B | 2.72 | 0.039 | 0.961 |
| Sample 2C | 4.08 | 0.059 | 0.941 |
| Sample 2D | 5.43 | 0.078 | 0.922 |
| Sample 2E | 10.87 | 0.158 | 0.844 |
| Sample 2F | 10.87 | 1.00 | 0.00 |
| Sample 2G | 16.30 | 0.234 | 0.766 |
| Sample 2H | 21.74 | 0.313 | 0.687 |

| | Prod. Wt. | Rewet Under No Load (g) | | | | Acquisition Time Under Load (s) | | | |
|---|---|---|---|---|---|---|---|---|---|
| ID | | 1 | 2 | 3 | 4 | 1 | 2 | 3 | 4 |
| Sample 2F | 15.90 | 0.15 | 0.10 | 0.24 | 2.34 | 118.2 | 249.4 | 357.2 | 468.3 |
| Sample 2E | 15.92 | 0.15 | 0.11 | 0.33 | 3.04 | 106.6 | 143.8 | 162.3 | 198.7 |
| Comparative Example 1 | 15.96 | 0.15 | 0.09 | 0.21 | 2.28 | 113.1 | 267.5 | 368.4 | 478.7 |

| ID | AUL (0.3 psi) | CRC |
|---|---|---|
| Sample 2F | 15.2 | 21.2 |
| Sample 2E | 16.46 | 25.13 |

Sample 3

Moisture Reintroduction into the SAP 2300:

Dried (see Moisture Content-Weight Loss Upon Heating) the base polymer which was made according to example 1 and introduced 12 and 17% of water to make polymer with 15 and 20% moisture contents (after drying, the base polymer had about 3% retained water). These polymers were coated as in Sample 1C using 12.35 grams of PVAm solution and 1.00 gram of PG.

|  | Dried SAP (gr.) | di-H2O (gr.) |
|---|---|---|
| Sample 3A (15% Water) | 50 | 6.00 |
| Sample 3B (20% Water) | 50 | 8.50 |

| | Prod. Wt. | Rewet Under No Load (g) | | | | Acquisition Time Under Load (s) | | | |
|---|---|---|---|---|---|---|---|---|---|
| ID | | 1 | 2 | 3 | 4 | 1 | 2 | 3 | 4 |
| Sample 3A, (15 w % retained water) | 15.80 | 0.13 | 0.17 | 0.37 | 2.38 | 112.3 | 225.3 | 319.2 | 322.7 |

-continued

| | | | | | | | | |
|---|---|---|---|---|---|---|---|---|
| Sample 3B, (20 w % retained water) | 15.82 | 0.14 | 0.21 | 0.39 | 2.59 | 115.2 | 238.9 | 329.4 334.5 |
| Comparative Example 1 | 15.96 | 0.15 | 0.09 | 0.21 | 2.28 | 113.1 | 267.5 | 368.4 478.7 |

| ID | AUL (0.3 psi) | CRC |
|---|---|---|
| Sample 3A, (15 w % retained water) | 16.6 | 25.8 |
| Sample 3B, (20 w % retained water) | 17.3 | 25.5 |

Sample 4

The base polymer from Example 1 (50 grams) was coated as in Sample 2E using 10.87 grams of 8.3% PVAm, 0.158 grams PG and 0.844 grams EDDGE. The cure temperature was 150° C. instead of 120° C.

| ID | Prod. Wt. | Rewet Under No Load (g) | | | | Acquisition Time Under Load (s) | | | |
|---|---|---|---|---|---|---|---|---|---|
| | | 1 | 2 | 3 | 4 | 1 | 2 | 3 | 4 |
| Sample 4A, crosslinking at 150° C. | 15.90 | 0.13 | 0.08 | 0.19 | 2.48 | 114.8 | 318.4 | 423.8 | 633.9 |
| Comparative Example 1 | 15.96 | 0.15 | 0.09 | 0.21 | 2.28 | 113.1 | 267.5 | 368.4 | 478.7 |

| ID | AUL (0.3 psi) | CRC |
|---|---|---|
| Sample 4A, crosslinking at 150° C. | 18.3 | 26.8 |

Base Polymer Containing Silicate as Crosslinker

A 10 L capacity polyethylene vessel, well insulated by foamed polymer material, is charged with 3400 g of demineralized water and 1400 g of acrylic acid. 6.3 g of pentaerythritol triallyl ether are then added as copolymerization crosslinker. At a temperature of 4° C., the initiators, consisting of 2.2 g of 2,2'-azobisamidinopropane dihydrochloride, dissolved in 25 g of demineralized water, 4 g of potassium peroxodisulfate, dissolved in 150 g of demineralized water, and 0.4 g of ascorbic acid, dissolved in 25 g of demineralized water, are added in succession stirred in. The reaction solution is then left to stand without stirring, and the temperature of the polymerization rises to about 94° C. A solid gel is obtained, and this gel is subsequently mechanically comminuted. A mixture of 652.4 g of sodium silicate solution containing 26.8 wt.-% SiO$_2$ and 10.55 wt.-% Na$_2$O and 973.0 g of an aqueous 50 wt.-% solution of NaOH is added to the gel and mixed in by putting the gel two times through a kitchen meat chopper. The gel is then dried, ground and classified to a particle size distribution of 100-850 μm.

1 kg of the base polymer is sprayed in a plowshare mixer with the following solutions (simultaneously, but via two nozzles):

| Example | Nozzle 1 | Nozzle 2 |
|---|---|---|
| 1 | 20 g of poly vinyl amine solution* | 0.9 g of ethylene glycol bisglycidyl ether<br>15 g of propylene glycol<br>15 g of demineralized water |
| 2 | 12.5 g of poly vinyl amine solution* | 0.05 g of ethylene glycol bisglycidyl ether<br>15 g of propylene glycol<br>15 g of demineralized water |
| 3 | 5.0 g of poly vinyl amine solution* | 0.3 g of ethylene glycol bisglycidyl ether<br>15 g of propylene glycol<br>15 g of demineralized water |
| 4 | 20 g of poly ethylene imine solution** | 1.5 g of ethylene glycol bisglycidyl ether<br>15 g of propylene glycol<br>15 g of demineralized water |
| 5 | 20 g of poly ethylene imine solution** | 0.3 g of ethylene glycol bisglycidyl ether<br>15 g of propylene glycol<br>15 g of demineralized water |
| 6 | 12.5 g of poly ethylene imine solution** | 0.05 g of ethylene glycol bisglycidyl ether<br>15 g of propylene glycol<br>15 g of demineralized water |

*poly vinyl amine solution: 25% strength by weight aqueous solution of poly vinyl amine (K value of 30)
**poly ethylene imine solution: Polymin G 100 (trade product from BASF AG, 50% strength by weight aqueous solution of poly ethylene imine)

The mixtures are then heated in a laboratory drying oven at 100° C. for 60 minutes. The products described herein have the following properties:

| Sample | CRC | AUL 0.01 psi | AUL 0.29 psi | AUL 0.57 psi | AUL 0.90 psi | PAI |
|---|---|---|---|---|---|---|
| 1 | 26.1 | 44.5 | 27.2 | 17.8 | 11.9 | 101.4 |
| 2 | 27.1 | 42.3 | 22.9 | 17.1 | 13.1 | 95.4 |
| 3 | 25.0 | 40.2 | 25.8 | 17.9 | 15.9 | 99.8 |
| 4 | 25.9 | 40.7 | 26.1 | 21.4 | 11.4 | 99.6 |
| 5 | 28.1 | 38.2 | 26.5 | 11.4 | 8.9 | 85.0 |
| 6 | 30.1 | 41.7 | 21.2 | 9.4 | 7.4 | 79.7 |

| Sample | Rewet Under No Load (g) | | | | Acquisition Time Under Load (s) | | | |
|---|---|---|---|---|---|---|---|---|
| | 1 | 2 | 3 | 4 | 1 | 2 | 3 | 4 |
| 1 | 0.09 | 0.12 | 0.15 | 1.6 | 107.6 | 87.9 | 95.3 | 104.7 |
| 2 | 0.1 | 0.19 | 0.19 | 3.5 | 147.3 | 107.3 | 117.9 | 124.1 |
| 3 | 0.07 | 0.23 | 0.26 | 9.5 | 158.9 | 245.5 | 273.8 | 258.4 |
| 4 | 0.09 | 0.13 | 0.18 | 1.26 | 119.7 | 104.3 | 113.5 | 110.7 |
| 5 | 0.03 | 0.16 | 0.17 | 1.88 | 129.8 | 126.2 | 109.9 | 113.4 |
| 6 | 0.05 | 0.18 | 0.19 | 2.97 | 147.9 | 154.2 | 162.0 | 165.4 |

Composites or Air-Laids Containing Polyamine Coated Superabsorbent Polymer with High CRC Composites or air-laids containing polyamine coated superabsorbent polymer with high CRC show an excellent acquisition behaviour as well as high absorptive capacities and low rewets at the same time. Polyamine coated superabsorbent polymers showing improved acquisition rates compared with uncoated polymers of same CRC or SFC values.

The following superabsorbent polymers were tested in 60/40 cores (SAP/Fluff). The conditions are the following: 10.000 lb compression, 12×21 cm core, 9 g SAP/6 g Fluff.

The following tables show comparisons of the acquisition behaviour of conventional SAP and polyamine coated SAP Conventional Superabsorbent Polymer

|  |  |  | Acquisition Rate (ml/s) | | | |
|---|---|---|---|---|---|---|
| Sample | SFC | CRC (g/g) | 1 (40 ml) | 2 (40 ml) | 3 (40 ml) | 4 (40 ml) |
| Comp. Ex 4 | 0 | 32.2 | 0.414 | 0.131 | 0.073 | 0.060 |
| Comp. Ex 2 | 27.8 | 28.3 | 0.363 | 0.139 | 0.103 | 0.083 |
| Comp. Ex 1 | 77.3 | 26.8 | 0.386 | 0.166 | 0.116 | 0.098 |
| Comp. Ex 3 | 164.6 | 23.6 | 0.476 | 0.245 | 0.178 | 0.143 |

Polyamine Coated Superabsorbent Polymer

|  |  |  |  | Acquisition Rate (ml/s) | | | |
|---|---|---|---|---|---|---|---|
| Sample | | SFC | CRC (g/g) | 1 (40 ml) | 2 (40 ml) | 3 (40 ml) | 4 (40 ml) |
| 1 | 0% denacol | 5.0 | 25.12 | 0.405 | 0.251 | 0.214 | 0.167 |
| 2 | 2% denacol | 65.8 | 22.84 | 0.470 | 0.352 | 0.308 | 0.259 |
| 3 | 3% denacol | 84.7 | 21.97 | 0.521 | 0.404 | 0.351 | 0.292 |
| 4 | 4% denacol | 50.4 | 21.70 | 0.518 | 0.382 | 0.301 | 0.271 |
| 5 | 0% denacol | 6.4 | 33.94 | 0.246 | 0.190 | 0.147 | 0.122 |
| 6 | 3% denacol | 39.5 | 26.36 | 0.434 | 0.273 | 0.238 | 0.201 |
| 7 |  | 31.0 | 22.45 | 0.553 | 0.339 | 0.255 | 0.218 |

Comparing conventional superabsorber and superabsorber of the invention, it was found that superabsorber of the invention is superior regarding aquisition times, if superabsorbers with similar sfc or CRC are compared.

The Fluff used for the examples of this chapter contained bicomponent fibers. For showing the improved adhesion of polyamine coated superabsorbents, comparative examples were exhibited with Fluff containing no bicomponent fibers. Composites or air-laids made thereof have unexpectedly high loadings of superabsorbent polymers and can be manufactured without bicomponent fiber or binder while providing excellent structural integrity with little to no shakeout or loss of superabsorbent particles from the sheet material.

Dry and Wet Integrity:

By looking at average force it is obvious that dry and wet integrity of the polyamine coated SAP are superior than the conventional SAP.

TABLE 3

Dry-Integrity

| Sample ID | Product Height mm | Product Weight g | Distance 1 mm Distance 1 | Force 1 g Force 1 | Area-FD 1:2 g · mm Area-FD 1:2 | Grad.-FD 1:2 g/mm Grad.-FD 1:2 | Ave. Force |
|---|---|---|---|---|---|---|---|
| 1, 0.25% Unpure PVAm | 100.00 | 5.81 | 12.98 | 1336.44 | 7326.85 | 102.42 |  |
| 1, 0.25% Unpure PVAm | 100.00 | 6.09 | 11.56 | 1443.89 | 6245.67 | 124.28 | 1390.16 |
| 2, 0.5% Unpure PVAm | 100.00 | 6.56 | 14.93 | 1257.31 | 8422.91 | 83.76 |  |
| 2, 0.5% Unpure PVAm | 100.00 | 6.48 | 12.24 | 1476.48 | 7879.95 | 119.95 | 1366.90 |
| 3, 1% Unpure PVAm | 100.00 | 6.94 | 12.26 | 1523.90 | 8495.88 | 123.47 |  |
| 3, 1% Unpure PVAm | 100.00 | 6.54 | 12.44 | 1431.81 | 6713.01 | 114.41 | 1477.86 |
| 4, 0.25% Pure PVAm | 100.00 | 6.11 | 11.33 | 1171.76 | 5082.21 | 102.85 |  |
| 4, 0.25% Pure PVAm | 100.00 | 6.81 | 12.86 | 1625.18 | 9345.79 | 125.59 | 1398.47 |
| 5, 0.5% Pure PVAm | 100.00 | 6.31 | 16.39 | 1182.55 | 9923.70 | 71.71 |  |
| 5, 0.5% Pure PVAm | 100.00 | 6.86 | 13.07 | 1617.16 | 10115.69 | 123.05 | 1399.85 |
| 6, 1% Pure PVAm | 100.00 | 6.15 | 12.13 | 1228.91 | 6755.07 | 100.65 |  |
| 6, 1% Pure PVAm | 100.00 | 6.84 | 12.04 | 1776.73 | 8939.65 | 146.53 | 1502.82 |
| 7, Neut. W/H3PO4 | 100.00 | 6.40 | 13.59 | 1440.30 | 8190.18 | 105.46 |  |
| 7, Neut. W/H3PO4 | 100.00 | 6.72 | 13.62 | 1623.16 | 9636.16 | 118.69 | 1531.73 |
| Comp. Example 1 | 100.00 | 6.31 | 11.62 | 1173.44 | 5070.31 | 100.37 |  |
| Comp. Example 1 | 100.00 | 6.51 | 15.23 | 1512.95 | 11900.31 | 98.79 | 1343.20 |

Wet-Integrity

| Sample | Product Weight g | Distance 1 mm Distance 1 | Force 1 g Force 1 | Area-FD 1:2 g · mm Area-FD 1:2 | Grad.-FD 1:2 g/mm Grad.-FD 1:2 | Ave. Force |
|---|---|---|---|---|---|---|
| 1, 0.25% Unpure PVAm | 6.29 | 15.32 | 331.04 | 2487.86 | 21.14 |  |
| 1, 0.25% Unpure PVAm | 6.19 | 12.80 | 260.53 | 1754.44 | 19.77 | 295.78 |
| 2, 0.5% Unpure PVAm | 5.92 | 15.69 | 308.98 | 2479.01 | 19.26 |  |
| 2, 0.5% Unpure PVAm | 6.47 | 16.48 | 325.14 | 2737.33 | 19.26 | 317.06 |
| 3, 1% Unpure PVAm | 6.11 | 16.15 | 301.01 | 2679.72 | 18.15 |  |
| 3, 1% Unpure PVAm | 6.60 | 15.23 | 347.78 | 2530.93 | 22.39 | 324.39 |
| 4, 0.25% Pure PVAm | 6.50 | 15.09 | 304.69 | 2206.73 | 19.78 |  |
| 4, 0.25% Pure PVAm | 6.24 | 13.86 | 274.81 | 1881.91 | 19.40 | 289.75 |
| 5, 0.5% Pure PVAm | 6.13 | 14.80 | 276.31 | 2128.27 | 18.24 |  |
| 5, 0.5% Pure PVAm | 6.36 | 14.44 | 314.14 | 2234.10 | 21.26 | 295.22 |
| 6, 1% Pure PVAm | 6.13 | 16.09 | 285.35 | 2383.64 | 17.30 |  |
| 6, 1% Pure PVAm | 6.62 | 14.23 | 303.21 | 2028.34 | 20.98 | 294.28 |
| 7, Neut. W/H3PO4 | 6.29 | 14.90 | 245.88 | 2021.67 | 16.05 |  |
| 7, Neut. W/H3PO4 | 6.75 | 14.30 | 330.81 | 2263.92 | 22.60 | 288.35 |

TABLE 3-continued

| | | | | | | |
|---|---|---|---|---|---|---|
| Comp. Example 1 | 6.22 | 13.66 | 252.51 | 1676.20 | 18.04 | |
| Comp. Example 1 | 6.32 | 15.82 | 292.73 | 2425.26 | 18.06 | 272.62 |

Summary of the Results

It could be shown that the hydrogel-forming particles performs the best, which were coated with cationic compounds as polyvinylamines or polyethylene imines. Preferred are the base polymers, which are—even only partially—crosslinked with silica/aluminates/alumosilicates. Said base polymers show the best acquisition times and rewets after coating with cationic compound.

Comparative examples show, that a crosslinker has to be added to the cationic compound to get superior acquisition times.

Further examples show that the performance of control samples which were coated with polyamines at temperatures >150° C. was even worse. At that temperatures covalent bondings of polyamine onto the superabsorber surface are present. According to our invention we chose temperatures of about 100° C. to prevent covalent bondings.

Further results show that there are also some different results using base polymer which is surface crosslinked compared to base polymers without surface crosslinking. The coating of surface crosslinked base polymers leads to superabsorbent particles which show high AUL values and improved performance; but on the other hand their performance (acquisition time, rewet) is quite bad. According to our invention, we use base polymer without surface crosslinking. Thus the degree of crosslinking is lower, and therefore the absorption capacities somewhat higher.

It could be shown that composites or air-laids comprising hydrogel-forming particles which were coated with cationic compounds as polyvinylamines or polyethylene imines performs the best.

The above data show that the composites or air-laids of the present invention have excellent structural integrity in a non-woven fabric utilizing only polyamine coated superabsorbent material and a small amount of cellulosic or other comparable fibers/carrier, even with no or an optional small proportion of other binding material, such as bicomponent fiber. The sheet materials provide enhanced economics, feel and performance. Without the need for binder, manufacturing costs are lower as well as enhanced absorbency upon hydration by aqueous fluids in use.

The minimum of shakeout and loss of the granular absorbent resin particles is of significant importance to manufacture, conversion, and use of the absorbent fabric.

Overall, the data presented demonstrate that a diaper core of the present invention, containing an composites or air-laids of polyamine coated superabsorbent material, maintains a flat, essentially constant, or surprisingly a decreased, acquisition time over five insults, whereas prior cores demonstrate an increased acquisition time as the number of insults increase.

Polyamine-coated absorbent material having improved permeability and composites/air laids made thereof.

The following examples concern coated absorbent particles having improved permeability. Said absorbent particles exhibit improved permeability without tendency to gel-blocking by unchanged high CRC. Composites or air-laids made thereof show an improved permeability.

Dependence of Crosslinker Content, Procedure and Reaction Temperatures

Base Polymer Preparation: (Sample 1 to 7)

A 10 L capacity polyethylene vessel, well insulated by foamed polymer material, is charged with 3400 g of demineralized water and 1400 g of acrylic acid. 14.0 g of pentaerythritol triallyl ether and 75.0 g of a 15% strength by weight aqueous solution of a polyamidoamine-epichlorhydrin adduct (RETEN 204 LS from Hercules) are then added as crosslinker. At a temperature of 4° C., the initiators, consisting of 2.2 g of 2,2'-azobisamidinopropane dihydrochloride, dissolved in 25 g of demineralized water, 4 g of potassium peroxodisulfate, dissolved in 150 g of demineralized water, and 0.4 g of ascorbic acid, dissolved in 25 g of demineralized water, are added in succession stirred in. The reaction solution is then left to stand without stirring, and the temperature of the polymerization rises to about 93° C. A solid gel is obtained, and this gel is subsequently mechanically comminuted and adjusted to pH 6.0 by addition of 50% strength by weight sodium hydroxide solution The gel is then dried, ground and classified to a particle size distribution of 100-850 μm.

Surface Crosslinking Examples:

1 kg of the base polymer is sprayed in a plowshare mixer with the following solutions (simultaneously, but via two nozzles):

| Sample | Nozzle 1 | Nozzle 2 |
|---|---|---|
| 1 | 20 g of poly vinyl amine solution* | 2.0 g of ethylene glycol bisglycidyl ether<br>10 g of propylene glycol<br>20 g of demineralized water |
| 2 | 12.5 g of poly vinyl amine solution* | 1.5 g of ethylene glycol bisglycidyl ether<br>10 g of propylene glycol<br>20 g of demineralized water |
| 3 | 20 g of poly ethylene imine solution** | 1.0 g of ethylene glycol bisglycidyl ether<br>10 g of propylene glycol<br>20 g of demineralized water |
| 4 | 20 g of poly ethylene imine solution** | 2.0 g of ethylene glycol bisglycidyl ether<br>10 g of propylene glycol<br>20 g of demineralized water |
| 5 | 20 g of poly ethylene imine solution** | 1.0 g of ethylene glycol bisglycidyl ether<br>10 g of propylene glycol<br>20 g of demineralized water |
| 6 | 10.0 g of poly ethylene imine solution** | 2.0 g of ethylene glycol bisglycidyl ether<br>10 g of propylene glycol<br>20 g of demineralized water |
| 7 | — | 0.2 g of ethylene glycol bisglycidyl ether<br>10 g of propylene glycol<br>20 g of demineralized water |

*poly vinyl amine solution: 25% strength by weight aqueous solution of poly vinyl amine (K value of 30)
**poly ethylene imine solution: Polymin G 100 (trade product from BASF AG, 50% strength by weight aqueous solution of poly ethylene imine)

The mixtures are then heated in a laboratory drying oven at 100° C. for 60 minutes. The products described herein (all of white color) have the properties shown in table 1.

Comparative Sample (Sample 8 to 10)

Sample 8

1 kg of the base polymer is sprayed in a plowshare mixer with a solution consisting of 2.0 g of ethylene glycol bisglycidyl ether, 10 g of propylene glycol and 20 g of demineralized water. The mixture is the heated in a laboratory drying oven at 100° C. for 60 minutes. The dried product is then placed again in a plowshare mixer and sprayed with a mixture consisting of 20 g of a poly vinyl amine solution (25% strength by weight aqueous solution of poly vinyl amine, K value of 30) and 10 g of demineralized water. The mixture is then heated in a laboratory drying oven at 100° C. for 60 minutes.

Sample 9

1 kg of the base polymer is sprayed in a plowshare mixer with a solution consisting of 20 g of a poly vinyl amine solution (25% strength by weight aqueous solution of poly vinyl amine, K value of 30), 10 g of propylene glycol and 20 g of demineralized water. The mixture is the heated in a laboratory drying oven at 100° C. for 60 minutes.

Sample 10

1 kg of the base polymer is sprayed in a plowshare mixer with a solution consisting of 20 g of a poly vinyl amine solution (25% strength by weight aqueous solution of poly vinyl amine, K value of 30), 10 g of propylene glycol and 20 g of demineralized water. The mixture is the heated in a laboratory drying oven at 180° C. for 60 minutes. A product with yellow-brown color is obtained.

TABLE 1

| Sample | CRC | GBP |
| --- | --- | --- |
| 1 | 20.4 g/g | 2150 |
| 2 | 23.0 g/g | 1100 |
| 3 | 22.8 g/g | 1150 |
| 4 | 20.3 g/g | 1580 |
| 5 | 21.5 g/g | 1080 |
| 6 | 22.1 g/g | 950 |
| 7* | 22.6 g/g | 390 |
| 8* | 20.8 g/g | 450 |
| 9* | 24.7 g/g | 120 |
| 10* | 14.2 g/g | 1120 |

*Comparative example

Despite there are only small differences in CRC for the different examples (except example 10) the method of coating and the amount of crosslinker in the coating solution determines the GBP. As found by our experiments, the amount of crosslinker in the amount of polyamine to SAP should be in the range of 2 w % to 4 w % referred to the total amount of coating solution to give good results in GBP. Further—as seen from example 8—the heating process has to be after completion of addition of both components of coating. Example 10 shows us that the best products can be get by temperatures of lower than 150° C., preferably lower than 100° C. Otherwise covalent bondings will strongly decrease the GBP results.

Comparison of Polyamine Surface Crosslinking with Conventional Surface Crosslinking

TABLE 2

The base polymer was prepared according to Example 3 and was coated with standard denacol coating.
Standard Denacol EX-810 Surface Crosslinking

| Sample | Denacol, ppm | CR | CRC | AUL 0.7 | GBP |
| --- | --- | --- | --- | --- | --- |
| 1 | 600 | 0.04 | 19.8 | 22.8 | 336.35 |
| 2 | 1000 | 0.04 | 19.5 | 22.1 | 356.97 |
| 3 | 2000 | 0.04 | 19.2 | 22.1 | 384.09 |
| 4 | 3000 | 0.04 | 19.2 | 22.2 | 333.34 |

TABLE 3

The base polymer was prepared according to Example 3 and was coated with polyamine. The differences in the samples lies in the % of denacol which was used to make the base polymers.
Polyamine Surface Crosslinking

| Sample | CR | CRC | AUL 0.7 | GBP |
| --- | --- | --- | --- | --- |
| 1 | 0.0550 | 20.3 | 22.4 | 2299.6 |
| 2 | 0.0628 | 19.6 | 22.4 | 2022.6 |
| 3 | 0.0630 | 19.4 | 21.4 | 2022.3 |
| 4 | 0.0550 | 19.8 | 21 | 1645.1 |
| 5 | 0.0550 | 20 | 21.4 | 2067.6 |
| 6 | 0.0550 | 20.1 | 20.4 | 1710.2 |
| 7 | 0.0550 | 19.6 | 21 | 1995.9 |
| 8 | 0.0550 | 19.8 | 20.9 | 1710 |
| 9 | 0.0550 | 19.3 | 20.8 | 1978.2 |
| 10 | 0.0550 | 19.3 | 20.6 | 2119.2 |
| 11 | 0.0550 | 18.8 | 22.0 | 1822.8 |
| 12 | 0.0550 | 19.1 | 21.1 | 2292.6 |
| 13 | 0.0550 | 19.7 | 18.4 | 1821.0 |
| 14 | 0.0628 | 18.8 | 18.2 | 2015.3 |
| 15 | 0.0550 | 19.7 | 18.3 | 1930.4 |
| 16 | 0.0628 | 19.3 | 18.3 | 2045.7 |
| 17 | 0.0550 | 19.6 | 18.6 | 1819.0 |
| 18 | 0.0628 | 18.9 | 17.6 | 1945.6 |
| 19 | 0.0550 | 19.1 | 16.4 | 2227.1 |
| 20 | 0.0628 | 18.5 | 17.7 | 2048.8 |
| 21 | 0.0550 | 19.5 | 18.8 | 1827.6 |
| 22 | 0.0628 | 18.6 | 18.8 | 2217.3 |
| 23 | 0.0550 | 19.4 | 18.7 | 1690.2 |
| 24 | 0.0628 | 18.6 | 19.0 | 1782.6 |
| 25 | 0.0550 | 19.6 | 18.5 | 1764.4 |
| 26 | 0.0628 | 19.1 | 18.7 | 2033.4 |
| 27 | 0.0550 | 19.7 | 18.4 | 2031.5 |
| 28 | 0.0628 | 19.3 | 17.9 | 2172.2 |
| 29 | 0.0550 | 21.4 | 17.8 | 1910.7 |
| 30 | 0.0628 | 20.4 | 17.7 | 1728.6 |
| 31 | 0.0550 | 20.3 | 21.6 | 2249.2 |
| 32 | 0.0628 | 19.9 | 21.4 | 1941.4 |
| 33 | 0.0550 | 20.2 | 21.7 | 1982.6 |
| 34 | 0.0628 | 19.8 | 22.3 | 1975.9 |
| 35 | 0.0550 | 20.4 | 21.1 | 2155.7 |

Table 3 offers easily that the GBP in the case of polyamine surface crosslinking is much higher than in the case of conventional surface crosslinking.

5.4.2.3 Influence of the Amount of Crosslinking Agent in the Polyamine Coating Solution on the Absorption Profile of the Superabsorbent Particle Compared is the coating of conventional superabsorbent polymers with that of high permeability superabsorbent polymers and its effect in a diaper core environment (table 4 and 5).

TABLE 4

Base polymer prepared by the method of Example 1 (2300)
Polyethyleneimine (33 wt % solids, Mw = 70,000)
Crosslinker: Ethylene glycol diglycidyl ether
Wetting Agent: Propylene glycol 125° C. 1 hr

| Sample | Sample | Coating Ratio | AUL 0.7 1 hr | CRC | SFC |
|---|---|---|---|---|---|
| 1 | Comparative Example 1 | 0.0400 | 24.3 | 27.4 | 17.8 |
| 2 | PEI 1% - 1 mole % Crosslinker | 0.0734 | 19.5 | 27.7 | 14.0 |
| 3 | PEI 1% - 3 mole % Crosslinker | 0.0734 | 20.2 | 27.2 | 13.8 |
| 4 | PEI 1% - 5 mole % Crosslinker | 0.0734 | 19.1 | 26.9 | 11.7 |
| 5 | PEI 1% - 10 mole % Crosslinker | 0.0734 | 20.2 | 26.8 | 19.9 |

4-40 ml 0.9% NaCl insults

| | Acquisition Time (sec) | | | | Acquisition Rate | | | | Rewet (g) | | | |
|---|---|---|---|---|---|---|---|---|---|---|---|---|
| Sample | 1 | 2 | 3 | 4 | 1 | 2 | 3 | 4 | 1 | 2 | 3 | 4 |
| 1 | 140.0 | 282.5 | 423.0 | 497.5 | 0.29 | 0.14 | 0.09 | 0.08 | 0.11 | 0.14 | 0.28 | 1.9 |
| 4 | 76.6 | 141.0 | 169.4 | 204.8 | 0.52 | 0.28 | 0.24 | 0.20 | 0.08 | 0.07 | 0.30 | 2.7 |
| 5 | 84.1 | 156.2 | 200.8 | 231.7 | 0.48 | 0.26 | 0.20 | 0.17 | 0.06 | 0.07 | 0.16 | 2.0 |

TABLE 5

Base polymer prepared by the method of Example 3 (2260)
Polyethyleneimine (33 wt % solids, Mw = 70,000)
Crosslinker: Ethylene glycol diglycidylether
Wetting Agent: Propylene glycol 125° C. 1 hr

| Sample | Sample | Coating Ratio | AUL 0.7 1 hr | CRC | SFC |
|---|---|---|---|---|---|
| 1 | Comparative Example 3 | 0.050 | 24.1 | 21.1 | 152.0 |
| 2 | PEI 1% - 5 mole % Crosslinker | 0.073 | 22.0 | 19.5 | 648.8 |
| 3 | PEI 1% - 10 mole % Crosslinker | 0.073 | 20.8 | 18.8 | 513.5 |

4-40 ml 0.9% NaCl insults

| | Acquisition Time (sec) | | | | Acquisition Rate | | | | Rewet (g) | | | |
|---|---|---|---|---|---|---|---|---|---|---|---|---|
| Sample | 1 | 2 | 3 | 4 | 1 | 2 | 3 | 4 | 1 | 2 | 3 | 4 |
| 1 | 78.7 | 160.5 | 203.4 | 259.5 | 0.51 | 0.25 | 0.20 | 0.15 | 0.12 | 0.14 | 0.39 | 3.85 |
| 2 | 68.4 | 66.4 | 70.8 | 86.7 | 0.58 | 0.60 | 0.56 | 0.46 | 0.08 | 0.23 | 1.62 | 17.70 |
| 3 | 65.0 | 63.3 | 72.7 | 95.4 | 0.62 | 0.63 | 0.55 | 0.42 | 0.16 | 0.15 | 1.36 | 13.87 |

Generally coating superabsorbent particles with a polyethyleneimine solution has a substantial effect on the polymer's performance in a diaper core. However the benefits are much greater in the case of coating high permeability superabsorbent polymer. Although the absorption (AUL) and permeability (SFC) of the polymer decreases above a certain amount of crosslinker, the performance in terms of acquisition rate is superior to that of conventional superabsorbent polymer. Obviously, a crosslinker content of 10 mol % is the above limit where there is no further increase of permeability. Otherwise, even a very low levels of addition of polyethyleneimine, the aquisition rate increase in observed. As the polyethyleneimine levels increase, the rewet (g) data maintain the low values as seen with the control for the 1st, 2nd, 3rd insults.

Effect of coating a superabsorbent polymer with a single coating solution that contains both an amine and a crosslinker. Compared is the coating of conventional superabsorbent polymers with that of high permeability superabsorbent polymers and its effect in a diaper core environment (table 6 and 7).

TABLE 6

Base polymer prepared by the method of Example 1 (2300)
Polyethyleneimine (33 wt % solids, Mw = 70,000)
Crosslinker: Ethylene glycol diglycidylether
Wetting Agent: Propylene glycol 125° C. 1 hr

| Sample | Sample | Coating Ratio | AUL 0.7 1 hr | CRC | SFC | PAI |
|---|---|---|---|---|---|---|
| 1 | Comparative Example 1 | 0.0400 | 24.3 | 27.4 | 17.8 | |
| 2 | PEI, 0.05% | 0.0420 | 10.6 | 32.7 | 0 | |
| 3 | PEI, 0.1% | 0.0430 | 10.4 | 32.3 | 0 | |
| 4 | PEI, 0.15% | 0.0450 | 10.9 | 31.6 | 0 | 76.0 |
| 5 | PEI, 0.25% | 0.0480 | 10.5 | 31.6 | 0 | 78.4 |
| 6 | PEI, 0.5% | 0.0550 | 17.2 | 29.7 | 4.07 | 95.0 |
| 7 | PEI, 0.75% | 0.0628 | 17.5 | 28.1 | 6.40 | |
| 8 | PEI, 1% | 0.0630 | 17.4 | 27.6 | 4.90 | |
| 9 | PEI, 2% | 0.1000 | 19.0 | 27.1 | 11.20 | |
| 10 | PEI, 3% | 0.1310 | 19.4 | 28.0 | 9.80 | |
| 11 | PEI, 4% | 0.1600 | 19.4 | 27.8 | 13.90 | |

TABLE 6-continued

Base polymer prepared by the method of Example 1 (2300)
Polyethyleneimine (33 wt % solids, Mw = 70,000)
Crosslinker: Ethylene glycol diglycidylether
Wetting Agent: Propylene glycol 125° C. 1 hr

|  |  | 4-40 ml 0.9% NaCl insults | | | | | | | |
|---|---|---|---|---|---|---|---|---|---|
|  | Coat- | Acquisition Time (sec) | | | | Acquisition Rate | | | |
| Sample | ing | 1 | 2 | 3 | 4 | 1 | 2 | 3 | 4 |
| 1-Comp. Ex 1 | 0 | 140.0 | 382.5 | 423.0 | 497.5 | 0.29 | 0.10 | 0.09 | 0.08 |
| 3 | 0.1 | 230.8 | 639.4 | 700.0 | 809.7 | 0.17 | 0.06 | 0.06 | 0.05 |
| 4 | 0.15 | 109.1 | 205.0 | 244.8 | 258.0 | 0.37 | 0.20 | 0.16 | 0.16 |
| 5 | 0.25 | 128.9 | 261.5 | 336.3 | 369.8 | 0.31 | 0.15 | 0.12 | 0.11 |
| 6 | 0.5 | 89.8 | 162.1 | 188.2 | 213.4 | 0.45 | 0.25 | 0.21 | 0.19 |
| 7 | 0.75 | 93.4 | 176.4 | 250.4 | 300.9 | 0.43 | 0.23 | 0.16 | 0.13 |
| 8 | 1 | 85.9 | 200.7 | 254.6 | 299.0 | 0.47 | 0.20 | 0.16 | 0.13 |
| 9 | 2 | 87.7 | 161.3 | 191.8 | 236.1 | 0.46 | 0.25 | 0.21 | 0.17 |
| 10 | 3 | 89.0 | 231.3 | 285.1 | 371.8 | 0.45 | 0.17 | 0.14 | 0.11 |
| 11 | 4 | 84.7 | 173.5 | 235.9 | 274.4 | 0.47 | 0.23 | 0.17 | 0.15 |

|  |  | 4-40 ml 0.9% NaCl insults Rewet (g) | | | |
|---|---|---|---|---|---|
| Sample | Coating | 1 | 2 | 3 | 4 |
| 1-Comp. Ex 1 | 0 | 0.11 | 0.14 | 0.28 | 1.90 |
| 3 | 0.1 | 0.17 | 0.31 | 1.13 | 2.25 |
| 4 | 0.15 | 0.27 | 0.16 | 0.42 | 1.86 |
| 5 | 0.25 | 0.09 | 0.15 | 0.73 | 2.39 |
| 6 | 0.5 | 0.12 | 0.15 | 0.40 | 1.56 |
| 7 | 0.75 | 0.10 | 0.17 | 0.60 | 2.87 |
| 8 | 1 | 0.10 | 0.12 | 0.24 | 1.84 |
| 9 | 2 | 0.12 | 0.16 | 0.41 | 3.30 |
| 10 | 3 | 0.11 | 0.10 | 0.15 | 1.40 |
| 11 | 4 | 0.12 | 0.13 | 0.24 | 2.98 |

TABLE 7

Base polymer prepared by the method of Example 3 (2260)
Polyethyleneimine (33 wt % solids, Mw = 70,000)
Crosslinker: Ethylene glycol diglycidylether
Wetting Agent: Propylene glycol 125° C. 1 hr

| Sample | Sample | Coating Ratio | AUL 0.7 1 hr | CRC | SFC |
|---|---|---|---|---|---|
| 1 | Comparative Example 3 | 0.050 | 24.1 | 21.1 | 152.0 |
| 2 | PEI 0.25% Coated HP SAP | 0.050 | 21.8 | 19.9 | 365.3 |
| 3 | PEI 0.5% Coated HP SAP | 0.057 | 21.6 | 19.1 | 733.6 |
| 4 | PEI 0.75% Coated HP SAP | 0.065 | 21.7 | 18.6 | 713.6 |
| 5 | PEI 1% Coated HP SAP | 0.073 | 22.0 | 19.5 | 648.8 |
| 6 | PEI 2% Coated HP SAP | 0.107 | 21.5 | 17.4 | 661.4 |
| 7 | PEI 3% Coated HP SAP | 0.140 | 21.5 | 17.1 | 687.6 |
| 8 | PEI 4% Coated HP SAP | 0.173 | 19.5 | 16.7 | 722.3 |

|  | 4-40 ml 0.9% NaCl insults | | | | | | | |
|---|---|---|---|---|---|---|---|---|
|  | Acquisition Time (sec) | | | | Acquisition Rate | | | |
| Sample | 1 | 2 | 3 | 4 | 1 | 2 | 3 | 4 |
| 1-Comp. Ex 3 | 78.7 | 160.5 | 203.4 | 259.5 | 0.51 | 0.25 | 0.20 | 0.15 |
| 2 | 61.1 | 67.4 | 84.4 | 101.0 | 0.65 | 0.59 | 0.47 | 0.40 |
| 3 | 62.1 | 74.4 | 77.0 | 90.2 | 0.64 | 0.54 | 0.52 | 0.44 |
| 4 | 60.8 | 66.3 | 69.7 | 85.0 | 0.66 | 0.60 | 0.57 | 0.47 |
| 5 | 59.5 | 61.0 | 65.2 | 78.8 | 0.67 | 0.66 | 0.61 | 0.51 |
| 6 | 57.8 | 78.5 | 79.6 | 87.3 | 0.69 | 0.51 | 0.50 | 0.46 |
| 7 | 55.8 | 56.4 | 76.2 | 87.0 | 0.72 | 0.71 | 0.52 | 0.46 |
| 8 | 55.4 | 65.3 | 70.1 | 89.2 | 0.72 | 0.61 | 0.57 | 0.45 |

TABLE 7-continued

Base polymer prepared by the method of Example 3 (2260)
Polyethyleneimine (33 wt % solids, Mw = 70,000)
Crosslinker: Ethylene glycol diglycidylether
Wetting Agent: Propylene glycol 125° C. 1 hr

|  | 4-40 ml 0.9% NaCl insults Rewet (g) | | | |
|---|---|---|---|---|
| Sample | 1 | 2 | 3 | 4 |
| 1-Comp. Ex 3 | 0.12 | 0.14 | 0.39 | 3.85 |
| 2 | 0.17 | 0.12 | 0.40 | 9.10 |
| 3 | 0.11 | 0.08 | 0.22 | 7.90 |
| 4 | 0.12 | 0.11 | 0.48 | 7.70 |
| 5 | 0.07 | 0.10 | 0.47 | 12.10 |
| 6 | 0.13 | 0.23 | 1.00 | 9.50 |
| 7 | 0.15 | 0.34 | 1.69 | 12.70 |
| 8 | 0.13 | 0.22 | 2.10 | 19.60 |

Again high permeability superabsorbent polymer coated with a polyethyleneimine solution show superior permeability than equally coated conventional superabsorbent polymer. Now the experiments were conducted at low to optimum crosslinker content. Obviously, a crosslinker content of 0.15 mol % is the minimum to see an influence of coating. But even at this very low levels of addition of polyethyleneimine, the aquisition rate increase. Again, the performance of coated high permeability superabsorbent polymers in terms of acquisition rate is superior to that of conventional superabsorbent polymer. With an increase in the bulk crosslinker in the base polymer, there is an increase in the permeability (SFC) of the high permeability superabsorbent polymer. The acquisition times and rates are similar; however, the rewet (g) values increase for the 3rd and 4th insults with the higher bulk crosslinked base polymer.

Effect of increasing the bulk crosslinker in the high permeability superabsorbent polymer and coating with a single coating solution that contains both an amine and a crosslinker. Compared is the coating of a high permeability superabsorbent polymer with a crosslinker content of 0.083 mol % MBA with that of a high permeability superabsorbent polymer with a crosslinker content of 0.1 mol % MBA (table 8 and 9).

TABLE 8

Base polymer prepared by the method of Example 3 (2260)
Polyethyleneimine (33 wt % solids, Mw = 70,000)
Crosslinker: Ethylene glycol diglycidylether
Wetting Agent: Propylene glycol 125° C. 1 hr

| Sample | Sample | Coating Ratio | AUL 0.7 1 hr | CRC | SFC |
|---|---|---|---|---|---|
| 1 | Comparative Example 3 | 0.050 | 24.1 | 21.1 | 152.0 |
| 2 | PEI 0.25% Coated HP SAP | 0.050 | 21.8 | 19.9 | 365.3 |
| 3 | PEI 0.5% Coated HP SAP | 0.057 | 21.6 | 19.1 | 733.6 |
| 4 | PEI 0.75% Coated HP SAP | 0.065 | 21.7 | 18.6 | 713.6 |
| 5 | PEI 1% Coated HP SAP | 0.073 | 22.0 | 19.5 | 648.8 |

|  | 4-40 ml 0.9% NaCl insults | | | | | | | |
|---|---|---|---|---|---|---|---|---|
|  | Acquisition Time (sec) | | | | Acquisition Rate | | | |
| Sample | 1 | 2 | 3 | 4 | 1 | 2 | 3 | 4 |
| 1-Comp. Ex 3 | 78.7 | 160.5 | 203.4 | 259.5 | 0.51 | 0.25 | 0.20 | 0.15 |
| 2 | 61.1 | 67.4 | 84.4 | 101.0 | 0.65 | 0.59 | 0.47 | 0.40 |
| 3 | 62.1 | 74.4 | 77.0 | 90.2 | 0.64 | 0.54 | 0.52 | 0.44 |
| 4 | 60.8 | 66.3 | 69.7 | 85.0 | 0.66 | 0.60 | 0.57 | 0.47 |
| 5 | 59.5 | 61.0 | 65.2 | 78.8 | 0.67 | 0.66 | 0.61 | 0.51 |

TABLE 8-continued

Base polymer prepared by the method of Example 3 (2260)
Polyethyleneimine (33 wt % solids, Mw = 70,000)
Crosslinker: Ethylene glycol diglycidylether
Wetting Agent: Propylene glycol 125° C. 1 hr

| | 4-40 ml 0.9% NaCl insults Rewet (g) | | | |
|---|---|---|---|---|
| Sample | 1 | 2 | 3 | 4 |
| 1-Comp. Ex 3 | 0.12 | 0.14 | 0.39 | 3.85 |
| 2 | 0.17 | 0.12 | 0.4 | 9.1 |
| 3 | 0.11 | 0.08 | 0.22 | 7.9 |
| 4 | 0.12 | 0.11 | 0.48 | 7.7 |
| 5 | 0.07 | 0.1 | 0.47 | 12.1 |

TABLE 9

Base polymer prepared by the method of Example 3 (2260)
prepared at a higher bulk crosslinker level in the
polymerization (0.1 mole % MBA)
Polyethyleneimine (33 wt % solids, Mw = 70,000)
Crosslinker: Ethylene glycol diglycidylether
Wetting Agent: Propylene glycol 125° C. 1 hr

| Sample | Sample | Coating Ratio | AUL 0.7 1 hr | CRC | SFC |
|---|---|---|---|---|---|
| 1 | Comparative Example 3 | | 22.5 | 19.8 | 239.1 |
| 2 | PEI 0.25% Coated HP SAP | 0.050 | 21.6 | 20.1 | 477.1 |
| 3 | PEI 0.5% Coated HP SAP | 0.057 | 22.5 | 19.7 | 610.3 |
| 4 | PEI 0.75% Coated HP SAP | 0.065 | 22.1 | 19.2 | 813.9 |
| 5 | PEI 1% Coated HP SAP | 0.073 | 21.4 | 19.8 | 638.9 |

| | 4-40 ml 0.9% NaCl insults | | | | | | | |
|---|---|---|---|---|---|---|---|---|
| | Acquisition Time (sec) | | | | Acquisition Rate | | | |
| Sample | 1 | 2 | 3 | 4 | 1 | 2 | 3 | 4 |
| 1-Comp. Ex 3 | | | | | | | | |
| 2 | 65.3 | 75.8 | 86.3 | 104.9 | 0.61 | 0.53 | 0.46 | 0.38 |
| 3 | 58.2 | 70 | 75.3 | 90.9 | 0.69 | 0.57 | 0.53 | 0.44 |
| 4 | 66.5 | 72.7 | 79.6 | 96.5 | 0.60 | 0.55 | 0.50 | 0.41 |
| 5 | 66.1 | 81.4 | 87.5 | 109 | 0.61 | 0.49 | 0.46 | 0.37 |

| | 4-40 ml 0.9% NaCl insults Rewet (g) | | | |
|---|---|---|---|---|
| Sample | 1 | 2 | 3 | 4 |
| 1-Comp. Ex 3 | | | | |
| 2 | 0.09 | 0.21 | 0.74 | 8.7 |
| 3 | 0.06 | 0.08 | 0.34 | 12 |
| 4 | 0.11 | 0.21 | 6.4 | 16.5 |
| 5 | 0.09 | 0.11 | 0.89 | 11.3 |

Obviously increasing the bulk crosslinker in the high permeability superabsorbent polymer within the above range from 0.083 to 0.1 mol % shows no significant change in the absorption profile. Nevertheless, a bulk crosslinker content of 0.083 mol % seems to show improved acquisition datas.

Influence of the Amount of Wetting Agent in the Polyamine Coating Solution

TABLE 10

Base polymer prepared by the method of Example 3 (2260)
Polyethyleneimine (33 wt % solids, Mw = 70,000)
Crosslinker: Ethylene glycol diglycidylether
Wetting Agent: Propylene glycol 125° C. 1 hr

| Sample | Sample | PG in Coating (based on SAP) | Coating Ratio | AUL 0.7 1 hr | CRC | SFC |
|---|---|---|---|---|---|---|
| 1 | Comparative Example 3 | 2 wt % | 0.050 | 22.5 | 19.4 | 256.8 |
| 2 | HP SAP 1% PEI | 2 wt % | 0.053 | 21.7 | 19.3 | 410.2 |
| 3 | HP SAP 1% PEI | 4 wt % | 0.073 | 22.0 | 19.5 | 648.8 |
| 4 | HP SAP 1% PEI | 6 wt % | 0.093 | 22.5 | 19.3 | 552.8 |
| 5 | HP SAP 1% PEI | 8 wt % | 0.110 | 22.5 | 20 | 423 |

Comparison of Two Different Polyethyleneimines in the Coating Solution (Table 11 and 12)

TABLE 11

Base polymer prepared by the method of Example 3 (2260)
Polyethyleneimine (33 wt % solids, Mw = 750,000)
Crosslinker: Ethylene glycol diglycidylether
Wetting Agent: Propylene glycol 125° C. 1 hr
PEI Coated (BASF Lupasol PS) HP SAP

| Sample | | Coating Ratio | AUL 0.7 1 hr | CRC | SFC |
|---|---|---|---|---|---|
| 1 | Comparative Example 3 | 0.0500 | 24.1 | 21.1 | 152.4 |
| 2 | HP SAP 0.25% PEI Coated | 0.0500 | 21.6 | 20.3 | 238.6 |
| 3 | HP SAP 0.5% PEI Coated | 0.0550 | 22.4 | 20.3 | 392.2 |

| | 4-40 ml 0.9% NaCl insults | | | | | | | |
|---|---|---|---|---|---|---|---|---|
| | Acquisition Time (sec) | | | | Acquisition Rate | | | |
| Sample | 1 | 2 | 3 | 4 | 1 | 2 | 3 | 4 |
| 1-Comp. Ex 3 | 78.7 | 160.5 | 203.4 | 259.5 | 0.51 | 0.25 | 0.2 | 0.15 |
| 2 | 78.8 | 156.4 | 164.4 | 166 | 0.51 | 0.26 | 0.24 | 0.24 |
| 3 | 69.9 | 97.8 | 113.5 | 150.1 | 0.57 | 0.41 | 0.35 | 0.27 |

| | 4-40 ml 0.9% NaCl insults Rewet (g) | | | |
|---|---|---|---|---|
| Sample | 1 | 2 | 3 | 4 |
| 1-Comp. Ex 3 | 0.12 | 0.14 | 0.39 | 3.85 |
| 2 | 0.07 | 0.09 | 0.15 | 1.5 |
| 3 | 0.1 | 0.13 | 0.37 | 4.47 |

PEI Coated (Epomin) HP SAP

TABLE 12

Base polymer prepared by the method of Example 3 (2260)
Polyethyleneimine (33 wt % solids, Mw = 70,000)
Crosslinker: Ethylene glycol diglycidylether
Wetting Agent: Propylene glycol 125° C. 1 hr

| Sample | Sample | Coating Ratio | AUL 0.7 1 hr | CRC | SFC |
|---|---|---|---|---|---|
| 1 | Comparative Example 3 | 0.050 | 24.1 | 21.1 | 152.0 |
| 2 | PEI 0.25% Coated HP SAP | 0.050 | 21.8 | 19.9 | 365.3 |
| 3 | PEI 0.5% Coated HP SAP | 0.057 | 21.6 | 19.1 | 733.6 |
| 4 | PEI 0.75% Coated HP SAP | 0.065 | 21.7 | 18.6 | 713.6 |
| S | PEI 1% Coated HP SAP | 0.073 | 22.0 | 19.5 | 648.8 |
| 6 | PEI 2% Coated HP SAP | 0.107 | 21.5 | 17.4 | 661.4 |

TABLE 12-continued

Base polymer prepared by the method of Example 3 (2260)
Polyethyleneimine (33 wt % solids, Mw = 70,000)
Crosslinker: Ethylene glycol diglycidylether
Wetting Agent: Propylene glycol 125° C. 1 hr

| 7 | PEI 3% Coated HP SAP | 0.140 | 21.5 | 17.1 | 687.6 |
| 8 | PEI 4% Coated HP SAP | 0.173 | 19.5 | 16.7 | 722.3 |

4-40 ml 0.9% NaCl insults

| | Acquisition Time (sec) | | | | Acquisition Rate | | | |
|---|---|---|---|---|---|---|---|---|
| Sample | 1 | 2 | 3 | 4 | 1 | 2 | 3 | 4 |
| 1-Comp. Ex 3 | 78.7 | 160.5 | 203.4 | 259.5 | 0.51 | 0.25 | 0.2 | 0.15 |
| 2 | 61.1 | 67.4 | 84.4 | 101 | 0.65 | 0.59 | 0.47 | 0.40 |
| 3 | 62.1 | 74.4 | 77 | 90.2 | 0.64 | 0.54 | 0.52 | 0.44 |

| | 4-40 ml 0.9% NaCl insults Rewet (g) | | | |
|---|---|---|---|---|
| Sample | 1 | 2 | 3 | 4 |
| 1-Comp. Ex 3 | 0.12 | 0.14 | 0.39 | 3.85 |
| 2 | 0.17 | 0.12 | 0.4 | 9.1 |
| 3 | 0.11 | 0.08 | 0.22 | 7.9 |

The results show that the polyethyleneimine-type Epomin performs comparably. This could be found for the acquisition datas; the rewets for this polyethyleneimine-type are otherwise worse than the BASF Lupasol PS Type.

Summary of the Results

The experiments show that there are different results in comparison of polyamine surface crosslinked superabsorbent polymer and conventional surface crosslinked superabsorbent polymer. Said coating solution comprises a cationic compound as for example polyvinylamines or polyethylene imines and a crosslinking agent. Generally, polyamine coating leads to products, which exhibit better aquisition datas and have improved permeability by application in the absorbent core. Furthermore, the comparison between polyamine coated conventional superabsorbent polymer and polyamine coated high permeability superabsorbent polymer show that the high permeability superabsorbent polymers performs the best.

Comparative examples show, that a minimum of crosslinker has to be added to the cationic compound to get superior acquisition behaviour. Rising the crosslinker content above a certain limit gives no further benefits. The preferred range of the crosslinker content goes from 0.15 mol % to 5 mol %. Otherwise, small changes in content of the bulk crosslinker does not significantly influence the performance data.

Polyamine-coated absorbent fines having improved acquisition rates and composites/air laids made thereof.

Polyamine coated fines exhibit improved acquisition rates without tendency to gel-blocking. In detail, this aspect of the present invention concerns improved coated fines of particle sizes below 400 μm.

Composites or air-laids of this aspect of the present invention show an improved acquisition behavior and low rewets at the same time.

Example 1

A 10 L capacity polyethylene vessel, well insulated by foamed polymer material, is charged with 3400 g of demineralized water and 1400 g of acrylic acid. 8.4 g of methylene bisacrylamide is then added as crosslinker. At a temperature of 4° C., the initiators, consisting of 2.2 g of 2,2'-azobisamidinopropane dihydrochloride, dissolved in 25 g of demineralized water, 4 g of potassium peroxodisulfate, dissolved in 150 g of demineralized water, and 0.4 g of ascorbic acid, dissolved in 25 g of demineralized water, are added in succession stirred in. The reaction solution is then left to stand without stirring, and the temperature of the polymerization rises to about 94° C. A solid gel is obtained, and this gel is subsequently mechanically comminuted and adjusted to pH 6.0 by addition of 50% strength by weight sodium hydroxide solution The gel is then dried, ground and classified to a particle size distribution of 100-200 μm (base polymer 1a) resp. 200-300 μm (base polymer 1b).

Example 2

A 10 L capacity polyethylene vessel, well insulated by foamed polymer material, is charged with 3400 g of demineralized water and 1400 g of acrylic acid. 9.5 g of allyl methacrylate and 140.0 g of a 15% strength by weight aqueous solution of a polyamidoamine-epichlorhydrin adduct (RE-TEN 204 LS from Hercules) is then added as crosslinker. At a temperature of 4° C., the initiators, consisting of 2.2 g of 2,2'-azobisamidinopropane dihydrochloride, dissolved in 25 g of demineralized water, 4 g of potassium peroxodisulfate, dissolved in 150 g of demineralized water, and 0.4 g of ascorbic acid, dissolved in 25 g of demineralized water, are added in succession stirred in. The reaction solution is then left to stand without stirring, and the temperature of the polymerization rises to about 91° C. A solid gel is obtained, and this gel is subsequently mechanically comminuted and adjusted to pH 6.0 by addition of 50% strength by weight sodium hydroxide solution The gel is then dried, ground and classified to a particle size distribution of 100-300 μm (base polymer 2a) resp. 100-400 μm (base polymer 2 b).

Surface Crosslinking:

1 kg of the base polymer is sprayed in a plowshare mixer with the following solutions (simultaneously, but via two nozzles):

| Example | Base polymer | Nozzle 1 | Nozzle 2 |
|---|---|---|---|
| 3 | 1 b | 20 g of poly vinyl amine solution* | 2.0 g of ethylene glycol bisglycidyl ether<br>10 g of propylene glycol<br>20 g of demineralized water |
| 4 | 1 a | 12.5 g of poly vinyl amine solution* | 1.5 g of ethylene glycol bisglycidyl ether<br>10 g of propylene glycol<br>20 g of demineralized water |
| 5 | 2 b | 30 g of poly ethylene imine solution** | 1.5 g of ethylene glycol bisglycidyl ether<br>10 g of propylene glycol<br>20 g of demineralized water |
| 6 | 2 a | 20 g of poly ethylene imine solution** | 2.0 g of ethylene glycol bisglycidyl ether<br>10 g of propylene glycol<br>20 g of demineralized water |
| 7 | 2 b | 30 g of poly vinyl amine solution* | 0.5 g of ethylene glycol bisglycidyl ether<br>4.0 g of sodium formate<br>10 g of propylene glycol<br>20 g of demineralized water |
| 8 | 2 a | 10.0 g of poly ethylene imine solution** | 2.0 g of ethylene glycol bisglycidyl ether<br>10 g of propylene glycol<br>20 g of demineralized water |

-continued

| Example | Base polymer | Nozzle 1 | Nozzle 2 |
|---|---|---|---|
| 9 | 2 a | — | 0.2 g of ethylene glycol bisglycidyl ether<br>10 g of propylene glycol<br>20 g of demineralized water |

*poly vinyl amine solution: 25% strength by weight aqueous solution of poly vinyl amine (K value of 30)
**poly ethylene imine solution: Polymin G 100 (trade product from BASF AG, 50% strength by weight aqueous solution of poly ethylene imine)

The mixtures are then heated in a laboratory drying oven at 100° C. for 60 minutes. The products described herein (all of white color) have the following properties:

| Sample | CRC | Vortex time |
|---|---|---|
| 3 | 25.0 g/g | 12 s |
| 4 | 23.0 g/g | 8 s |
| 5 | 16.1 g/g | 24 s |
| 6 | 15.3 g/g | 14 s |
| 7 | 17.3 g/g | 22 s |
| 8 | 18.5 g/g | 17 s |
| 9* | 19.0 g/g | 32 s |
| 10* | 24.8 g/g | 20 s |
| 11* | 26.8 g/g | 24 s |
| 12* | 14.0 g/g | 19 s |

*Comparative example

Comparative Examples

Sample 10

1 kg of the base polymer 1 b is sprayed in a plowshare mixer with a solution consisting of 2.0 g of ethylene glycol bisglycidyl ether, 10 g of propylene glycol and 20 g of demineralized water. The mixture is the heated in a laboratory drying oven at 100° C. for 60 minutes. The dried product is then placed again in a plowshare mixer and sprayed with a mixture consisting of 20 g of a poly vinyl amine solution (25% strength by weight aqueous solution of poly vinyl amine, K value of 30) and 10 g of demineralized water. The mixture is then heated in a laboratory drying oven at 100° C. for 60 minutes.

Sample 11

1 kg of the base polymer 1 b is sprayed in a plowshare mixer with a solution consisting of 20 g of a poly vinyl amine solution (25% strength by weight aqueous solution of poly vinyl amine, K value of 30), 10 g of propylene glycol and 20 g of demineralized water. The mixture is the heated in a laboratory drying oven at 100° C. for 60 minutes.

Sample 12

1 kg of the base polymer 2 a is sprayed in a plowshare mixer with a solution consisting of 20 g of a poly vinyl amine solution (25% strength by weight aqueous solution of poly vinyl amine, K value of 30), 10 g of propylene glycol and 20 g of demineralized water. The mixture is the heated in a laboratory drying oven at 180° C. for 60 minutes. A product with yellow-brown color is obtained.

The invention claimed is:

1. A composite comprising a fibrous substrate and superabsorbent particles having a shell, wherein said shell comprises a cationic polymer crosslinked by the addition of a crosslinker and adhered to a hydrogel-forming polymer having a residual water content of less than 10 wt%, said particles prepared by applying a coating solution, containing the cationic polymer and the crosslinker, to the hydrogel-forming polymer, wherein the hydrogel-forming polymer is neutralized at least 50 mole percent and the cationic polymer comprises a polyamine or a polyimine material.

2. The composite of claim 1 wherein the cationic polymer comprises a polyamine material.

3. The composite of claim 2 wherein said polyamine is selected from the group consisting of (a) a polymer having primary amine groups; (b) a polymer having secondary amine groups; (c) a polymer having tertiary amine groups; and (d) mixtures thereof.

4. The composite of claim 1 wherein the crosslinker is selected from the group of sodium formate, a poly(ethylene glycol) diglycidyl ether, and mixtures thereof.

5. The composite of claim 1 wherein the particles have a CRC of at least 24 g/g.

6. The composite of claim 5 wherein the particles have a CRC of at least 28 g/g.

7. The composite of claim 6 wherein the particles have a CRC of at least 30 g/g.

8. The composite of claim 1 wherein the particles have a Pressure Absorbency Index of less than 120.

9. The composite of claim 8 wherein the particles have a Pressure Absorbency Index of less than 100.

10. The composite of claim 1 wherein the particles have a ratio of AUL (0.01 psi) to AUL (0.90 psi) of more than 2.0.

11. The composite of claim 10 wherein the particles have a ratio of AUL (0.01 psi) to AUL (0.90 psi) of more than 3.0.

12. The composite of claim 11 wherein the particles have a ratio of AUL (0.01 psi) to AUL (0.90 psi) of more than 3.5.

13. The composite of claim 1 wherein the particles have a CRC of at least 18 g/g and a Gel Bed Permeability of more than 800.

14. The composite of claim 13 wherein the particles have a CRC of at least 20 g/g and a Gel Bed Permeability of more than 1200.

15. The composite of claim 14 wherein the particles have a CRC of at least 22 g/g and a Gel Bed Permeability of more than 1500.

16. The composite of claim 1 wherein the particles have a Vortex Time of less than 30 seconds.

17. The composite of claim 16 wherein the particles have a Vortex Time of less than 20 seconds.

18. The composite of claim 17 wherein the particles have a Vortex Time of less than 10 seconds.

19. The composite of claim 1 wherein the particles have 80% of the particles are smaller than 400 μm.

20. The composite of claim 1 wherein 80% of the particles are smaller than 300 μm.

21. The composite of claim 1 wherein 80% of the particles are smaller than 200 μm.

22. The composite of claim 1 containing more than 30% by weight of the superabsorbent particles.

23. The composite of claim 1 containing more than 50% by weight of the superabsorbent particles.

24. The composite of claim 1 containing more than 60% by weight of the superabsorbent particles.

25. The composite of claim 1 wherein the particles have a Performance Parameter PP of less than 1500.

26. The composite of claim 25 wherein the particles have a Performance Parameter PP of less than 1000.

27. The composite of claim 26 wherein the particles have a Performance Parameter PP of less than 500.

28. The composite of claim 1 comprising (a) synthetic fibers and (b) cellulosic fibers as the fibrous substrate, and (c) superabsorbent particles, wherein a mixing ratio of synthetic fibers to cellulosic fibers can be varied from 100 to 0 synthetic fibers to 0 to 100 cellulosic fibers.

29. The composite of claim 28 wherein the composite can be prepared by (i) a procedure wherein (a), (b), and (c) are admixed at the same time, (ii) a procedure wherein a mixture of (a) and (b) is admixed with (c), (iii) a procedure wherein a mixture of (b) and (c) is admixed with (a), (iv) a procedure wherein a mixture of (a) and (c) is admixed with (by, (v) a procedure wherein (b) and (c) are admixed and (a) is continuously added to the mixture, (vi) a procedure wherein (a) and (c) are admixed and (b) is continuously added to the mixture, or (vii) a procedure wherein (b) and (c) are separately mixed with (a).

30. The composite of claim 28 prepared by a process wherein a layer of the superabsorbent particles is heated above a glass transition temperature of the particles to bind adjacent particles together, to bind the particles to the fibers, or a combination of both.

31. The composite of claim 30 wherein said layer is heated in the range of about 50° C. to about 100° C. during manufacture of a sheet material.

32. An air-laid article comprising superabsorbent particles having a shell, wherein said shell comprises a cationic polymer crosslinked by the addition of a crosslinker and adhered to a hydrogel-forming polymer having a residual water content of less than 10 wt %, said particles prepared by applying a coating solution, containing the cationic polymer and the crosslinker, to the hydrogel-forming polymer, wherein the hydrogel-forming polymer is neutralized at least 50 mole percent and the cationic polymer comprises a polyamine or a polyimine material.

33. The air-laid article of claim 32 containing more than 30% by weight superabsorbent particles.

34. The air-laid article of claim 32 containing more than 50% by weight superabsorbent particles.

35. The air-laid article of claim 32 containing more than 70% by weight superabsorbent particles.

36. The air-laid article of claim 32 containing more than 80% by weight superabsorbent particles.

37. The air-laid article of claim 32 wherein the superabsorbent particles have a Performance Parameter PP of less than 1500.

38. The air-laid article of claim 37 wherein the superabsorbent particles have a Performance Parameter PP of less than 500.

39. The air-laid article of claim 32 prepared by a process wherein a layer of superabsorbent particles is heated above a glass transition temperature of the particles to bind adjacent particles together.

40. The air-laid article of claim 39 wherein said layer is heated in the range of about 50° C. to about 100° C. during manufacture of a sheet material.

41. An absorbent article comprising (a) a liquid pervious top sheet, (b) a liquid impervious back sheet, and (c) an absorbent core positioned between said top sheet and said back sheet, wherein said absorbent core comprises particles comprising a fibrous substrate and superabsorbent particles having a shell, wherein said shell comprises a cationic polymer crosslinked by the addition of a crosslinker and adhered to a hydrogel-forming polymer having a residual water content of less than 10 wt %, said particles prepared by applying a coating solution, containing the cationic polymer and the crosslinker, to the hydrogel-forming polymer, wherein the hydrogel-forming polymer is neutralized at least 50 mole percent and the cationic polymer comprises a polyamine or a polyimine material.

42. The absorbent article of claim 41 wherein the core has a shakeout of less than 10%, by weight, of the particles.

43. The absorbent article of claim 41 further comprising an acquisition layer disposed between the topsheet and the core.

* * * * *